(12) United States Patent
Mateen et al.

(10) Patent No.: US 11,980,690 B2
(45) Date of Patent: *May 14, 2024

(54) CENTANAFADINE PHARMACEUTICAL FORMULATIONS, AND METHODS OF MAKING AND USING SAME

(71) Applicant: OTSUKA PHARMACEUTICAL CO., LTD., Tokyo (JP)

(72) Inventors: Syed Asfar Mateen, Robbinsville, NJ (US); Praveen Kumar Mididoddi, Pennington, NJ (US); Shailly Mehrotra, Furlong, PA (US); Susan Elizabeth Shoaf, Silver Spring, MD (US); Salin Gupta, Bridgewater, NJ (US); Kai Suzuki, Osaka (JP); Masahiro Hasegawa, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,728

(22) Filed: Jun. 1, 2023

(65) Prior Publication Data
US 2023/0338293 A1 Oct. 26, 2023

Related U.S. Application Data

(63) Continuation of application No. 18/072,473, filed on Nov. 30, 2022, now Pat. No. 11,759,426, which is a
(Continued)

(51) Int. Cl.
*A61K 9/16* (2006.01)
*A61K 31/40* (2006.01)
*A61K 31/403* (2006.01)

(52) U.S. Cl.
CPC ............ *A61K 9/167* (2013.01); *A61K 9/1611* (2013.01); *A61K 9/1617* (2013.01);
(Continued)

(58) Field of Classification Search
CPC .... A61K 9/167; A61K 9/1611; A61K 9/1617; A61K 9/1623; A61K 9/1635; A61K 9/1652; A61K 31/403
See application file for complete search history.

(56) References Cited

U.S. PATENT DOCUMENTS

| 8,747,895 B2 | 6/2014 | Venkatesh et al. |
| 11,564,885 B2 * | 1/2023 | Mateen ................ A61K 9/5084 |

(Continued)

FOREIGN PATENT DOCUMENTS

| EP | 3069715 A1 | 9/2016 |
| WO | WO-96/04908 A1 | 2/1996 |
| WO | WO-2007133203 A1 * | 11/2007 ........... A61K 9/1676 |

OTHER PUBLICATIONS

Brown et al., "Pharmacologic management of attention deficit hyperactivity disorder in children and adolescents: a review for practitioners," Transl Pediatr 7(1):36-47 (2018).
(Continued)

*Primary Examiner* — Ernst V Arnold
(74) *Attorney, Agent, or Firm* — MARSHALL, GERSTEIN & BORUN LLP

(57) ABSTRACT

Pharmaceutical formulation comprising centanafadine or a pharmaceutically acceptable salt thereof and an excipient, and related methods of manufacture and use, are disclosed.

29 Claims, 11 Drawing Sheets

Related U.S. Application Data continuation of application No. 17/677,726, filed on Feb. 22, 2022, now Pat. No. 11,564,885.

(60) Provisional application No. 63/241,839, filed on Sep. 8, 2021, provisional application No. 63/152,826, filed on Feb. 23, 2021.

(52) U.S. Cl.
CPC .......... *A61K 9/1623* (2013.01); *A61K 9/1635* (2013.01); *A61K 9/1652* (2013.01); *A61K 31/403* (2013.01)

(56) References Cited

U.S. PATENT DOCUMENTS

2007/0264323 A1  11/2007  Shojaei et al.
2012/0302619 A1  11/2012  Skolnick et al.
2014/0206740 A1* 7/2014  McKinney ........... A61K 31/403
                                                    514/412

OTHER PUBLICATIONS

International Search Report and Written Opinion from International Application No. PCT/JP2022/007314 dated Jun. 3, 2022.
Jain et al., "Recent technologies in pulsatile drug delivery systems," Biomatter 1(1):57-65 (2011).
Strawn et al., "Triple-bead mixed amphetamine salt for ADHD," Current Psychiatry 16(8):33-37 (2017).
Wigal et al., "Safety and Efficacy of Centanafadine Sustained-Release in Adults With Attention-Deficit Hyperactivity Disorder: Results of Phase 2 Studies," Neuropsychiatric Disease and Treatment, 16:1411-1426 (2020).
International Preliminary Report on Patentability from International Application No. PCT/JP2022/007314 dated Sep. 7, 2023.

* cited by examiner

CENTANAFADINE PHARMACEUTICAL FORMULATIONS, AND METHODS OF MAKING AND USING SAME

CROSS-REFERENCE TO RELATED APPLICATIONS

This is a Continuation of U.S. application Ser. No. 18/072,473, filed Nov. 30, 2022, which is a Continuation of U.S. application Ser. No. 17/677,726, filed Feb. 22, 2022 (now U.S. Pat. No. 11,564,885), which claims the benefit under 35 U.S.C. § 119(e) of U.S. Provisional Patent Application Nos. 63/152,826 filed Feb. 23, 2021, and 63/241,839, filed Sep. 8, 2021, the disclosures of which are hereby incorporated by reference herein.

BACKGROUND

Field of the Disclosure

The disclosure relates generally to pharmaceutical formulations of centanafadine and pharmaceutically acceptable salts thereof, and related methods of making and treatment, e.g. treatment of and prevention of central nervous system disorders and other conditions affected by monoamine neurotransmitters.

Brief Description of Related Technology (1R,5S)-1-(naphthalen-2-yl)-3-azabicyclo[3.1.0]hexane (centanafadine)

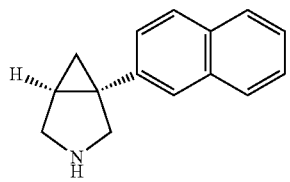 [SMILES: c1ccc2cc([C@]34CNC[C@H]3C4)ccc2c1]

[CAS 924012-43-1] is an unbalanced triple reuptake inhibitor with the most potency towards the norepinephrine reuptake transporter (NET), one-sixth as much towards the dopamine reuptake transporter (DAT), and one-fourteenth as much towards the serotonin reuptake transporter (SERT). There remains a need for novel pharmaceutical compositions comprising (1R,5S)-1-(naphthalen-2-yl)-3-azabicyclo[3.1.0]hexane, in free or pharmaceutically acceptable salt form.

SUMMARY

Provided herein are pharmaceutical formulations of centanafadine or a salt thereof, methods of making and uses thereof. The pharmaceutical formulations can include a plurality of regions comprising centanafadine or a pharmaceutically acceptable salt thereof, e.g. beads in which the plurality of beads each comprise a core particle comprising centanafadine or a salt thereof and an excipient.

Also provided herein are pharmaceutical formulations including centanafadine or a salt thereof, wherein the formulation is a solid oral formulation suitable for pediatric use.

Also provided herein are pharmaceutical formulations including centanafadine or a salt thereof and an excipient, wherein the pharmaceutical formulation has a multiphasic release profile when tested in acid media for 2 hours followed by pH 7.4 buffered medium. Also provided herein are pharmaceutical formulations including centanafadine or a salt thereof and an excipient, wherein the formulation exhibits in vivo delayed-sustained release profile.

Also provided herein are pharmaceutical formulations including a plurality of beads containing centanafadine or a salt thereof, the plurality of beads each comprising a core particle comprising centanafadine or a salt thereof and an excipient, wherein at least a portion of the core particles comprise centanafadine or a salt thereof in an amount in a range of about 70 wt. % to about 90 wt. %.

Also provided herein are medical uses and methods of treatment using a formulation according to the disclosure herein or use of a formulation according to the disclosure herein including administering a formulation according to the disclosure herein to an animal subject in need thereof, optionally a mammalian subject in need thereof, optionally a human in need thereof.

Also provided herein are methods of making a pharmaceutical formulation including centanafadine or a salt thereof, the method comprising compounding the centanafadine or salt thereof with a binder to make particles comprising centanafadine or a salt thereof having a defined particle size range, and disposing a coating over at least a portion of the particles.

DETAILED DESCRIPTION

Figure 1:
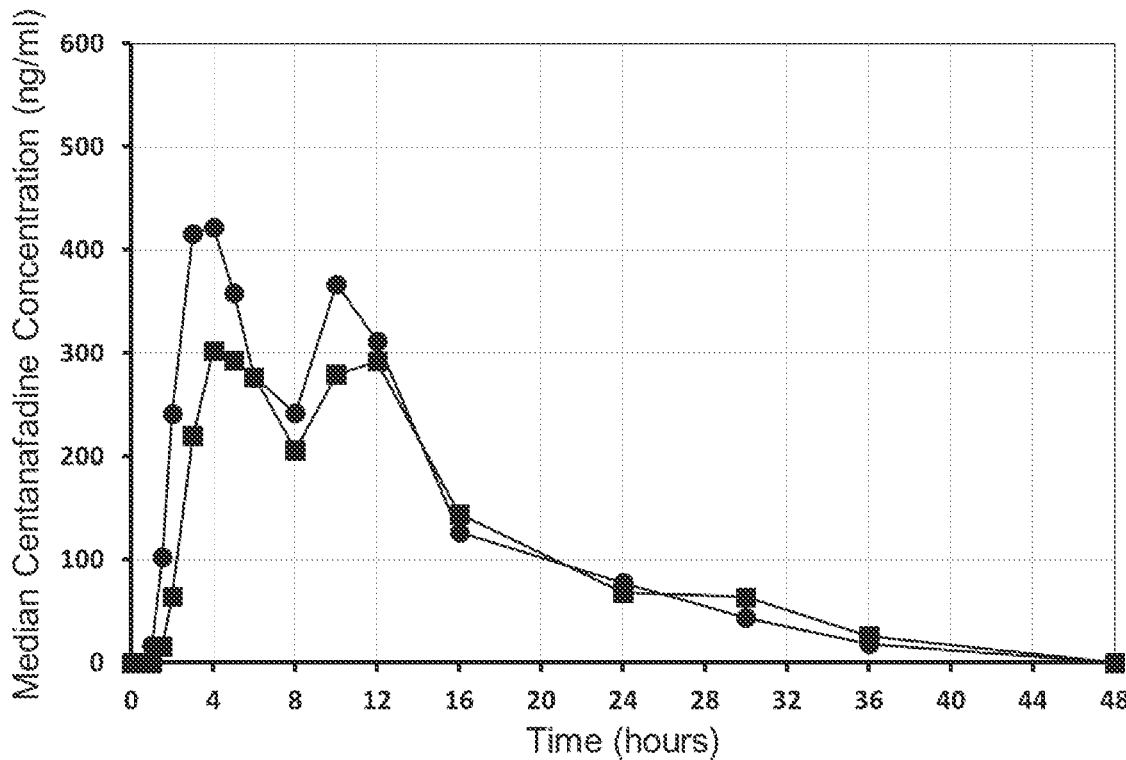
FIG. 1 is a graph of the in vivo absorption profiles of pharmaceutical formulations including centanafadine hydrochloride administered to subjects according to Example 2.

Described herein are pharmaceutical formulations and dosage forms suitable for delivery of centanafadine (CTN) or a pharmaceutically acceptable salt thereof. CTN is classified as a BSC Class I molecule, which is highly soluble and highly permeable. As used herein, CTN should be understood to refer to centanafadine, while pharmaceutically acceptable salts thereof are also considered in addition to or as one or more alternatives to CTN in every formulation, method, and use described herein, unless explicitly stated otherwise. For example, in every instance in which CTN is referred to, the disclosure specifically contemplates use of centanafadine hydrochloride as an option. One aspect of the formulation is a core/coating structure containing CTN in a core region and a modified release region over the core region, e.g. on the core region. Additional regions are also contemplated. For example, the core region can have an intermediate region between the core region and modified release region, for example in the form of a seal coating layer.

A formulation as described herein can be measured for the appropriate CTN dosage strength prior to administration, or the formulation can be packaged in unit dosage form, e.g. in capsules, sachets, etc. In the alternative, the formulation can be compounded in unit dosage form, e.g. by pressing into a monolithic unit form, such as a tablet.

One type of formulation includes a plurality of CTN-containing regions, the plurality of CTN regions can include one or more release characteristics, e.g. selected from delayed release, sustained release, immediate release, and delayed-sustained release. The regions can be physically joined or separate. For example, one type of formulation includes a plurality of CTN-containing beads (CTN beads), the plurality of CTN beads each including a core particle and an excipient. In embodiments, the plurality of CTN beads can include one or more of types of beads selected from a delayed release bead, a sustained release bead, an immediate release bead, and a delayed-sustained release bead.

The pharmaceutical formulation can be provided in unit dose form, for example as a collection of beads disposed in a capsule shell, or as a collection of beads disposed in a sachet. In another type of embodiment, a collection of granules is pressed into tablet form, with or without extragranular components, e.g. an extragranular disintegrant. Other forms will be evident to the skilled artisan in view of the disclosure herein.

Also provided herein is a pharmaceutical formulation comprising CTN and an excipient, wherein the pharmaceutical formulation has an in vivo absorption profile that is bimodal.

A pharmaceutical formulation as disclosed herein can be designed according to the disclosure herein to include one or more features or advantages such as: 1) a formulation can optionally be a pediatric formulation such that children or young adults that struggle with swallowing solid oral doses, such as, tablets or pills, or patients can be administered a CTN formulation via sprinkling (e.g., on applesauce or other soft foods, such as jellies) and swallowed without chewing, or administered via an enteral feeding tube; 2) the formulation can be effective for treating one or more conditions described herein when administered at a frequency of less than twice daily, e.g. on a schedule of once daily; 3) the formulation is stable when exposed to elevated temperatures, e.g. 40° C., and high humidity, e.g., 75% RH; 4) the formulation is suitable for manufacturing on a commercial scale.

As mentioned above, a formulation according to the disclosure can include a plurality of CTN beads, including one or more types selected from: an immediate release bead, a sustained release bead, a delayed release bead, and a delayed-sustained release bead. The plurality of CTN-containing beads can include at least a portion of the beads including a delayed release or delayed-sustained release coating, at least a portion of the beads including a sustained release coating, and at least a portion of the beads being immediate release beads. Such a formulation was shown to exhibit advantageous pharmacokinetics, to be suitable for administration to pediatric subjects, and suitable for administration once daily. Without intending to be bound by any particular theory, it is contemplated that the pharmacokinetics are influenced by the plurality of CTN beads having a combination of bead types, including immediate release, sustained release, and delayed release.

The pharmaceutical formulations and methods are contemplated to include embodiments including any combination of one or more of the additional optional elements, features, and steps further described below (including those shown in the Figures and Examples), unless stated otherwise.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

As used herein, the term sustained release is equivalent to extended release and prolonged release. A dosage form can be characterized by its overall release profile, e.g. the profile resulting from multiple regions when present in the dosage form. A dosage form exhibiting sustained release characteristics can be characterized as a sustained release dosage form, even if it further contains an immediate release region in addition to a sustained release formulation region, e.g. bead. Similarly, a dosage form exhibiting sustained release characteristics can be characterized as a sustained release dosage form, even if it further contains a delayed release region in addition to a sustained release formulation region, e.g. bead.

As used herein, the term wt. % is the weight percent based on the total weight of the thing described, e.g. of the core particle, or coating, or total bead, as described in context or explicitly. Unless described otherwise, the wt. % is intended to describe the weight percent based on dry weight (e.g., for a core particle following drying). Unless described otherwise, the terms "wt. %" and "% by weight" are used interchangeably herein.

While the description herein refers to beads, and beads such as those made by extrusion and spheronization can have certain advantages such as greater uniformity and size, particles of any size and shape and made by other processes are equally contemplated as alternatives, as are monolithic dosage forms.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

Unless expressly stated otherwise, all references to centanafadine herein are intended to encompass pharmaceutically-acceptable salts thereof, and for every reference to centanafadine herein the use of centanafadine hydrochloride is specifically contemplated as an embodiment.

Unless expressly stated otherwise, reference herein to a bead and properties thereof is intended to be interpreted as applying equally to a collection of beads (e.g., a plurality of such beads). Likewise, unless expressly stated otherwise, reference herein to a core particle and properties thereof is intended to be interpreted as applying equally to a collection of core particles (e.g., a plurality of such core particles).

As provided herein, centanafadine herein refers to (1R, 5S)-1-(naphthalen-2-yl)-3-azabicyclo[3.1.0]hexane and can include pharmaceutically acceptable salts thereof. Pharmaceutically acceptable salts are known in the art and include salts that are physiologically acceptable at the dosage amount and form to be administered, for example, hydrochloride salts. As used herein, "(1R,5S)-1-(naphthalen-2-yl)-3-azabicyclo[3.1.0]hexane" is also to be understood as embracing the compound in crystalline and amorphous form including, for example, polymorphs, solvates (including hydrates), unsolvated polymorphs (including anhydrates), conformational polymorphs, and amorphous forms of the compounds, as well as mixtures thereof. "Crystalline form" and "polymorph" may be used interchangeably herein, and are meant to include all crystalline forms of (1R,5S)-1-(naphthalen-2-yl)-3-azabicyclo[3.1.0]hexane, in free or pharmaceutically acceptable salt form, including, for example, polymorphs, solvates (including hydrates), unsolvated polymorphs (including anhydrates), and conformational polymorphs, as well as mixtures thereof, unless a particular crystalline form is referred to. In embodiments, CTN is provided as a CTN hydrochloride salt. In the description herein, the amounts of CTN, weight percentages of CTN, or ranges thereof in the pharmaceutical formulations, beads, core particles, etc., are applicable to centanafadine free base, as well as to pharmaceutically acceptable salts thereof, such that any description by weight should be viewed as both for CTN free base, and in addition in the alternative as description applicable to a pharmaceutically acceptable salt form, unless specified otherwise.

Bead Formulation

The pharmaceutical formulations herein can include a plurality of CTN-containing regions, e.g. beads, particles, or otherwise, wherein the CTN-containing regions can include one or more release properties selected from: immediate release, sustained release, delayed release bead, and delayed-sustained release. In the description below, CTN beads are described as an example of such formulation types. The characteristics for the formulations described, e.g. ratios of different bead types, are also applicable to unit dosage forms, e.g. collections of beads disposed in capsules.

In one type of embodiment, the plurality of beads includes a mixture of one or more immediate release beads and one or more sustained release beads. In embodiments, the amount of CTN by weight can be present at a ratio in a range of about 1:100 to about 1:1 in the collection of one or more immediate release beads to the collection of one or more sustained release beads. In embodiments, the amount of CTN by weight can be present at a ratio in a range of about 1:50 to about 1:1 in the collection of one or more immediate release beads to the collection of one or more sustained release beads, or in a range of about 1:20 to about 1:1, or in a range of about 1:15 to about 1:1, for example, 1:10.

In one type of embodiment, the plurality of beads includes a mixture of one or more immediate release beads and one or more delayed release beads. In embodiments, the amount of CTN by weight can be present at a ratio in a range of about 1:100 to about 1:1 in the collection of one or more immediate release beads to the collection of one or more delayed release beads. In embodiments, the amount of CTN by weight can be present at a ratio in a range of about 1:50 to about 1:1 in the collection of one or more immediate release beads to the collection of one or more delayed release beads, or in a range of about 1:20 to about 1:1, or in a range of about 1:15 to about 1:1, for example, 1:10.

In one type of embodiment, the plurality of beads includes a mixture of one or more delayed release beads and one or more sustained release beads. In embodiments, the amount of CTN by weight can be present at a ratio in a range of about 5:1 to about 1:5 in the collection of one or more delayed release beads to the collection of one or more delayed-sustained release beads, in a range of about 3:1 to about 1:3, or in a range of about 2:1 to about 1:2, or in a range of about 1.5:1 to about 1:1.5, for example about 1:1.

In one type of embodiment, the plurality of beads includes a mixture of one or more immediate release beads and one or more delayed-sustained release beads. In embodiments, the amount of CTN by weight can be present at a ratio in a range of about 1:100 to about 1:1 in the collection of one or more immediate release beads to the collection of one or more delayed-sustained release beads. In embodiments, the amount of CTN by weight can be present at a ratio in a range of about 1:50 to about 1:1 in the collection of one or more immediate release beads to the collection of one or more delayed-sustained release beads, or in a range of about 1:20 to about 1:1, or in a range of about 1:15 to about 1:1, for example, 1:10.

In one type of embodiment, the plurality of beads includes a mixture of one or more immediate release beads, one or more sustained release beads, and one or more delayed release beads. In embodiments, the ratio of CTN can be present in the one or more immediate release beads, one or more sustained release beads, and one or more delayed release beads at a ratio in a range of about 0.1-1:1-20:1-20 parts by weight based on the weight of CTN. In embodiments, the ratio of CTN can be present in the one or more immediate release beads, one or more sustained release beads, and one or more delayed release beads at a ratio in a range of about 0.5-1:5-20:5-20 parts by weight based on the weight of CTN. In embodiments, the ratio of CTN or pharmaceutically acceptable salt thereof can be present in the one or more immediate release beads, one or more sustained release beads, and one or more delayed release beads at a ratio in a range of about 0.7-1.3:3-6:3-6 parts by weight based on the weight of CTN. In embodiments, the ratio of CTN or pharmaceutically acceptable salt thereof can be present in the one or more immediate release beads, one or more sustained release beads, and one or more delayed release beads at a ratio in a range of about 0.7-1:5-15:5-15 parts by weight based on the weight of CTN. For example, the ratio of CTN or pharmaceutically acceptable salt thereof can be present in the one or more immediate release beads, one or more sustained release beads, and one or more delayed release beads can be 1:3.6:3.6.

In one type of embodiment, the plurality of beads comprises a mixture of one or more immediate release beads, one or more sustained release beads, and one or more delayed-sustained release beads. In embodiments, the ratio of CTN can be present in the one or more immediate release beads, one or more sustained release beads, and one or more delayed-sustained release beads at a ratio in a range of about 0.1-1:1-20:1-20 parts by weight based on the weight of CTN. In embodiments, the ratio of CTN or pharmaceutically acceptable salt thereof can be present in the one or more immediate release beads, one or more sustained release beads, and one or more delayed-sustained release beads at a ratio in a range of about 0.5-1:5-20:5-20 parts by weight based on the weight of CTN. In embodiments, the ratio of CTN or pharmaceutically acceptable salt thereof can be present in the one or more immediate release beads, one or more sustained release beads, and one or more delayed-sustained release beads at a ratio in a range of about 0.7-1.3:3-6:3-6 parts by weight based on the weight of CTN. In embodiments, the ratio of CTN or pharmaceutically acceptable salt thereof can be present in the one or more immediate release beads, one or more sustained release beads, and one or more delayed-sustained release beads at a ratio in a range of about 0.7-1:5-15:5-15 parts by weight based on the weight of CTN. For example, the ratio of CTN or pharmaceutically acceptable salt thereof can be present in the one or more immediate release beads, one or more sustained release beads, and one or more delayed-sustained release beads at a ratio of about 1:3.6:3.6 parts by weight based on the weight of CTN.

In embodiments, the immediate release beads can be present in the formulation or dosage form in an amount in a range of about 1% to about 75% based on the total weight of the plurality of CTN beads in the formulation or dosage form. For example, the immediate release beads are present in the formulation in an amount in a range of about 1% to about 60%, or about 1% to about 50%, or about 5% to about 50%, or about 5% to about 40%, or about 5% to about 30%, or about 5% to about 25%, or about 10% to about 30%, 9% to about 55% or about 18% to about 28%, or about 5% to about 20%, or about 5% to about 15%, or about 1% to about 25%, or about 1% to about 10%, based on the total weight of the plurality of CTN beads. In embodiments, the immediate release beads are present in the formulation in an amount in a range of about 1% to about 50% based on the total weight of the plurality of CTN beads. In embodiments, the immediate release beads are present in the formulation in an amount in a range of about 1% to about 25% based on the total weight of the plurality of CTN beads. In embodiments, the immediate release beads are present in the formulation in an amount in a range of about 1% to about 10% based on the total weight of the plurality of CTN beads. In embodiments, the immediate release beads can be present in the formulation in an amount in a range of about 9% to about 19% based on the total weight of the plurality of CTN beads; such embodiments are particularly contemplated when the drug loading in the bead is about 40 wt. % to about 60 wt. %, e.g. 50 wt. %. In embodiments, the immediate release beads can be present in the formulation in an amount in a range of about 40% to about 55% based on the total weight of the plurality of CTN beads; such embodiments are particularly contemplated when the drug loading in the bead is about 5 wt. % to about 15 wt. %, e.g. 10 wt. %. In embodiments, the immediate release beads are present in the formulation in an amount in a range of about 18% to about 28% based on the total weight of the plurality of CTN beads.

In embodiments, the immediate release bead, or a bead core, can include CTN in an amount in a range of about 5 wt. % to about 90 wt. % based on the total weight of the bead or bead core. For example, the immediate release bead or a bead core can include CTN in an amount in a range of about 5 wt. % to about 85 wt. %, about 5 wt. % to about 80 wt. %, about 5 wt. % to about 60 wt. %, about 5 wt. % to about 30 wt. %, or about 25 wt. % to about 60 wt. %, or about 40 wt. % to about 60 wt. %, or about 5 wt. % to about 15 wt. %, based on the total weight of the bead or bead core. In embodiments, the immediate release bead or a bead core can include CTN in an amount in a range of 5 wt. % to 15 wt. % based on the total weight of the bead or bead core. In embodiments, the immediate release bead or a bead core can include CTN in an amount in a range of 40 wt. % to 60 wt. % in the immediate release bead based on the total weight of the immediate release bead or bead core. In embodiments, the immediate release bead or a bead core can include the CTN in an amount in a range of about 70 wt. % to about 90 wt. %, or about 75 wt. % to about 80 wt. % based on the total weight of the immediate release bead or bead core. In embodiments, the pharmaceutical formulation herein can include a first immediate release bead or bead core wherein the CTN is present in an amount in a range of 5 wt. % to 15 wt. % based on the total weight of the immediate release bead or bead core and a second immediate release bead wherein the CTN is present in an amount in a range of 40 wt. % to 60 wt. % based on the total weight of the immediate release bead or bead core. In embodiments, the pharmaceutical formulation can include a bead core having CTN in an amount in a range of about 70 wt. % to about 90 wt. %, or about 75 wt. % to about 80 wt. % based on the total weight of the bead core, together with one or more coatings over the bead core.

In embodiments, the sustained release beads can be present in the formulation or dosage form in an amount in a range of about 5% to about 80% based on the total weight of the plurality of CTN beads in the formulation or dosage form. For example, the sustained release beads are present in the formulation in an amount in a range of about 5% to about 65%, or about 10% to about 60%, or about 20% to about 60%, or about 25% to about 55%, or about 25% to about 50%, or about 35% to about 55%, or about 40% to about 50%, or about 45% to about 55%, based on the total weight of the plurality of CTN beads. In embodiments, the sustained release beads are present in the formulation in an amount in a range of about 5% to about 65% based on the total weight of the plurality of CTN beads. In embodiments, the sustained release beads are present in the formulation in an amount in a range of about 35% to about 55% based on the total weight of the plurality of CTN beads, or about 42% to about 48%.

In embodiments, the sustained release bead can include the CTN in an amount in a range of 10 wt. % to 95 wt. % in the sustained release bead based on the total weight of the sustained release bead. For example, the sustained release bead can include the CTN in an amount in a range of about 30 wt. % to about 90 wt. %, about 40 wt. % to about 90 wt. %, or about 50 wt. % to about 90 wt. %, or about 50 wt. % to about 80 wt. %, or about 50 wt. % to about 70 wt. %, based on the total weight of the sustained release beads. In embodiments, the sustained release bead can include the CTN in an amount in a range of 40 wt. % to 90 wt. % in the sustained release bead based on the total weight of the sustained release bead. In embodiments, the sustained release bead can include the CTN in an amount in a range of wt. % to 70 wt. % in the sustained release bead based on the total weight of the sustained release bead.

In embodiments, the delayed release beads can be present in the formulation or dosage form in an amount in a range of about 5% to about 80% based on the total weight of the plurality of CTN beads in the formulation or dosage form. For example, the delayed release beads are present in the formulation in an amount in a range of about 5% to about 65%, or about 10% to about 70%, or about 20% to about 60%, or about 25% to about 55%, or about 25% to about 50%, or about 30% to about 55%, or about 36% to about 46%, or about 40% to about 50%, based on the total weight of the plurality of CTN beads. In embodiments, the delayed release beads are present in the formulation in an amount in a range of about 5% to about 65% based on the total weight of the plurality of CTN beads. In embodiments, the delayed release beads are present in the formulation in an amount in a range of about 30% to about 55% based on the total weight of the plurality of CTN beads, or about 38% to about 44%.

In embodiments, the delayed release bead can include the CTN in an amount in a range of 10 wt. % to 95 wt. % in the delayed release bead based on the total weight of the delayed release bead. For example, the delayed release bead can include the CTN in an amount in a range of about 30 wt. % to about 90 wt. %, about 40 wt. % to about 90 wt. %, or about 50 wt. % to about 90 wt. %, or about 50 wt. % to about 85 wt. %, or about 50 wt. % to about 70 wt. %, based on the total weight of the delayed release bead. In embodiments, the delayed release bead can include the CTN in an amount in a range of 40 wt. % to 90 wt. % in the delayed release bead based on the total weight of the delayed release bead. In embodiments, the delayed release bead can include the CTN in an amount in a range of 50 wt. % to 70 wt. % in the delayed release bead based on the total weight of the delayed release bead.

In embodiments, the immediate release beads can be present in the formulation or dosage form in an amount in a range of about 1% to about 10% by weight of the formulation or dosage form, the sustained release beads are present in the formulation or dosage form in an amount of about 45% to about 55% by weight of the formulation or dosage form, and the delayed release beads are present in the formulation or dosage form in an amount in a range of about 40% to about 50% of the weight of the formulation or dosage form. In embodiments, the immediate release beads can be present in the formulation or dosage form in an amount in a range of about 4% to about 28% by weight of the formulation or dosage form, the sustained release beads can be present in the formulation or dosage form in an amount of about 15% to about 40% by weight of the formulation or dosage form, and the delayed release beads can be present in the formulation or dosage form in an amount in a range of about 30% to about 65% of the weight of the formulation or dosage form.

In embodiments, the immediate release beads can be present in the formulation or dosage form in an amount in a range of about 11% to about 17% by weight of the formulation or dosage form, the sustained release beads are present in the formulation or dosage form in an amount of about 42% to about 48% by weight of the formulation or dosage form, and the delayed release beads (or delayed-sustained release beads) are present in the formulation or dosage form in an amount in a range of about 38% to about 44% of the weight of the formulation or dosage form; such embodiments are particularly contemplated when the drug loading in each bead type is about 5 wt. % to about 10 wt. %, about 45 wt. % to about 55 wt. %, and about 45 wt. % to about 55 wt. %, based on the total weight of the beads, respectively.

In embodiments, the immediate release beads can be present in the formulation or dosage form in an amount in a range of about 43% to about 49% by weight of the formulation or dosage form, the sustained release beads can be present in the formulation or dosage form in an amount of about 25% to about 31% by weight of the formulation or dosage form, and the delayed release beads can be present in the formulation or dosage form in an amount in a range of about 38% to about 44% of the weight of the formulation or dosage form; such embodiments are particularly contemplated when the drug loading in each bead type is about 45 wt. % to about 55 wt. %.

Core Bead Formulation

The plurality of CTN beads each include a core particle. The core particle includes CTN and an excipient. The CTN bead can consist of an uncoated core particle itself. As further described below, CTN beads can include a core particle and one or more coatings.

In embodiments, the core particles can be characterized by having a distribution of particle sizes. In embodiments, at least a portion of the core particles, or all of the core particles, of the plurality of CTN beads can have a core particle size (maximum diameter) of about 0.2 mm to about 2 mm, or about 0.3 mm to about 1.5 mm, about 0.4 mm to about 1.5 mm. For example, at least a portion of the core particles of the plurality of CTN beads have a core particle size of about 0.2 mm to about 2 mm, or about 0.3 mm to about 1.5 mm, about mm to about 1.4 mm, or about 0.4 mm to about 1.3 mm, or about 0.4 mm to about 1.2 mm, or about 0.4 mm to about 1.1 mm, or about 0.5 mm to about 1 mm, or about 0.5 mm to mm, or about 0.5 mm to about 0.71 mm. In embodiments at least a portion of the core particles of the plurality of CTN beads have a core particle size of about 0.5 mm to about mm. In embodiments, the core particles of the plurality of CTN beads have a core particle size of about 0.5 mm to about 0.71 mm. Core particle sizes can be selected by sieving, for example, to reject particles having sizes outside the desired range. In embodiments, the distribution of particles sizes of the core particles can be characterized by at least 60% by weight of the core particles having a particle size in a range of about 0.4 mm to about 1.5 mm. For example, the distribution of particles sizes of the core particles can be characterized by at least 60% by weight of the core particles having a particle size in a range of about 0.4 mm to about 1.4 mm, or about 0.4 mm to about 1.3 mm, or about 0.4 mm to about 1.2 mm, or about 0.4 mm to about 1.1 mm, or about 0.5 mm to about 1 mm, or about mm to 0.85 mm, or about 0.5 mm to about 0.71 mm. In embodiments, the distribution of particles sizes of the core particles is characterized by at least 60% by weight of the core particles having a particle size in a range of about 0.5 mm to about 0.71 mm. In embodiments, the distribution of particles sizes of the core particles is characterized by at least 80% by weight of the core particles having a particle size in a range of about 0.4 mm to about 1.5 mm. For example, the distribution of particles sizes of the core particles is characterized by at least 80% by weight of the core particles having a particle size in a range of about 0.4 mm to about 1.4 mm, or about 0.4 mm to about 1.3 mm, or about 0.4 mm to about 1.2 mm, or about 0.4 mm to about 1.1 mm, or about 0.5 mm to about 1 mm, or about mm to 0.85 mm, or about 0.5 mm to about 0.71 mm. In embodiments, the distribution of particles sizes of the core particles is characterized by at least 80% by weight of the core particles having a particle size in a range of about 0.5 mm to about 0.71 mm. In embodiments, the distribution of particles sizes of the core particles is characterized by at least 90% by weight of the core particles having a particle size in a range of about 0.4 mm to about 1.5 mm. For example, the distribution of particles sizes of the core particles is characterized by at least 90% by weight of the core particles having a particle size in a range of about 0.4 mm to about 1.4 mm, or about 0.4 mm to about 1.3 mm, or about 0.4 mm to about 1.2 mm, or about 0.4 mm to about 1.1 mm, or about 0.5 mm to about 1 mm, or about mm to 0.85 mm, or about 0.5 mm to about 0.71 mm. In embodiments, the distribution of particles sizes of the core particles is characterized by at least 90% by weight of the core particles having a particle size in a range of about 0.5 mm to about 0.71 mm. In embodiments, the plurality of CTN beads can have a median particle size (diameter) in a range of about 0.2 mm to about 2.8 mm. For example, the plurality of CTN beads can have a median particle size (diameter) in a range of about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm. In embodiments, the plurality of CTN beads can have a median particle size (diameter) in a range of about 0.5 mm to about 0.71 mm.

The amount of CTN in the core particles can be an amount in a range of about 5 wt. % to about 95 wt. %. In embodiments, at least a portion of the plurality of CTN beads include core particles including the CTN in an amount in a range of about 5 wt. % to about 75 wt. %. For example, at least a portion of the plurality of CTN beads include core particles including the CTN in an amount in a range of about 5 wt. % to about 70 wt. %, or about 10 wt. % to about 70 wt. %, or about 20 wt. % to about 60 wt. %, or about 30 wt. % to about 60 wt. %, or about 40 wt. % to about 60 wt. %, or about 45 wt. % to about 55 wt. %. In embodiments, at least a portion of the plurality of CTN beads include core particles including the CTN in an amount in a range of about 45 wt. % to about 55 wt. %. In embodiments, at least a portion of the plurality of CTN beads include core particles including the CTN in an amount of about 50 wt. %. For example, immediate release beads can include a core particle including the CTN in an amount of about 10 wt. %, or about 50 wt. %. In embodiments, at least a portion of the plurality of CTN beads include core particles including the CTN in an amount in a range of about 25 wt. % to about 95 wt. %. For example, at least a portion of the plurality of CTN beads include core particles including the CTN in an amount in a range of about 25 wt. % to about 90 wt. %, or about 35 wt. % to about 90 wt. %, or about 45 wt. % to about 90 wt. %, or about 50 wt. % to about 85 wt. %, or about 60 wt. % to about 85 wt. %, or about 75 wt. % to about 85 wt. %, or about 50 wt. %, about 60 wt. %, about 70 wt. %, or about 80 wt. %. In embodiments, at least a portion of the plurality of CTN beads include core particles including the CTN in an amount in a range of about 75 wt. % to about 85 wt. %. In embodiments, at least a portion of the plurality of CTN beads include core particles including the CTN in an amount of about 80 wt. %. For example, sustained release beads can include a core particle including the CTN in an amount of about 80 wt. %. For example, the delayed release beads include a core particle including the CTN in an amount in a range of about 80 wt. %.

The core particles disclosed herein include an excipient. In embodiments, the excipient includes one or more materials selected from a filler, a binder, a glidant, a surfactant, a polymer coating, a lubricant, a disintegrant, and a plasticizer. In embodiments, the excipient can include one or more materials selected from a filler, a binder, a glidant, a surfactant, a polymer coating, and a plasticizer. In embodiments, the excipient can include a filler and a binder. In embodiments, the excipient can include a binder and a polymer coating. In embodiments, the excipient can include a filler, a binder, and a polymer coating. In embodiments, the excipient can include a filler, a binder, a polymer coating, and a plasticizer. In embodiments, the pharmaceutical formulation can be free of disintegrants. In embodiments, a dosage form containing the pharmaceutical formulation can be free of disintegrants.

Fillers can include, but are not limited to, lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dehydrate. In one type of embodiment, the filler is not water soluble, although it may absorb water. In one type of embodiment, the filler is a spheronization aid. Spheronization aids can include one or more of crospovidone, carrageenan, chitosan, pectinic acid, glycerides, β-CD, cellulose derivatives, microcrystalline cellulose, powdered cellulose, polyplasdone crospovidone, and polyethylene oxide, for example. In one type of embodiment, the filler includes microcrystalline cellulose.

Binders can include, but are not limited to, cellulose ethers, methyl cellulose, ethyl cellulose, hydroxyethyl cellulose, propyl cellulose, hydroxypropyl cellulose, lower-substituted hydroxypropyl cellulose, hydroxypropylmethyl cellulose (hypromellose, e.g. hypromellose 2910, METHOCEL™ E-5 [CAS 9004-65-3] same as hydroxypropylmethyl cellulose HPMC available from Sigma or DuPont®), carboxymethyl cellulose, starch, pregelatinized starch, acacia, tragacanth, gelatine, polyvinyl pyrrolidone (povidone, PVP), cross-linked polyvinyl pyrrolidone, sodium alginate, microcrystalline cellulose, and lower-substituted hydroxypropyl cellulose. In one type of embodiment, the binders are selected from wet binders. In one type of embodiment, the binder is selected from cellulose ethers, e.g. hypromellose.

Surfactants can include, but are not limited to, anionic surfactants, including sodium lauryl sulfate, sodium deoxycholate, dioctyl sodium sulfosuccinate, and sodium stearyl fumarate, nonionic surfactants, including polyoxyethylene ethers, and polysorbate 80, and cationic surfactants, including quaternary ammonium compounds. In one type of embodiment the surfactant is selected from anionic surfactants, e.g. sodium lauryl sulfate.

Disintegrants can include, but are not limited to, starch, sodium cross-linked carboxymethyl cellulose, croscarmellose sodium, croscarmellose calcium, cross-linked polyvinyl pyrrolidone, and sodium starch glycolate, low-substituted hydroxypropyl cellulose, and hydroxypropyl starch.

Glidants can include, but are not limited to, polyethylene glycols of various molecular weights, magnesium stearate, calcium stearate, calcium silicate, fumed silicon dioxide, magnesium carbonate, magnesium lauryl sulfate, aluminum stearate, stearic acid, palmitic acid, cetanol, stearol, and talc.

Lubricants can include, but are not limited to, stearic acid, magnesium stearate, calcium stearate, aluminum stearate, and siliconized talc.

In embodiments, the excipient can include one or more materials selected from lactose, mannitol, corn starch, microcrystalline cellulose, hydroxypropyl cellulose, hydroxypropyl methylcellulose (hypromellose), polyvinyl pyrrolidone, talc, polysorbate 80, glycerol monostearate, triethyl citrate, polyvinyl alcohol-polyethylene glycol graft copolymer (e.g., Kollicoat® IR CAS 96734-39-3 available from Sigma) and silica. In embodiments, the excipient can include microcrystalline cellulose and mannitol. In embodiments, the excipient can include microcrystalline cellulose, talc, hypromellose, and polysorbate 80. In embodiments, the excipient can include microcrystalline cellulose. In embodiments, the core particles can include an excipient containing microcrystalline cellulose.

The amount of filler in the core particle is not particularly limited. In embodiments, the amount of filler (e.g. microcrystalline cellulose) can be in a range of about 10 wt. % to about 90 wt. %, about 10 wt. % to about 75 wt. %, or about 10 wt. % to about 60 wt. %, or at least 10 wt. %, or at least 15 wt. %, for example about 20 wt. %, or about 30 wt. %, or about 40 wt. %, or about 50 wt. %.

The amount of binder in the core particle is not particularly limited. In embodiments, the amount of binder (e.g. hypromellose and/or polyvinyl alcohol-polyethylene glycol graft copolymer) can be in a range of about 1 wt. % to about 10 wt. %, or about 2 wt. % to about 8 wt. %, or about 4 wt. % to about 6 wt. %, for example about 5 wt. %.

The amount of surfactant, e.g. as a processing aid, in the core particle is not particularly limited. In embodiments, the amount of surfactant (e.g. microcrystalline cellulose) can be in a range of about 0.1 wt. % to about 1 wt. %, or about 0.2 wt. % to about 0.8 wt. %, or about 0.4 wt. % to about 0.6 wt. %, for example about 0.5 wt. %.

Coatings

One type of embodiment of a pharmaceutical formulation disclosed herein includes a plurality of beads wherein at least a portion of the plurality of beads is coated. In embodiments, at least a portion of the plurality of beads can be uncoated. In embodiments, the coating can be one or more coatings selected from a delayed release coating, a sustained release coating, and a delayed-sustained release coating. In embodiments, at least a portion of the plurality of beads can include a delayed release coating. In embodiments, at least a portion of the plurality of beads can include a sustained release coating. In embodiments, at least a portion of the plurality of beads can include a delayed-sustained release coating.

The coating material disclosed herein, e.g. a polymer, can be a delayed release coating. In embodiments, the delayed release coating can be one that will dissolve in intestinal juices at a pH level higher than that of the stomach, e.g. a pH of 4.5 or greater, such as within the small intestine, and therefore permit release of the active substance in the regions of the small intestine, or later, and substantially not in the upper portion of the GI tract. In one type of embodiment, the enteric material begins to dissolve in an aqueous solution at pH between about 4.5 to about 5.5. In another type of embodiment, the delayed release material rapidly dissolves in an aqueous solution at pH of about 5. In another type of embodiment, the delayed release material rapidly dissolves in an aqueous solution at pH of about 5.5. For example, a pH-sensitive material can be selected such that it will not undergo significant dissolution until the dosage form has emptied from the stomach. The pH of the small intestine gradually increases from about 4.5 to about 6.5 in the duodenal bulb to about 7.2 in the distal portions of the small intestine (ileum). In another type of embodiment, the delayed release material will dissolve at a pH of at least 7, or at least 7.2, or at least 7.4, e.g. to target release in the distal portion of the small intestine or colon. In another type of embodiment, the delayed release material is insoluble in water and gastric juices, but will instead swell to provide a membrane through which the CTN active can diffuse. An insoluble polymer can also be selected such that it swells at a particular pH threshold, e.g. at a pH of at least 7, or at least 7.2, or at least 7.4, e.g. to target release in the distal portion of the small intestine or colon.

The delayed release coating materials can include, but are not limited to, one or more of the following: cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. EUDRAGIT®-L and -S series, including L 100-55, L 30 D-55, L 100, S 100, L 12.5, and S 12.5, available from Evonik Industries of Essen, North Rhine-Westphalia, Germany; polyvinyl acetate; fats; oils; waxes; fatty alcohols; shellac; zein; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); and polyurethane. A combination of delayed release coatings may also be used. In one type of embodiment, the delayed release coating dissolves at pH 7.0 or higher, or 7.2 or higher, or 7.4 or higher, e.g. to provide release in the colon. For example, the delayed release coating can be selected from a copolymer of methacrylic acid and methyl methacrylate, and a copolymer of methacrylic acid and ethyl acrylate. In embodiments, the delayed release coating can include one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer. In embodiments, the delayed release coating can include one or more materials selected from a copolymer of methacrylic acid, methyl methacrylate, and methyl acrylate, and a methacrylic acid-acrylate copolymer. In embodiments, the delayed release coating can include a copolymer of methyl arylate, methyl methacrylate, and methacrylic acid, e.g. in a molar ratio of about 7:3:1 (e.g., Eudragit® FS 30 D). Eudragit® FS 30 D is poly(methyl acrylate-CO-methyl methacrylate-CO-methacrylic acid [CAS 26936-24-3] available from Evonik Industries. In other embodiments, the delayed release coating will not include cationic copolymers of ethyl acrylate, methyl methacrylate, and methacrylic acid ester with quaternary ammonium groups (e.g. Eudragit® RL and Eudragit® RS polymers). Eudragit® RL 30 D and Eudragit® RS 30 D are aqueous dispersions of copolymers of acrylic acid and methacrylic acid esters with a low content of quaternary ammonium groups available from Evonik Industries.

Figure 7:
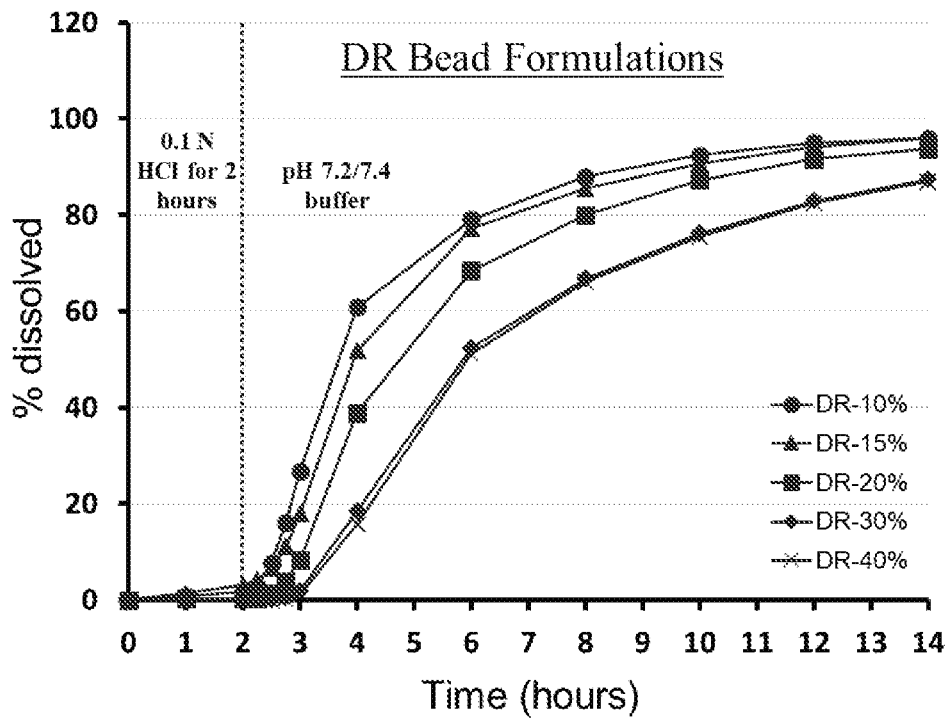
FIG. 7 is a graph of the in vitro dissolution profile.

In embodiments, the delayed release coating can also provide sustained release of CTN. In embodiments, the delayed release coating will include an anionic polymer, optionally including carboxylate moieties. FIG. 7 shows that a delayed release coating based on a copolymer of methyl acrylate, methyl methacrylate, and methacrylic acid, e.g. in a molar ratio of about 7:3:1 (e.g., Eudragit® FS 30 D) also has a sustained release function. Without intending to be bound by any particular theory, it is possible that the since the poly(methyl acrylate-co-methyl methacrylate-co-methacrylic acid) polymer is anionic, having negatively charged carboxylate moieties (ratio of carboxyl groups to ester groups approx. 1:10), and centanafadine is a positively-charged secondary amine, the polymer could be influencing the rate of release of centanafadine from the beads due to ionic interaction.

Examples of some delayed release coatings are disclosed in U.S. Pat. No. 5,225,202, including beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit® L30D) (F. W. Goodhart et al., Pharm. Tech., pp. 64-71, April 1984); copolymers of methacrylic acid and methacrylic acid methylester (Eudragit® polymers), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthalates, e.g., those having a free carboxyl content. See also Remington® Pharmaceutical Sciences, A. Osol, ed., Mack Pub. Co., Easton, Pa. (16th ed. 1980) at pages 1590-1593, and Zeitova et al. (U.S. Pat. No. 4,432,966), for descriptions of suitable enteric coating compositions.

The coating material disclosed herein, e.g. a polymer, can be a sustained release coating. A non-limiting list of suitable sustained release materials include hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained release material which is capable of imparting sustained release of the CTN may be used in accordance with the present invention. In embodiments, the sustained release coatings can include one or more materials selected from alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In one type of embodiment, the sustained release coating material is insoluble in water.

In embodiments, the sustained release coating can include one or more materials selected from an alkylcellulose such as ethylcellulose, acrylic acid polymer, a methacrylic acid polymer, an acrylic acid copolymer, a methacrylic acid copolymer, and a cellulose ether hydroxyalkylcelluloses (especially hydroxypropylmethylcellulose) and carboxyalkylcelluloses; In embodiments, the sustained release coating can include one or more materials selected from a hydroxyalkylcellulose, a carboxyalkylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, a poly(acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer. In embodiments, the sustained release polymers can include one or more materials selected from poly[ethyl acrylate, methyl methacrylate, trimethylammonioethyl methacrylate chloride], hydroxypropylmethylcellulose, and poly[ethyl acrylate, methyl methacrylate]. In embodiments, the sustained release polymer can include poly[ethyl acrylate, methyl methacrylate], e.g., in a molar ratio of about 2:1 (e.g., Eudragit® NM 30 D). In embodiments, the sustained release coating can include one or more materials selected from the EUDRAGITO—RL, -RS, -NE, and -NM series, including RL30D, RS30D, NE 30 D, NM 30 D, available from Evonik Industries. A combination of sustained release coatings may also be used. Eudragit® NM 30D [CAS 9010-88-4] and Eudragit® NE [CAS 9010-88-2] are an aqueous dispersion of a neutral copolymer based on ethyl acrylate and methacrylate of approximately 30% polymer content available from Evonik Industries. In embodiments, the sustained release polymer can include ethylcellulose, e.g. Aquacoat® ECD 30 D Coating available from DuPont®.

One or more plasticizers can be added to the delayed release coatings and/or sustained release coatings in order to increase their pliability and reduce brittleness, as it is known in the art. Suitable plasticizers are known in the art and include, for example, butyl citrates, triethyl citrate, diethyl phthalate, dibutyl sebacate, PEGs (e.g. PEG 6000), acetyl triethyl citrate, and triacetin. In one type of embodiment, the plasticizer is triethyl citrate. While some delayed release coatings and/or sustained release coatings are flexible and do not require addition of plasticizers, more brittle polymers (e.g., Eudragit® L/S types, Eudragit® RL/RS, and Eudragit® FS 30 D) benefit from plasticizers, e.g. in the range of 5 wt. % to 30 wt. % based on the dry polymer mass, e.g. about 8 wt. % to about 12 wt. % of PlasACRYL® T20 available from Evonik Industries, an anti-adherent system which contains glycerol monostearate, triethyl citrate and polysorbate 80 with a solid content of about 20%.

One or more anti-tacking agents (antiadherents) can also be added to an enteric coating mixture in order to reduce the tackiness of the film and prevent agglomeration, as it is known in the art. Anti-tacking agents include talc, and glyceryl monostearate, fumed silica (e.g., AEROSIL® 200 available from Evonik Industries), precipitated silica (e.g., SIPERNAT® PQ), and magnesium stearate, for example. Anti-tacking agents can be used in any suitable quantity, for example in a range of about 10 wt. % to 100 wt. % based on dry polymer mass, or about 1 wt. % to about 30 wt. %, or about 10 wt. % to about 50 wt. %, or about 10 wt. % to about 30 wt. %, or about 15 wt. % to about 30 wt. %. For example, in one embodiment the amount of talc is in a range of 15 wt. % to about 30 wt. %, based on dry polymer mass. In another embodiment the amount of talc is in a range of 1 wt. % to about 10 wt. %, based on dry polymer mass.

One or more surfactants can also be added to the delayed release coating and/or the sustained release coating in order to improve substrate wettability and/or stabilize suspensions, as it is known in the art. Surfactants include Polysorbate 80, sorbitan monooleate, and sodium dodecyl sulfate, for example.

The delayed release coating and/or the sustained release coating can be formed by any suitable process. Coating processes include pan coating, fluid bed coating, and dry coating (e.g., heat dry coating and electrostatic dry coating), for example. Pan coating and fluid bed coating using solvent are well established processes. In liquid coating, the enteric material and optional excipients (e.g. pigments, plasticizers, and/or anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus, whereas in an alternative the coating fluid is applied by top spraying, and in another alternative tangential spray is applied.

The amount of delayed release coating applied is sufficient to achieve desired release characteristics. For example, in one embodiment the amount of delayed release coating will be sufficient to meet United States Pharmacopeia (USP) <711> requirements (USP 43-NF 38 2S) for delayed-release dosage forms, by not releasing 10.0 wt. % of drug after 2 hours in 0.1N HCl. In another aspect, the formulation will be sufficient to release at least 80% of the active in the buffer stage, e.g. using the dissolution method of USP 43-NF 37 2S section <711>.

In one type of embodiment, the median amount of delayed release coating disposed over the core particle is at least 10 wt. % of the total weight of the CTN bead. In embodiments, the median amount of delayed release coating disposed over the core particle is in a range of about 10 wt. % to about 50 wt. %, or about 10 wt. % to about 40 wt. %, or about 10 wt. % to about 30 wt. %, or about 20 wt. %, or about 12 wt. % to about 50 wt. %, or about 12 wt. % to about 35 wt. %, based on the total weight of the CTN bead. In embodiments, the median amount delayed release coating disposed over the core particle is in a range of about 15 wt. % to about 45 wt. % based on the total weight of the CTN bead.

In one type of embodiment, the median amount of sustained release coating disposed over the core particle is at least 5 wt. % of the total weight of the coated CTN bead. In embodiments, the median amount of sustained release coating disposed over the core particle is in a range of about 5 wt. % to about 50 wt. %, or about 7.5 wt. % to about 45 wt. %, or about 10 wt. % to about 40 wt. %, or about 15 wt. %, or about 5 wt. % to about 40 wt. %, 15 wt. % to about 40 wt. %, or about 20 wt. % to about 40 wt. %, based on the total weight of the coated CTN bead. In embodiments, the median amount of sustained release coating disposed over the core particle is about 20 wt. % to about 40 wt. %, based on the total weight of the coated CTN bead.

In another embodiment the median amount of sustained release coating disposed over the core particle is at least 5 wt. % by weight gain based total weight of the uncoated CTN bead. In embodiments, the median amount of sustained release coating disposed over the core particle is in a range of about 5 wt. % to about 60 wt. %, or about 15 wt. % to about 60 wt. %, or about 20 wt. % to about 50 wt. %, or about 5 wt. % to about 40 wt. %, 15 wt. % to about 40 wt. %, or about 20 wt. % to about 40 wt. %, based on the total weight of the uncoated CTN bead. In embodiments, the median amount of sustained release coating disposed over the core particle is about 20 wt. % to about 40 wt. %, based on the total weight of the uncoated CTN bead.

Additional lubricant (glidant, anti-tack agent) can be added to the coated beads in powder form. Anti-tacking agents include talc, glyceryl monostearate, fumed silica (e.g., AEROSIL® 200), and precipitated silica (e.g., SIPERNAT® PQ), for example. For example talc powder can be added to the coated beads, for example in an amount of 0.1 wt. % to about 3 wt. % based on the total bead weight.

Additionally, the coatings disclosed herein can further include a pore former. The rate of CTN release through the release coating materials can be low and be increased by the addition pore formers to the coating. Pore formers are often hydrophilic polymers, which dissolve in water and/or gastric media, to form pores in the coating layer. The amount and type of pore former material can be selected to affect the release profile and achieve a desired release profile. In embodiments, the pore former can include one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and a saccharide. In embodiments, the pore former can include one or more materials selected from hydroxypropyl methylcellulose, hydroxypropylcellulose, and polyvinylpyrrolidone. In embodiments, the pore former includes hydroxypropyl methylcellulose. In embodiments, the pore former does not include polyvinylpyrrolidone. In embodiments, the pore former does not include polyvinyl pyrrolidone when the release coating includes ethylcellulose. The pore former can be included in the release coating in an amount in a range of about 5 wt. % or more, or about 10 wt. % or more, or about 13 wt. % or more, or about 15 wt. % or more, or about 5 wt. % to about 20 wt. %, based on the total weight of the coating. In embodiments, the pore former is present in an amount of about 15 wt. %, based on the total weight of the coating, or less than 50 wt. % or less than 20 wt. %% or in a range of about 1 wt. % to about 16 wt. %, or about 1 wt. % to about 12 wt. %, based on the total weight of the coating.

It is also contemplated herein that at least a portion of or the entirety of the plurality of beads includes a coating that includes only a soluble polymer which does not affect release of CTN from the formulation, such as a seal coating. In embodiments, the seal coating can include hydroxypropyl methylcellulose. In embodiments, the core beads can be coated with a seal coating prior to other coatings. In embodiments, at least a portion of the core particles are seal coated.

In some embodiments, the pharmaceutical formulation can include the plurality of CTN beads enclosed in one or more containers, for example selected from a capsule, sachet, and stick-pack. In embodiments, the pharmaceutical formulation includes the plurality of CTN beads enclosed in a capsule. Soft and hard capsules are known. In one embodiment, the capsule is a hard capsule, e.g. a gelatin capsule or a vegetable-based hard capsule.

Thus, for example, one type of embodiment combining various of the features described above includes a pharmaceutical formulation including a plurality of CTN beads, the beads including a core particle comprising CTN and a filler (optionally microcrystalline cellulose and/or mannitol), wherein the core particles are characterized by a distribution of particle sizes (maximum diameter) in a range of about 0.2 mm to about 1.5 mm, or about 0.3 mm to about 1.2 mm, or about 0.5 mm to about 0.85 mm, and wherein the core particles can include an optional coating surrounding the core particle, wherein the plurality of CTN beads includes an immediate release bead, a sustained release bead, and a delayed release bead.

A unit dosage form containing a CTN formulation according to the disclosure herein can include any suitable strength of CTN. For example, the amount of CTN in a unit dosage form can be in a range of 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 490 mg, e.g., 50 mg to 250 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg.

Functional Characteristics

As mentioned above, the pharmaceutical formulation or dosage form can advantageously be designed to have one or more pharmacokinetic characteristics, e.g. in humans. The pharmaceutical formulations herein can be characterized by the amount of CTN released in vitro over a given time period. In embodiments wherein the pharmaceutical formulation includes immediate release beads, at least 90% of the CTN or salt thereof is released from the immediate release beads at a time in a range of 0 to 2 hours. In embodiments wherein the pharmaceutical formulation includes sustained release beads, at least 90% of the CTN is released from the sustained release beads at a time in a range of 2 to 6 hours. In embodiments wherein the pharmaceutical formulation includes delayed release beads, at least 90% of the CTN or salt thereof is released from the delayed release beads at a time in a range of 4 to 14 hours. In embodiments wherein the pharmaceutical formulation includes delayed-sustained release beads, at least 90% of the CTN or salt thereof is released from the delayed-sustained release beads at a time in a range of 4 to 14 hours.

In embodiments, the formulation or dosage form can be characterized by one or more release profiles, in vivo and/or in vitro, selected from immediate release, sustained release, delayed release, and delayed-sustained release. In embodiments, the formulation, e.g. one suitable for pediatric use, optionally can have a multiphasic release profile when tested in acid media for 2 hours followed by pH 7.4 buffered medium. For example, the release profile when determined according to USP <711> using Apparatus I (basket) in 1000 mL 0.1N hydrochloric acid at 37° C.+/−0.5° C. at 100 rpm for 2 hours, followed by Apparatus I (basket) in 1000 mL pH 7.4 phosphate buffer solution at 37° C.+/−0.5° C.) at 100 rpm for 16 hours can have a multiphasic release profile, optionally an at least biphasic release profile, optionally an at least triphasic release profile. Such a profile can optionally be characterized by release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points. In another type of embodiment, such a profile can be characterized by release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points. Further optionally, the release profile can be characterized by a release of 49% to 73% at the 4-hour mark.

A pharmaceutical formulation herein optionally can be characterized by providing an in vivo absorption profile that is bimodal. In embodiments, the pharmaceutical formulation with a bimodal in vivo absorption profile provides a first centanafadine plasma $C_{max}$ at a time in a range of 0 to 4.5 hours, or about 0.5 hours to about 2 hours, or about 3.5 hours to about 4.5 hours. In embodiments, the first centanafadine plasma $C_{max}$ provided by the plurality of CTN beads is in a range of about 320 ng/mL to about 420 ng/mL, or about 325 ng/mL to about 390 ng/mL. In embodiments, a pharmaceutical formulation with a bimodal in vivo absorption profile provides a second centanafadine plasma $C_{max}$ at a time in a range of about 6 hours to 10 hours, or about 7 hours to 9 hours, or about 7.5 to about 8.5 hours. In embodiments, the second centanafadine plasma $C_{max}$ provided by the plurality of CTN beads is in a range of about 450 ng/mL to about 550 ng/mL, or about 470 ng/mL to about 530 ng/mL. In embodiments, the in vivo absorption profile has a first centanafadine plasma $C_{max}$ and a second centanafadine plasma $C_{max}$, wherein the first centanafadine plasma $C_{max}$ and second centanafadine plasma $C_{max}$ are separated by a time in a range of 1.5 to 8.5 hours, or about 2 hours to about 6 hours, or about 3 hours to about 5 hours.

A pharmaceutical formulation as described herein, and uses thereof, can be designed to provide one or more of the following pharmacokinetic profile characteristics.

The formulation can provide the subject with a relatively quick increase in plasma concentration of centanafadine to approach or meet a therapeutic concentration in a relatively short amount of time. Thus, for example, the formulation can provide an adult subject with a centanafadine plasma concentration at 1 hour post-dose ($C_{1h}$) of at least 150 ng/mL, or at least 200 ng/mL, or at least 250 ng/mL, or at least 280 ng/mL, or in a range of about 180 ng/mL to about 610 ng/mL, or about 200 ng/mL to about 590 ng/mL, or about 220 ng/mL to about 540 ng/mL, or about 245 ng/mL to about 490 ng/mL; optionally such exposure can be achieved with a dosage strength in a range of about 145 mg to about 185 mg CTN, e.g. 164.4 mg CTN.

The formulation can provide an adult subject with a cumulative CTN plasma exposure in a subject at 1 hour post-dose ($AUC_{0-1h}$) of at least 30 ng·h/mL, or at least 40 ng·h/mL, or at least 100 ng·h/mL, or at least 200 ng·h/mL, or in a range of about 30 ng·h/mL to about 500 ng·h/mL, or about 32 ng·h/mL to about 480 ng·h/mL, or about 36 ng·h/mL to about 440 ng·h/mL, or about 40 ng·h/mL to about 400 ng·h/mL; optionally such exposure can be achieved with a dosage strength in a range of about 145 mg to about 185 mg CTN, e.g. 164.4 mg CTN.

The formulation can maintain the plasma concentration of CTN in an adult subject in a therapeutic range for an extended period of time, for continuous efficacy. Thus, for example, the formulation can provide a CTN plasma concentration post-dose which remains at least at least 200 ng/mL, or at least 250 ng/mL, or at least 280 ng/mL, or at least 300 ng/mL, or at least 1000 ng/mL, or at least 1500 ng/mL, or in a range of about 150 ng/mL to about 4125 ng/mL, or about 160 ng/mL to about 3960 ng/mL, or about 180 ng/mL to about 3630 ng/mL, or about 200 ng/mL to about 3300 ng/mL over the time period 2 to 8 hours post-dose; optionally such plasma concentration can be achieved with a dosage strength in a range of about 145 mg to about 185 mg CTN, e.g. 164.4 mg CTN.

The formulation or use thereof can provide an adult subject with a cumulative CTN plasma exposure over the time period 0-8 hours post-dose ($AUC_{0-8h}$) of at least 1275 ng·h/mL, or at least 1530 ng·h/mL, or at least 1700 ng·h/mL, or at least 2500 ng·h/mL, or in a range of about 1275 ng·h/mL to about 6250 ng·h/mL, or about 1275 ng·h/mL to about 6250 ng·h/mL, or about 1360 ng·h/mL to about 6000 ng·h/mL, or about 1530 ng·h/mL to about 5500 ng·h/mL, or about 1700 ng·h/mL to about 5000 ng·h/mL; optionally such exposure can be achieved with a dosage strength in a range of about 145 mg to about 185 mg CTN, e.g. 164.4 mg CTN. The formulation can provide a cumulative plasma exposure over the time period 2-8 hours post-dose ($AUC_{2-8h}$) of at least 1050 ng·h/mL, or at least 1120 ng·h/mL, or at least 1330 ng·h/mL, or at least 2000 ng·h/mL, or at least 2500 ng·h/mL, or in a range of about 1050 ng·h/mL to about 5250 ng·h/mL, or about 1120 ng·h/mL to about 5040 ng·h/mL, or about 1260 ng·h/mL to about 4620 ng·h/mL, or about 1330 ng·h/mL to about 4410 ng·h/mL, or about 1400 ng·h/mL to about 4200 ng·h/mL; optionally such exposure can be achieved with a dosage strength in a range of about 145 mg to about 185 mg CTN, e.g. 164.4 mg CTN.

The pharmaceutical formulation or use thereof can provide an adult subject with a concentration of CTN in the plasma at 12 hours after administration (Cia) of at least 95 ng/mL, or at least 160 ng/mL, or at least 230 ng/mL, or at least 360 ng/mL, or in a range of about 95 ng/mL to about 450 ng/mL, or about 100 ng/mL to about 435 ng/mL, or about 110 ng/mL to about 400 ng/mL, or about 30 ng/mL to about 360 ng/mL; optionally such plasma concentration can be achieved with a dosage strength in a range of about 145 mg to about 185 mg CTN, e.g. 164.4 mg CTN.

The pharmaceutical formulation or use thereof can provide an adult subject with a relatively rapidly declining plasma concentration of CTN subsequent to 12 hours after administration, to promote a relatively low plasma concentration of CTN at 16 hours after administration and until the next dose. Thus, for example, the ratio of plasma concentration at 16 hours after administration to the plasma concentration at 12 hours after administration ($C_{16h}/C_{12h}$) can be less than 1, or 0.75 or less or 0.5 or less or 0.3 or less, or in a range of about 0.5 to 0.1; optionally such ratio can be achieved with a dosage strength in a range of about 145 mg to about 185 mg CTN, e.g. 164.4 mg CTN.

The pharmaceutical formulation or use thereof can provide an adult subject with a concentration of CTN in the plasma at 16 hours after administration of less than 375 ng/mL, or less than 300 ng/mL, or less 250 ng/mL, or less than 230 ng/mL, or less than 200 ng/mL, or less than 100 ng/mL, or in a range of about 60 ng/mL to about 375 ng/mL, or about 64 ng/mL to about 300 ng/mL, or about 76 ng/mL to about 250 ng/mL, or about 80 ng/mL to about 300 ng/mL; optionally such exposure can be achieved with a dosage strength in a range of about 145 mg to about 185 mg CTN, e.g. 164.4 mg CTN. For example, the plasma concentration can be relatively low at such a time to facilitate repeated once daily dosing without accumulation of CTN. In another aspect, the plasma concentration can be relatively low at such a time to avoid one or more adverse effects, e.g. insomnia in the subject, e.g. when the administration takes place in the morning.

The pharmaceutical formulation or use thereof can provide an adult subject with a cumulative CTN plasma exposure in the 24-hour period after administration ($AUC_{0-24h}$) of at least 2400 ng·h/mL, or at least 2880 ng·h/mL, or at least 3200 ng·h/mL, or at least 5000 ng·h/mL, or at least 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL. The pharmaceutical formulation or use thereof can provide an adult subject with a cumulative CTN plasma exposure in the 48-hour period after administration ($AUC_{0-48h}$) of at least 2400 ng·h/mL, or 2880 ng·h/mL, or 3200 ng·h/mL, 5000 ng·h/mL, or 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL; optionally such exposure can be achieved with a dosage strength in a range of about 145 mg to about 185 mg CTN, e.g. 164.4 mg CTN.

The pharmaceutical formulation or use thereof can provide an adult subject with a cumulative CTN plasma exposure in the period after administration ($AUC_{0-inf}$) of at least 2400 ng·h/mL, or 2880 ng·h/mL, or 3200 ng·h/mL, 5000 ng·h/mL, or 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL; optionally such exposure can be achieved with a dosage strength in a range of about 145 mg to about 185 mg CTN, e.g. 164.4 mg CTN.

The pharmaceutical formulation or use thereof can provide an adult subject with a time until maximum CTN plasma concentration ($t_{max}$) in a range of about 1.5 hours to about 11 hours, or about 2.25 hours to about 10 hours, or about 2.7 hours to about 8.8 hours, or about 3 hours to about 8 hours, or about 4 hours to about 6 hours.

The pharmaceutical formulations disclosed herein can be characterized by the mechanism of release of the active pharmaceutical ingredient (API), e.g., centanafadine hydrochloride. In embodiments, one or more of the plurality of CTN beads has a release mechanism including one or more of dissolution, diffusion, erosion, osmosis, partitioning, swelling, and targeting. In embodiments, one or more of the plurality of CTN beads has a diffusion release mechanism. In embodiments, one or more of the plurality of CTN beads has a porous matrix leading to a diffusion release mechanism. In embodiments, one or more of the plurality of CTN beads has a pH-triggered diffusion release mechanism. In embodiments, one or more of the plurality of CTN beads has a combination of pH-triggered dissolution release mechanism and diffusion release mechanism. In embodiments, as disclosed in part above, the delayed release beads have a combination of pH-triggered dissolution release mechanism and diffusion release mechanism. As used herein, the term "porous matrix" refers to an insoluble frame comprising a matrix of pores. In embodiments, at least a portion of the plurality of beads include a porous matrix. In embodiments, the sustained release beads comprise a porous matrix.

Pediatric Formulations

Also contemplated herein is a pharmaceutical formulation including CTN or a pharmaceutically acceptable salt thereof, wherein the formulation is a solid oral formulation suitable for pediatric use. In embodiments, the solid oral formulation suitable for pediatric use is selected from one or more types comprising beads, orodispersible tablet, orodispersible film, mini-tablet, chewable tablet, and soft-chew. In embodiments, the solid oral formulation suitable for pediatric use includes beads, such as a plurality of CTN beads as disclosed herein.

In embodiments, the solid oral formulation suitable for pediatric use can be characterized by one or more release profiles, in vivo and/or in vitro, selected from immediate release, sustained release, delayed release, and delayed-sustained release. In embodiments, the solid oral formulation suitable for pediatric use can have a multiphasic release profile when tested in acid media for 2 hours followed by pH 7.4 buffered medium. For example, the release profile when determined according to USP <711> using Apparatus I (basket) in 1000 mL 0.1N hydrochloric acid at 37° C.+/−0.5° C. at 100 rpm for 2 hours, followed by Apparatus I (basket) in 1000 mL pH 7.4 phosphate buffer solution at 37° C.+/−0.5° C.) at 100 rpm for 16 hours can have a multiphasic release profile, optionally an at least biphasic release profile, optionally an at least triphasic release profile. Such a profile can optionally be characterized by release of about 22% to about 45% CTN at the 3-hour mark, further optionally by release of about 40% to about 65% of CTN at the 8-hour mark, and further optionally by release of about 65% to about 95% of CTN at the 12-hour mark, and optionally such rates of release at all three time points. In another embodiment, such a profile can be characterized by release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points. Further optionally, the release profile can be characterized by a release of 49% to 73% at the 4-hour mark.

In embodiments, the solid oral formulation suitable for pediatric use comprises plurality of centanafadine (CTN) beads as disclosed herein, the plurality of CTN beads each comprising a core particle comprising CTN or a pharmaceutically acceptable salt thereof and an excipient. In embodiments, the solid oral formulation suitable for pediatric use has a median bead size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm.

Delayed-Sustained Release Profile

Also contemplated herein is a pharmaceutical formulation or dosage form comprising CTN thereof and an excipient, wherein the formulation exhibits in vivo delayed-sustained release profile.

In one type of embodiment, the formulation is a solid oral formulation and/or a semisolid oral formulation as disclosed herein. In embodiments, the formulation can comprise a core and a coating disposed over the core. In embodiments, the coating can be characterized by a pH-dependent dissolution trigger. In embodiments, the coating disposed over the core begins to dissolve at a pH of at least 7, optionally in a range of about 7 to about 8, optionally in a range of about 7.2 to about 7.6. In embodiments, the coating begins to dissolve at a pH in a range of about 7.2 to about 7.6. In embodiments, the coating begins to dissolve at a pH of about 7.4. In embodiments, the coating can include anionic polymer. In embodiments, the coating can comprise a methacrylic acid polymer. In embodiments, the coating comprises one or more polymers selected from co-polymerized methacrylic acid/methacrylic acid methyl esters, co-polymerized methacrylic acid/methyl methacrylate, co-polymerized methylacrylate/methyl methacrylate/methacrylic acid. In embodiments, one or more polymers selected from a copolymer of methacrylic acid, methyl methacrylate, and methyl acrylate, and a methacrylic acid-acrylate copolymer. In embodiments, the coating comprises a copolymer of methyl acrylate, methyl methacrylate, and methacrylic acid (e.g. in a molar ratio of about 7:3:1), e.g., Eudragit® FS 30 D. In embodiments, the delayed release coating can also provide sustained release of CTN. In embodiments, the delayed release coating will include an anionic polymer, optionally including carboxylate moieties. FIG. 7 shows that a delayed release coating based a copolymer of methyl acrylate, methyl methacrylate, and methacrylic acid, e.g. in a molar ratio of about 7:3:1 (e.g., Eudragit® FS 30 D) also has a sustained release function. Without intending to be bound by any particular theory, it is possible that the since the poly (methyl acrylate-co-methyl methacrylate-co-methacrylic acid) polymer is anionic, having negatively charged carboxylate moieties (ratio of carboxyl groups to ester groups approx. 1:10), and centanafadine is a positively-charged secondary amine, the polymer could be influencing the rate of release of centanafadine from the beads due to ionic interaction. In embodiments which include an immediate release region (e.g. bead), a sustained release region (e.g. bead), and a third region (e.g. bead) which has a delayed release aspect, the delayed release region or bead can be lacking or substantially lacking a sustained release aspect. This type of embodiment can be designed such that the elimination phase after a CTN dose is not unduly extended, e.g. such that the plasma concentration of CTN at 12 hours post-dose is less than 250 ng/mL, or 220 ng/mL or less, or 200 ng/mL or less, or 180 ng/mL or less, as described above.

Method of Making

A region or core particle including CTN can be formed by any suitable process. In one embodiment, the core particle is formed by granulating a mixture of CTN with an excipient and milling the resulting granules to a desired particle size range, optionally further with sieving to a selected particle size range. A core particle can be formed by extrusion and spheronization of a mixture of CTN with an excipient. Granulating processes can include fluid bed granulation, wet granulation, hot melt granulation, and spray congealing, for example. Other processes include slugging and roller compaction. As it is known in the art, the mixtures which are to be granulated can first be dry-blended. The dry-blended dry ingredients can be mixed with water, prior to extrusion. In another type of embodiment, inert seeds, such as non-pareil seeds or spheronized microcrystalline cellulose seeds, can be coated with a mixture including CTN and a binder to form a coating region including CTN over the inert seed. Wet beads obtained from the spheronizer can be dried in a fluid bed processor to a desired moisture content, and optionally heat cured. At the end of the drying and curing process, if desired the beads can be blended together with an anti-tacking agent, optionally by fluidizing the anti-tacking agent in the same air flow at ambient temperature to improve handling.

A specifically contemplated method includes methods of making a pharmaceutical formulation including CTN, including compounding the CTN with a binder to make particles including the CTN having a defined particle size range, and disposing a coating over at least a portion of the particles. In embodiments, the compounding includes extrusion. In embodiments, the compounding can further include spheronization after extrusion. The choice of extruder screen and spheronizer can determine the desired bead size prior to drying. In embodiments, the CTN particles can be dried after spheronization. For example, the process can include moistening a powder mixture of CTN and excipients, forming extrudates through extrusion, breaking and rounding the extrudates to round particles through spheronization, and drying the finished particles. An anti-tacking agent can be applied to the particles.

It has been found that extrusion and spheronization of a mixture of CTN with an excipient can provide desirable core particles with a distribution of core particle sizes as described herein and one or more other desirable properties. In embodiments, the extrusion and spheronization of a mixture of centanafadine or a pharmaceutically acceptable salt thereof with an excipient as disclosed herein can provide a high drug load (e.g., 80 wt. % based on the total weight of the core particle) with a low total weight of the core particle, therefore decreasing the overall "footprint" of the drug because of less usage of added excipients that do not have the desired pharmacological impact on the subject. In embodiments, the extrusion and spheronization of a mixture of centanafadine or a pharmaceutically acceptable salt thereof with an excipient as disclosed herein can provide a facile way to change the particle size distribution with the same amounts of API and excipients by the use of a different extrusion screen. In embodiments, the extrusion and spheronization of a mixture of centanafadine or a pharmaceutically acceptable salt thereof with an excipient as disclosed herein can provide a uniform dissolution of the drug product because of the uniformity of the coating weight gain disposed over the core particle. In embodiments, the extrusion and spheronization of a mixture of centanafadine or a pharmaceutically acceptable salt thereof with an excipient as disclosed herein can provide a formulation for use with pediatrics.

As described above in connection with description of the core particles, the method can include a step of sorting (e.g., by sieving) the core particles prior to coating, to retain particles in a predetermined size range, for example sizes in a range of about 0.2 mm to about 2.8 mm, or about 0.2 mm to about 2.5 mm, or about 0.2 mm to about 1.7 mm, or about 0.5 mm to about 0.71 mm, or any range described above in connection with the core particles.

In an extrusion and spheronization process, the following optional features can be employed, individually or in one or more combinations thereof. Water can be used as a granulation agent. Microcrystalline cellulose can be used in the core particles as a spheronization aid. Low-substituted hydroxypropylcellulose is also known as a spheronization aid.

In embodiments, the method can further include coating the dried core particles. In embodiments, the coating can be applied using a fluid bed processor. In embodiments, required quantity of the coating dispersion/solution is sprayed using Wurster process at a controlled set of process parameters.

The beads and/or filled capsules can be stored with a desiccant. The beads and/or filled capsules can be stored with an oxygen absorber.

A coating process, such as a seal coating process can be carried out using a fluid bed processor. A seal coating is optional. In the description herein, generally when a bead is coated the uncoated portion of the bead is referred to as a bead core; however uncoated bead cores can also be regarded as beads themselves. In the Examples described below, 80 wt. % active CTN bead cores were seal coated before subsequent coating with SR and DR coatings, while 10 wt. % and 50 wt. % active CTN beads were not coated in those Examples. The desired quantity of the coating dispersion/solution can be sprayed using a Wurster process at a controlled set of process parameters, and then coated beads can be dried to a desired moisture content, and heat cured if desired. A seal coating polymer can be selected from any material which does not substantially affect the release properties of the active from the beads, and preferably which provides the bead cores with a smooth outer surface once coated. Examples of suitable materials include hydrophilic polymers, e.g. hydrophilic cellulose ethers, e.g. hydroxypropyl methylcellulose, and hydroxypropylcellulose. Other polymers include polyvinylpyrrolidone, and polyethylene glycol (PEG), in particular polyethylene glycol 20000.

Application of sustained release and delayed release coatings can be carried out using a fluid bed processor, e.g. to a desired coating weight by weight gain. In such a process, the required quantity of the coating dispersion/solution is sprayed using Wurster process at a controlled set of process parameters. Coated beads can then be dried to a desired moisture content, and heat cured if desired.

Depending on the desired product strength, quantities of one or more regions or formulation types, e.g. immediate release regions (e.g. 10% or 50% beads) along with SR and/or DR regions (e.g. SR-coated beads and DR coated beads) can be packaged, e.g. by encapsulation into appropriate capsule shells using multi-bead filling and encapsulating machines. In one type of embodiment, the plurality of CTN beads can be enclosed in a capsule shell. In embodiments, an automatic encapsulating machine is used to enclose the plurality of CTN beads in a capsule shell. In embodiments, the encapsulation process involves filling of one or more bead types selected from immediate release beads, sustained release beads and delayed release beads sequentially with appropriate filled weight controls, as desired. After the bead components are filled, capsules are closed to desired capsule height.

For example, one embodiment of the method combining various of the parameters described above includes a method for the preparation of a pharmaceutical dosage form including CTN beads, including forming a wet mass comprising CTN and an excipient, optionally microcrystalline cellulose, extruding and spheronizing the wet mass including CTN and excipient to make core particles, sorting the core particles to a target particle size range, optionally 0.7 mm to 2.5 mm, optionally coating the sorted core particles with a polymer to form beads comprising a core particle and a release membrane thereon, and sorting the bead particles to a target particle size range, optionally 0.7 mm to 2.5 mm.

Method of Treatments/Use

Also provided herein are methods of treatment using a formulation or dosage form according to the description herein, or use of a formulation or dosage form according to the description herein, comprising administering an effective amount of a formulation or dosage form according to the description herein to an animal subject in need thereof. In embodiments, the animal subject is a mammalian subject in need thereof. In embodiments, the mammalian subject is a human in need thereof. The formulation or dosage form can be administered together with one or more additional psychotherapeutic agents. The one or more additional psychotherapeutic agents can be administered separately, or incorporated into the formulation or dosage form described herein. The one or more additional psychotherapeutic agents can be administered concomitantly with CTN, or on a different frequency or dosage schedule.

The formulation or dosage form can be administered to an animal, e.g. a mammalian subject, for example a human patient, to inhibit norepinephrine reuptake, and/or dopamine reuptake, and/or serotonin reuptake. The formulation or dosage form can be administered to an animal, e.g. a mammalian subject, for example a human patient, to treat or prevent one or more symptoms of a disorder alleviated by inhibiting norepinephrine reuptake, and/or dopamine reuptake, and/or serotonin reuptake. In certain embodiments, "treatment" or "treating" refers to amelioration of one or more symptoms of a disorder, whereby the symptom(s) is/are alleviated by inhibiting dopamine and/or norepinephrine and/or serotonin reuptake. In other embodiments, "treatment" or "treating" refers to an amelioration of at least one measurable physical parameter associated with a disorder. In yet another embodiment, "treatment" or "treating" refers to inhibiting or reducing the progression or severity of a disorder (or one or more symptoms thereof) alleviated by inhibiting dopamine and/or norepinephrine and/or serotonin reuptake, e.g., as discerned based on physical, physiological, and/or psychological parameters. A formulation or dosage form as described herein optionally can be used for delaying the onset of a disorder (or one or more symptoms thereof) by inhibiting norepinephrine and/or dopamine and/or serotonin reuptake.

An "effective amount," "therapeutic amount," "therapeutically effective amount," or "effective dose" of a formulation or dosage form as described herein, and/or an additional psychotherapeutic agent as used herein, means an effective amount or dose of the active compound as described herein sufficient to elicit a desired pharmacological or therapeutic effect in a subject, e.g. a human subject. In the case of therapeutic agents for ADHD or substance abuse, these terms most often refer to a significant reduction in an occurrence, frequency, or severity of one or more symptoms of a specified disorder, including any combination of neurological and/or psychological symptoms, diseases, or conditions, associated with or caused by the targeted disorder.

A formulation or dosage form herein can be administered, or labeled for administration in an amount based on the subject's body weight. A formulation or dosage form herein can be administered, or labeled for administration in an amount of CTN in a range of 0.5 mg/kg to 20 mg/kg per day, e.g., 1 mg/kg to 15 mg/kg per day, e.g., 1 mg/kg to mg/kg per day, e.g., 2 mg/kg to 20 mg/kg per day, e.g., 2 mg/kg to 10 mg/kg per day, e.g., 3 mg/kg to 15 mg/kg per day, or about 1.5 mg/kg per day of CTN or pharmaceutically acceptable salt thereof (e.g. HCl salt). Embodiments can include about 1.43 mg/kg to 5.71 mg/kg per day, about 2.86 mg/kg to 5.71 mg/kg per day, about 1.5 mg/kg to about 6 mg/kg per day, or about 3 mg/kg to 6 mg/kg per day. The administration can be in divided doses, if desired. In another aspect, a formulation or dosage form described herein can include the CTN or pharmaceutically acceptable salt thereof (e.g. HCl salt) in an amount in a range of about 10 to about 25 mg, or about 30 mg to about 50 mg, or about 25 mg to about 150 mg, or about 50 mg to about 100 mg, or about 100 to about 250 mg, or about 250 to about 500 mg, administered (or labeled for administration) one, two, three, or four times per day. Dosages of about 50-75 mg, about 100-200 mg, about 250-400 mg, or about 400-600 mg can be administered, or labeled for administration, once or twice daily. Dosages of about 100-300 mg can be administered, or labeled for administration, once daily. Dosages of about 100-300 mg can be administered, or labeled for administration, once daily in the morning. Dosages of about 40-330 mg can be administered, or labeled for administration, once daily. Dosages of about 40-330 mg can be administered, or labeled for administration, once daily in the morning. Particular dosage form amounts can include 41.1 mg, 82.2 mg, 123.3 mg, 164.4 mg, 246.6 mg, and 328.8 mg.

A subject weighing less than 20 kg can be started on a CTN dose of 41.1 mg per day. A subject weighing from 20 kg to less than 35 kg can be started on a dose of 82.2 mg per day. A subject weighing from 35 kg to 50 kg can be started on a dose of 123.3 mg per day. A subject weighing more than 50 kg can be started on a dose of 164.4 mg. Dosing can be increased in increments of 25%, or 50%, or 75%, or 100% of the initial dose amount. For example, a subject receiving an initial dose of 164.4 mg/day can be increased by an amount of 41.1 mg for an subsequent ongoing dose of 205.5 mg/day unless further increases are made; in another aspect the increase can be by 82.2 mg; in another aspect the increase can be by 123.3 mg, or in another aspect the increase can be by 164.4 mg/day.

A formulation or dosage form described herein can be used in treating a variety of conditions including attention-deficit/hyperactivity disorder (ADHD), Major Depressive Disorders, smoking and nicotine dependence, and binge eating disorder, for example.

ADHD is distinguished by symptoms of difficulty staying focused and paying attention, difficulty controlling behavior, impulsivity, disorganization, and hyperactivity (over-activity). ADHD is diagnosed in both children and adults based on criteria described in the Diagnostic and Statistical Manual of Mental Disorders, Fourth Edition (2000), Text Revision (DSM-IV-TR), American Psychiatric Association, Washington, D.C. The DSM-IV-TR criteria describe three subtypes of ADHD: Attention Deficit Hyperactivity Disorder-predominantly hyperactive-impulsive subtype; Attention Deficit Hyperactivity Disorder-predominantly inattentive subtype (also referred as Attention Deficit Disorder or ADD); and Attention Deficit Hyperactivity Disorder-combined subtype. In the predominantly inattentive type, a person can have six or more of the following disruptive and age-inappropriate symptoms: difficulty paying attention to details, difficulty keeping attention on tasks, difficulty following instructions, difficulty organizing activities, difficulty following conversations, being easily distracted, and forgetful of daily routines. In the predominantly hyperactive-impulsive type, a person can have six or more of the following disruptive and age-inappropriate symptoms: fidgeting often, inappropriate running about, trouble playing or enjoying leisure activities quietly, excessive talking, blurting out answers, trouble waiting turn, and interrupting others. In the combined type, both inattentive and hyperactive-impulsive behaviors can be present. (1R,5S)-1-(naphthalen-2-yl)-3-azabicyclo[3.1.0]hexane or a pharmaceutically acceptable salt thereof is effective in treating all subtypes of ADHD, both in adult and pediatric ADHD. (1R,5S)-1-(naphthalen-2-yl)-3-azabicyclo[3.1.0]hexane or a pharmaceutically acceptable salt thereof is likewise effective in treating ADHD allied disorders, such as Attention-Deficit/Hyperactivity Disorder not otherwise specified (NOS); Conduct Disorder; Oppositional Defiant Disorder; and Disruptive Behavior Disorder not otherwise specified (NOS).

A formulation or dosage form described herein can be used in treating an autism spectrum disorder in a patient having a fragile X-associated disorder. As used herein, "autism spectrum disorder," includes autistic disorder (classic autism), Asperger's disorder (Asperger syndrome), pervasive developmental disorder not otherwise specified (PDD-NOS), Rett® disorder (Rett syndrome), and childhood disintegrative disorder (CDD).

A formulation or dosage form described herein can be used in treating a fragile X-associated disorder. Fragile X-associated disorders are a family of genetic conditions that may affect individuals in a variety of ways. The three fragile X-associated disorders are fragile X syndrome (FXS), fragile X-associated tremor/ataxia syndrome (FX-TAS), and fragile X-associated primary ovarian insufficiency (FXPOI). The conditions are all caused by changes in the fragile X mental retardation 1 (FMR1) gene, located on the X chromosome.

A formulation or dosage form described herein can be used in treating a binge eating disorder. Binge eating disorder involves recurrent episodes of binge eating. A binge-eating episode may encompass eating, in a discrete period of time (e.g., within any 2-hour period), an amount of food that is larger than most people would eat during a similar period of time and under similar circumstances and a sense of lack of control over eating during the episode (e.g., a feeling that one cannot stop eating or control what or how much one is eating). A binge-eating episode may also encompass three (or more) of the following: eating much more rapidly than normal, eating until feeling uncomfortably full, eating large amounts of food when not feeling physically hungry, eating alone because of being embarrassed by how much one is eating, and feeling disgusted with oneself, depressed, or very guilty after overeating. Binge eating disorder may also encompass marked distress regarding binge eating. Binge eating may occur, on average, at least once a week for three months. Binge eating is not associated with the recurrent use of inappropriate compensatory behavior (for example, purging).

The formulations, dosage forms and related methods described herein can be used in mammalian subjects, for example a human patient, to treat or prevent one or more symptom(s) of a CNS disorder alleviated by inhibiting dopamine reuptake, and/or norepinephrine reuptake, and/or serotonin reuptake. In embodiments, "treatment" or "treating" can refer to amelioration of one or more symptom(s) of a CNS disorder, whereby the symptom(s) is/are alleviated by inhibiting dopamine and/or norepinephrine and/or serotonin reuptake. In other embodiments, "treatment" or "treating" can refer to an amelioration of at least one measurable physical parameter associated with a CNS disorder. In yet another embodiment, "treatment" or "treating" can refer to inhibiting or reducing the progression or severity of a CNS disorder (or one or more symptom(s) thereof) alleviated by inhibiting dopamine and/or norepinephrine and/or serotonin reuptake, e.g., as discerned based on physical, physiological, and/or psychological parameters. In additional embodiments, "treatment" or "treating" refers to delaying the onset of a CNS disorder (or one or more symptom(s) thereof) alleviated by inhibiting dopamine and/or norepinephrine and/or serotonin reuptake.

The formulations, dosage forms and related methods described herein can be used in a mammalian subject, for example a human patient, as a preventative or prophylactic treatment against a CNS disorder (or one or more symptom(s) thereof) alleviated by inhibiting dopamine and/or norepinephrine and/or serotonin reuptake. As used herein, "prevention", "preventing", and prophylaxis can refer to a reduction in the risk or likelihood that the subject will acquire a CNS disorder or one or more symptom(s) thereof, which risk or likelihood is reduced in the subject by inhibiting dopamine and/or norepinephrine and/or serotonin reuptake. Alternatively, prevention and prophylaxis can correlate with a reduced risk of recurrence of the CNS disorder or symptom(s) thereof in the subject once the subject has been cured, restored to a normal state, or placed in remission from the subject CNS disorder. Formulations, dosage forms and related methods described herein can be used as a preventative measure to the subject. Subjects amenable to prophylactic treatment in this context can have a genetic predisposition to a CNS disorder amenable to treatment by inhibiting dopamine, and/or serotonin, and/or norepinephrine reuptake, such as a family history of a biochemical imbalance in the brain, or a non-genetic predisposition to a disorder alleviated by inhibiting dopamine and/or norepinephrine and/or serotonin reuptake.

The formulations, dosage forms and related methods described herein can be used for treating or preventing endogenous disorders alleviated by inhibiting dopamine and/or norepinephrine and/or serotonin reuptake. Such disorders include, but are not limited to, attention-deficit disorder, depression, anxiety, obesity, Parkinson® disease, tic disorders, and addictive disorders.

Disorders alleviated by inhibiting dopamine and/or norepinephrine and/or serotonin reuptake are not limited to the specific disorders described herein, and the formulations, dosage forms and related methods described herein will be understood or readily ascertained to provide effective treatment agents for treating and/or preventing a wide range of additional CNS disorders and associated symptoms. For example, the formulations, dosage forms and related methods described herein can provide promising candidates for treatment and/or prevention of attention deficit hyperactivity disorder and related symptoms, as well as forms and symptoms of alcohol abuse, drug abuse, obsessive compulsive behaviors, learning disorders, reading problems, gambling addiction, manic symptoms, phobias, panic attacks, oppositional defiant behavior, conduct disorder, academic problems in school, smoking, abnormal sexual behaviors, schizoid behaviors, somatization, depression, sleep disorders, general anxiety, stuttering, and tic disorders (see for example, U.S. Pat. No. 6,132,724). These and other symptoms, regardless of the underlying CNS disorder, are each prospective therapeutic targets for the formulations, dosage forms and related methods that mediate therapeutic benefits by inhibiting dopamine and/or norepinephrine and/or serotonin reuptake. Additional CNS disorders contemplated for treatment employing the formulations, dosage forms and related methods described herein are described, for example, in the Quick Reference to the Diagnostic Criteria From DSM-IV (Diagnostic and Statistical Manual of Mental Disorders, Fourth Edition), The American Psychiatric Association, Washington, D.C., 1994. These target disorders for treatment and/or prevention according to the invention, include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders amenable for treatment and/or prevention with the formulations, dosage forms and related methods described herein include, but are not limited to, Major Depressive Disorder, Recurrent; Dysthymic Disorder; Depressive Disorder not otherwise specified (NOS); and Major Depressive Disorder, Single Episode.

Addictive disorders amenable for treatment and/or prevention employing the formulations, dosage forms and related methods described herein include, but are not limited to, eating disorders, impulse control disorders, alcohol-related disorders, nicotine-related disorders, amphetamine-related disorders, cannabis-related disorders, cocaine-related disorders, hallucinogen use disorders, inhalant-related disorders, and opioid-related disorders, all of which are further sub-classified as listed below.

Eating disorders include, but are not limited to, Bulimia Nervosa, Nonpurging Type; Bulimia Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder, with delusions; Alcohol Abuse; Alcohol Intoxication; Alcohol Withdrawal; Alcohol Intoxication Delirium; Alcohol Withdrawal Delirium; Alcohol-Induced Persisting Dementia; Alcohol-Induced Persisting Amnestic Disorder; Alcohol Dependence; Alcohol-Induced Psychotic Disorder, with hallucinations; Alcohol-Induced Mood Disorder; Alcohol-Induced Anxiety Disorder; Alcohol-Induced Sexual Dysfunction; Alcohol-Induced Sleep Disorders; Alcohol-Related Disorders not otherwise specified (NOS); Alcohol Intoxication; and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

Cannabis-related disorders include, but are not limited to, Cannabis Dependence; Cannabis Abuse; Cannabis Intoxication; Cannabis Intoxication Delirium; Cannabis-Induced Psychotic Disorder, with delusions; Cannabis-Induced Psychotic Disorder with hallucinations; Cannabis-Induced Anxiety Disorder; Cannabis Related Disorder not otherwise specified (NOS); and Cannabis Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

Tic disorders include, but are not limited to, Tourette® Disorder, Chronic Motor or Vocal Tic Disorder, Transient Tic Disorder, Tic Disorder not otherwise specified (NOS), Stuttering, Autistic Disorder, and Somatization Disorder.

By virtue of their multiple reuptake inhibitory activity, the formulations, dosage forms and related methods described herein are thus useful in a wide range of veterinary and human medical applications, in particular for treating and/or preventing a wide array of CNS disorders and/or associated symptom(s) alleviated by inhibiting dopamine and/or norepinephrine and/or serotonin reuptake.

Disorders which can be alleviated by use of a formulation or dosage form as described herein are not limited to the specific disorders described herein, and will be understood or readily ascertained to provide effective agents for treating and/or preventing a wide range of additional disorders and associated symptoms. For example, the formulation or dosage form as described herein will provide promising candidates for treatment and/or prevention of cognitive disorders, bipolar disorder, anorexia nervosa, bulimia nervosa, cyclothymic disorder, chronic fatigue syndrome, chronic or acute stress, learning disorders, reading problems, gambling addiction, manic symptoms, phobias, panic attacks, academic problems in school, smoking, abnormal sexual behaviors, schizoid behaviors, sleep disorders, stuttering, fibromyalgia and other somatoform disorders (including somatization disorder, conversion disorder, pain disorder, hypochondriasis, body dysmorphic disorder, undifferentiated somatoform disorder, and somatoform NOS, incontinence (i.e., stress incontinence, genuine stress incontinence, and mixed incontinence), inhalation disorders, mania, migraine headaches, and peripheral neuropathy. The formulation or dosage form described herein can be used in treating or preventing any one of the disorders or indications described in U.S. Pat. Nos. 8,461,196, 9,839,627, or U.S. Patent Application Publication Nos. 2018/0008575A and 2014/0206740A, the contents of each of which are hereby incorporated by reference.

Various aspects of the pharmaceutical formulations, methods of treatments, and uses are described below using enumerated Aspects.

Aspect A

A1. A pharmaceutical formulation comprising a plurality of centanafadine (CTN) beads, the plurality of CTN beads each comprising a core particle comprising CTN or a pharmaceutically acceptable salt thereof and an excipient.

A2. The pharmaceutical formulation of A1, wherein at least a portion of the plurality of beads is coated.

A3. The pharmaceutical formulation of any one of A1-A2, wherein at least a portion of the plurality of beads is not coated.

A4. The pharmaceutical formulation of A2, wherein the coating is one or more coatings selected from a delayed release coating, a sustained release coating, and a delayed-sustained release coating.

A5. The pharmaceutical formulation of A4, wherein the coating is a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer;

optionally one or more materials selected from a copolymer of methacrylic acid, methyl methacrylate, and methyl acrylate, and a methacrylic acid-acrylate copolymer; and optionally a copolymer of methacrylic acid, methyl methacrylate, and methyl acrylate.

A6. The pharmaceutical formulation of any one of A1-A5 comprising a delayed release coating, wherein the median amount of delayed release coating disposed over the core particle is at least 10 wt. % of the total weight of the CTN bead, or in a range of about 12 wt. % to about 50 wt. %, or about 12 wt. % to about 35 wt. %, or about 15 wt. % to about 45 wt. %, based on the total weight of the CTN bead;

or in a range of about 10 wt. % to about 50 wt. %, or about 10 wt. % to about 40 wt. %, or about 10 wt. % to about 30 wt. %, or about 20 wt. %, based on the total weight of the CTN bead.

A7. The pharmaceutical formulation of any one of A1-A6 comprising a sustained release coating, wherein the sustained release coating comprises one or more materials selected from an alkylcellulose, acrylic acid polymer, a methacrylic acid polymer, an acrylic acid copolymer, a methacrylic acid copolymer, and a cellulose ether;

optionally one or more materials selected from a hydroxyalkylcellulose, a carboxyalkylcellulose, an ethylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, an aqueous dispersion of a neutral copolymer based on ethyl acrylate and methacrylate of approximately 30% polymer content [CAS 9010-88-4], a poly(acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer;

optionally one or more materials selected from poly[ethyl acrylate, methyl methacrylate, trimethylammonioethyl methacrylate chloride], hydroxypropylmethylcellulose, and poly[ethyl acrylate, methyl methacrylate];

optionally poly[ethyl acrylate, methyl methacrylate].

A8. The pharmaceutical formulation of any one of A1-A7 comprising a sustained release coating, wherein the median amount of sustained release coating disposed over the core particle is at least 5 wt. % of the total weight of the core particle, or in a range of about 5 wt. % to about 60 wt. %, or about 15 wt. % to about 60 wt. %, or about 20 wt. % to about 50 wt. % of the total weight of the core particle;

or in a range of about 5 wt. % to about 50 wt. %, or about 7.5 wt. % to about 45 wt. %, or about 10 wt. % to about 40 wt. %, or about 15 wt. %, of the total weight of the core particle;

or in a range of about 5 wt. % to about 40 wt. %, about 15 wt. % to about 40 wt. %, or about 20 wt. % to about 40 wt. %, of the total weight of the core particle.

A9. The pharmaceutical formulation of any one of A1-A8 comprising a coating, wherein the coating further comprises a pore former.

A10. The pharmaceutical formulation of A9, wherein the pore former comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide, optionally one or more materials selected from hydroxypropyl methylcellulose, hydroxypropylcellulose, and polyvinylpyrrolidone;

optionally hydroxypropyl methylcellulose.

A11. The pharmaceutical formulation of A9, wherein the pore former is present in the coating in an amount in a range of about 5 wt. % or more, or about 10 wt. % or more, or about 5 wt. % to about 20 wt. %; optionally 15 wt. %;

or less than 50 wt. % or less than 20 wt. %% or in a range of about 1 wt. % to about 16 wt. %, or about 1 wt. % to about 12 wt. %, based on the total weight of the coating.

A12. The pharmaceutical formulation of any one of the A1-A11, wherein the core particles are characterized by having a distribution of particles sizes, and at least a portion of the core particles of the plurality of beads have a core particle size (maximum diameter) of about 0.2 mm to about 2 mm, or about 0.3 mm to about 1.5 mm, 0.4 mm to about 1.5 mm, or about 0.5 mm to about 1 mm, or about 0.5 mm to 0.85 mm, or about 0.5 mm to about 0.71 mm.

A13. The pharmaceutical formulation of A12, wherein the distribution of particles sizes of the core particles is characterized by at least 60% by weight of the core particles having a particle size (maximum diameter) in a range of about 0.4 mm to about 1.5 mm, or about 0.5 mm to about 1 mm, or about 0.5 mm to 0.85 mm, or about 0.5 mm to about 0.71 mm, optionally at least 80% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 90% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 99% by weight of the core particles having a particle size in a range of about 0.4 mm to about 1.5 mm, or about 0.5 mm to about 1 mm, or about 0.5 mm to 0.85 mm, or about 0.5 mm to about 0.71 mm.

A14. The pharmaceutical dosage form of any one of A1-A13, wherein the plurality of CTN beads have a median particle size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm.

A15. The pharmaceutical formulation of any one of A1-A14, wherein the plurality of CTN beads comprises one or more types selected from: an immediate release bead, a sustained release bead, a delayed release bead, and a delayed-sustained release bead.

A16. The pharmaceutical formulation of any one of A1-A15, wherein the plurality of beads comprises a mixture of one or more immediate release beads and one or more sustained release beads.

A17. The pharmaceutical formulation of A16, wherein the ratio of CTN or pharmaceutically acceptable salt thereof is present in the one or more immediate release beads and one or more sustained release beads at a ratio in a range of about 1:100 to about 1:1 parts by weight based on the weight of CTN.

A18. The pharmaceutical formulation of any one of A1-A17, wherein the plurality of beads comprises a mixture of one or more immediate release beads and one or more delayed release beads.

A19. The pharmaceutical formulation of A18, wherein the ratio of CTN or pharmaceutically acceptable salt thereof is present in the one or more immediate release beads and one or more delayed release beads at a ratio in a range of about 1:100 to about 1:1 parts by weight based on the weight of CTN.

A20. The pharmaceutical formulation of any one of A1-A19, wherein the plurality of beads comprises a mixture of one or more delayed release beads and one or more sustained release beads.

A21. The pharmaceutical formulation of A20, wherein the ratio of CTN or pharmaceutically acceptable salt thereof is present in the one or more sustained release beads and one or more delayed release beads at a ratio in a range of about 5:10 to about 1:5 parts by weight based on the weight of CTN.

A22. The pharmaceutical formulation of any one of A1-A21, wherein the plurality of beads comprises a mixture of one or more immediate release beads and one or more delayed-sustained release beads.

A23. The pharmaceutical formulation of A22, wherein the ratio of CTN or pharmaceutically acceptable salt thereof is present in the one or more immediate release beads and one or more delayed-sustained release beads at a ratio in a range of about 1:100 to about 1:1 parts by weight based on the weight of CTN.

A24. The pharmaceutical formulation of any one of A1-A23, wherein the plurality of beads comprises a mixture of one or more immediate release beads, one or more sustained release beads, and one or more delayed release beads.

A25. The pharmaceutical formulation of A24, wherein the ratio of CTN or pharmaceutically acceptable salt thereof is present in the one or more immediate release beads, one or more sustained release beads, and one or more delayed release beads at a ratio in a range of about 0.1-1:1-20:1-20 parts by weight based on the weight of the CTN or salt thereof;
    optionally a ratio in a range of about 0.5-1:5-20:5-20 parts by weight based on the weight of the CTN or salt thereof;
    optionally a ratio in a range of about 0.7-13:3-6:3-6 parts by weight based on the weight of the CTN or salt thereof; and,
    optionally a ratio in a range of about 0.7-1:5-15:5-15 parts by weight based on the weight of the CTN or salt thereof.

A26. The pharmaceutical formulation of any one of A1-A25, wherein the plurality of beads comprises a mixture of one or more immediate release beads, one or more sustained release beads, and one or more delayed-sustained release beads.

A27. The pharmaceutical formulation of A26, wherein the ratio of CTN or pharmaceutically acceptable salt thereof is present in the one or more immediate release beads, one or more sustained release beads, and one or more delayed-sustained release beads at a ratio in a range of about 0.1-1:1-20:1-20 parts by weight based on the weight of the CTN or salt thereof;
    optionally a ratio in a range of about 0.5-1:5-20:5-20 parts by weight based on the weight of the CTN or salt thereof;
    optionally a ratio in a range of about 0.7-13:3-6:3-6 parts by weight based on the weight of the CTN or salt thereof; and,
    optionally a ratio in a range of about 0.7-1:5-15:5-15 parts by weight based on the weight of the CTN or salt thereof.

A28. The pharmaceutical formulation of any one of A1-A27, wherein the immediate release bead is free of coatings.

A29. The pharmaceutical formulation of any one of A1-A28, wherein the immediate release beads are present in the formulation in an amount in a range of about 1% to about 75% based on the total weight of the plurality of CTN beads,
    optionally in a range of about 40% to about 50% based on the total weight of the plurality of CTN beads when the drug loading in the immediate release beads is about 5 wt. % to about wt. %;
    optionally in a range of about 1% to about 50% based on the total weight of the plurality of CTN beads;
    optionally in a range of about 1% to about 25% based on the total weight of the plurality of CTN beads;
    optionally in a range of about 1% to about 10% based on the total weight of the plurality of CTN beads
    optionally in a range of about 9% to about 19% based on the total weight of the plurality of CTN beads when the drug loading in the immediate release beads is about 40 wt. % to about wt. %; and
    optionally in a range of about 18% to about 28% based on the total weight of the plurality of CTN beads.

A30. The pharmaceutical formulation of any one of A1-A29 comprising sustained release beads, wherein the sustained release beads are present in the formulation in an amount in a range of about 5% to 80% based on the total weight of the plurality of CTN beads;
    optionally in a range of about 23% to about 33% based on the total weight of the plurality of CTN beads;
    optionally in a range of about 5% to about 65% based on the total weight of the plurality of CTN beads;
    optionally in a range of about 40% to about 50% based on the total weight of the plurality of CTN beads;
    optionally in a range of about 35% to about 55% based on the total weight of the plurality of CTN beads.

A31. The pharmaceutical formulation of any one of A1-A30 comprising delayed release beads, wherein the delayed release beads are present in the formulation in an amount in a range of about 5% to 80% based on the total weight of the plurality of CTN beads;
    optionally in a range of about 21% to about 31% based on the total weight of the plurality of CTN beads;

optionally in a range of about 5% to about 65% based on the total weight of the plurality of CTN beads;

optionally in a range of about 36% to about 46% based on the total weight of the plurality of CTN beads;

optionally in a range of about 30% to about 55% based on the total weight of the plurality of CTN beads.

A32. The pharmaceutical formulation of any one of A1-A31 comprising sustained release beads, wherein at least 90% of the CTN or salt thereof is released from the sustained release beads at a time in a range of 2 to 6 hours according to USP <711> using Apparatus I (basket) in 1000 ml deionized water at 37° C.+/−0.5° C. at 100 rpm.

A33. The pharmaceutical formulation of any one of A1-A32 comprising delayed release beads, wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

A34. The pharmaceutical formulation of any one of A1-A33 comprising delayed-sustained release beads, wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

A35. The pharmaceutical formulation of any one of A1-A34 comprising immediate release beads, wherein at least 90% of the CTN or salt thereof is released from the immediate release beads at a time in a range of 0 to 2 hours according to USP <711> using Apparatus I (basket) in 1000 ml deionized water at 37° C.+/−0.5° C. at 100 rpm.

A36. The pharmaceutical formulation of any one of A1-A35 comprising a mixture of immediate release beads, sustained release beads, and delayed release beads, wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

A37. The pharmaceutical formulation of any one of A1-A35 comprising a mixture of immediate release beads, sustained release beads, and delayed release beads, wherein according to USP <711> using Apparatus I (basket) in 1000 mL 0.1N hydrochloric acid at 37° C.+/−0.5° C. at 100 rpm for 2 hours, followed by Apparatus I (basket) in 1000 mL pH 7.4 phosphate buffer solution at 37° C.+/−0.5° C.) at 100 rpm for 12 the release profile characterized by:

(a) release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points; and/or (b) release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points and still further optionally, the release profile can be characterized by a release of 49% to 73% at the 4-hour mark.

A38. The pharmaceutical formulation of any one of A1-A37 comprising an immediate release bead, wherein the CTN or salt thereof is present in an amount in a range of 5 wt. % to 80 wt. % in the immediate release bead based on the total weight of the immediate release bead;

optionally in a range of 5 wt. % to 60 wt. % based on the total weight of the immediate release bead;

optionally in a range of 5 wt. % to 15 wt. % based on the total weight of the immediate release bead;

optionally in a range of 40 wt. % to 60 wt. % based on the total weight of the immediate release bead; and optionally a first immediate release bead wherein the CTN or salt thereof is present in an amount in a range of 5 wt. % to 15 wt. % based on the total weight of the immediate release bead and a second immediate release bead wherein the CTN or salt thereof is present in an amount in a range of 40 wt. % to 60 wt. % based on the total weight of the immediate release bead.

A39. The pharmaceutical formulation of any one of A1-A38 comprising a sustained release bead, wherein the CTN or salt thereof is present in an amount in a range of 10 wt. % to 95 wt. % in the sustained release bead based on the total weight of the sustained release bead;

optionally in a range of 40 wt. % to 90 wt. % based on the total weight of the sustained release bead;

optionally in a range of 50 wt. % to 70 wt. % based on the total weight of the sustained release bead.

A40. The pharmaceutical formulation of any one of A1-A39 comprising a delayed release bead, wherein the CTN or salt thereof is present in an amount in a range of 10 wt. % to 95 wt. % in the delayed release bead based on the total weight of the delayed release bead;

optionally in a range of 40 wt. % to 90 wt. % based on the total weight of the delayed release bead;

optionally in a range of 50 wt. % to 70 wt. % based on the total weight of the delayed release bead.

A41. The pharmaceutical formulation of any one of A1-A40, characterized by providing an in vivo absorption profile that is multimodal, optionally bimodal.

A42. The pharmaceutical formulation of any one of A1-A41, wherein the in vivo absorption profile has a first $C_{max}$ at a time in a range of 0 to 4.5 hours, or about 0.5 hours to about 2 hours, or about 3.5 hours to about 4.5 hours.

A43. The pharmaceutical formulation of any one of A1-A42, wherein the in vivo absorption profile has a second $C_{max}$ at a time in a range of about 6 hours to 10 hours, or about 7 hours to 9 hours, or about 7.5 to about 8.5 hours.

A44. The pharmaceutical formulation of any one of A42 or A43, wherein the first $C_{max}$ provided by the formulation in adult humans has an average plasma level in a range of about 250 ng/mL to about 420 ng/mL, or about 320 ng/mL to about 420 ng/mL, or about 325 ng/mL to about 390 ng/mL.

A45. The pharmaceutical formulation of any one of A42-A44, wherein the second $C_{max}$ provided by the formulation in adult humans has an average plasma level in a range of about 450 ng/mL to about 550 ng/mL, or about 470 ng/mL to about 530 ng/mL.

A46. The pharmaceutical formulation of any one of A1-A45, wherein the in vivo absorption profile has a first $C_{max}$ and a second $C_{max}$, wherein the first $C_{max}$ and second $C_{max}$ are separated by a time in a range of 1.5 to 8.5 hours, or about 2 hours to about 6 hours, or about 3 hours to about 5 hours.

A47. The pharmaceutical formulation of any one of A1-A46, wherein one or more of the plurality of CTN beads has a release mechanism comprising one or more of dissolution, diffusion, erosion, osmosis, partitioning, swelling, and targeting.

A48. The pharmaceutical formulation of any one of A1-A47, wherein one or more of the plurality of CTN beads has a diffusion release mechanism.

A49. The pharmaceutical formulation of any one of A1-A48, wherein one or more of the plurality of CTN beads has a pH-triggered dissolution release mechanism.

A50. The pharmaceutical formulation of any one of A1-A49, wherein one or more of the plurality of CTN beads has a combination of pH-triggered dissolution release mechanism and diffusion release mechanism.

A51. The pharmaceutical formulation of any one of A1-A50, wherein one or more of the plurality of CTN beads comprises a porous matrix comprising the CTN.

A52. The pharmaceutical formulation of any one of A1-A51, wherein the plurality of CTN beads are enclosed in one or more containers selected from a capsule, sachet, and stick-pack;
optionally a capsule.

A53. The pharmaceutical formulation of any one of A1-A52, wherein the CTN is present as a salt; optionally as a hydrochloride salt.

A54. The pharmaceutical formulation of any one of A1-A53, wherein the excipient comprises one or more materials selected from a filler and a binder, a glidant, a surfactant, a polymer coating, and a plasticizer;
optionally a combination of a filler and a binder;
optionally a combination of a binder and a polymer coating;
optionally a combination of a filler, a binder, and a polymer coating;
optionally a combination of a filler, a binder, a polymer coating, and a plasticizer.

A55. The pharmaceutical formulation of any one of A1-A54, wherein the excipient comprises one or more materials selected from lactose, mannitol, corn starch, microcrystalline cellulose, hydroxypropyl cellulose, hypromellose, polyvinyl pyrrolidone, talc, polysorbate 80, glycerol monostearate, triethyl citrate, polyvinyl alcohol-polyethylene glycol graft copolymer, and silica.

A56. The pharmaceutical formulation of any one of A1-A55, wherein the formulation is free of disintegrants.

Aspect B

B1. A pharmaceutical formulation comprising CTN or a pharmaceutically acceptable salt thereof, wherein the formulation is a solid oral formulation suitable for pediatric use.

B2. The pharmaceutical formulation of B1, wherein the solid oral formulation suitable for pediatric use is selected from one or more types comprising beads, orodispersible tablet, orodispersible film, mini-tablet, chewable tablet, and soft-chew, optionally beads.

B3. The pharmaceutical formulation of any one of B1 or B2, wherein the solid oral formulation suitable for pediatric use is characterized by one or more release profiles, in vivo and/or in vitro, selected from immediate release, sustained release, delayed release, and delayed-sustained release.

B4. The pharmaceutical formulation of any one of B1-B3, wherein the solid oral formulation suitable for pediatric use comprises a plurality of centanafadine (CTN) beads, the plurality of CTN beads each comprising a core particle comprising CTN or a pharmaceutically acceptable salt thereof and an excipient.

B5. The pharmaceutical formulation of B4, wherein at least a portion of the plurality of beads are coated.

B6. The pharmaceutical formulation of any one of B4-B5, wherein at least a portion of the plurality of beads are not coated.

B7. The pharmaceutical formulation of B6, wherein the coating is one or more coatings selected from a delayed release coating, a sustained release coating, and a delayed-sustained release coating.

B8. The pharmaceutical formulation of B7, wherein the coating is a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer;
optionally one or more materials selected from a copolymer of methacrylic acid, methyl methacrylate, and methyl acrylate, and a methacrylic acid-acrylate copolymer; and optionally a copolymer of methacrylic acid, methyl methacrylate, and methyl acrylate.

B9. The pharmaceutical formulation of any one of B4-B8 comprising a delayed release coating, wherein the median amount of delayed release coating disposed over the core particle is at least 10 wt. % of the total weight of the CTN bead, or in a range of about 12 wt. % to about 50 wt. %, or about 12 wt. % to about 35 wt. %, based on the total weight of the CTN bead.

B10. The pharmaceutical formulation of any one of B4-B9 comprising a sustained release coating, wherein the sustained release coating comprising one or more materials selected from an alkylcellulose, acrylic acid polymer, a methacrylic acid polymer, an acrylic acid copolymer, a methacrylic acid copolymer, and a cellulose ether;
optionally one or more materials selected from a hydroxyalkylcellulose, a carboxyalkylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, a poly(acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer;
optionally one or more materials selected from poly[ethyl acrylate, methyl methacrylate, trimethylammonioethyl methacrylate chloride], hydroxypropylmethylcellulose, and poly[ethyl acrylate, methyl methacrylate];
optionally poly[ethyl acrylate, methyl methacrylate].

B11. The pharmaceutical formulation of any one of B4-B10 comprising a sustained release coating, wherein the median amount of sustained release coating disposed over the core particle is at least 5 wt. % of the total weight of the core particle, or in a range of about 5 wt. % to about 60 wt. %, or about 15 wt. % to about 60 wt. %, or about 20 wt. % to about 50 wt. % of the total weight of the core particle.

B12. The pharmaceutical formulation of any one of B4-B11 comprising a coating, wherein the coating further comprises a pore former.

B13. The pharmaceutical formulation of B12, wherein the pore former comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide, optionally one or more materials selected from hydroxypropyl methylcellulose, hydroxypropylcellulose, and polyvinylpyrrolidone;
optionally hydroxypropyl methylcellulose.

B14. The pharmaceutical formulation of B12, wherein the pore former is present in the coating in an amount in a range of about 5 wt. % or more, or about 10 wt. % or more, or about 5 wt. % to about 20 wt. %; optionally 15 wt. %.

B15. The pharmaceutical formulation of any one of the B4-B14, wherein the core particles are characterized by having a distribution of particles sizes, and at least a portion of the core particles of the plurality of beads have a core particle size (maximum diameter) of about 0.2 mm to about 2 mm, or about 0.3 mm to about 1.5 mm, 0.4 mm to about 1.5 mm, or about 0.5 mm to about 1 mm, or about 0.5 mm to 0.85 mm, or about 0.5 mm to about 0.71 mm.

B16. The pharmaceutical formulation of B15, wherein the distribution of particles sizes of the core particles is characterized by at least 60% by weight of the core particles having a particle size (maximum diameter) in a range of about 0.4 mm to about 1.5 mm, or about 0.5 mm to about 1 mm, or about 0.5 mm to 0.85 mm, or about 0.5 mm to about 0.71 mm, optionally at least 80% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 90% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 99% by weight of the core particles having a particle size in a range of about 0.4 mm to about 1.5 mm, or about 0.5 mm to about 1 mm, or about 0.5 mm to 0.85 mm, or about 0.5 mm to about 0.71 mm.

B17. The pharmaceutical dosage form of any one of B4-B16, wherein the plurality of CTN beads have a median particle size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm.

B18. The pharmaceutical formulation of any one of B4-B17, wherein the plurality of CTN beads comprises one or more types selected from: an immediate release bead, a sustained release bead, a delayed release bead, and a delayed-sustained release bead.

B19. The pharmaceutical formulation of any one of B4-B18, wherein the plurality of beads comprises a mixture of one or more immediate release beads and one or more sustained release beads.

B20. The pharmaceutical formulation of B19, wherein the ratio of CTN or pharmaceutically acceptable salt thereof is present in the one or more immediate release beads and one or more sustained release beads at a ratio in a range of about 1:100 to about 1:1 parts by weight based on the weight of CTN.

B21. The pharmaceutical formulation of any one of B4-B20, wherein the plurality of beads comprises a mixture of one or more immediate release beads and one or more delayed release beads.

B22. The pharmaceutical formulation of B21, wherein the ratio of CTN or pharmaceutically acceptable salt thereof is present in the one or more immediate release beads and one or more delayed release beads at a ratio in a range of about 1:100 to about 1:1 parts by weight based on the weight of CTN.

B23. The pharmaceutical formulation of any one of B4-B22, wherein the plurality of beads comprises a mixture of one or more delayed release beads and one or more sustained release beads.

B24. The pharmaceutical formulation of B23, wherein the ratio of CTN or pharmaceutically acceptable salt thereof is present in the one or more sustained release beads and one or more delayed release beads at a ratio in a range of about 5:10 to about 1:5 parts by weight based on the weight of CTN.

B25. The pharmaceutical formulation of any one of B4-B24, wherein the plurality of beads comprises a mixture of one or more immediate release beads and one or more delayed-sustained release beads.

B26. The pharmaceutical formulation of B25, wherein the ratio of CTN or pharmaceutically acceptable salt thereof is present in the one or more immediate release beads and one or more delayed-sustained release beads at a ratio in a range of about 1:100 to about 1:1 parts by weight based on the weight of CTN.

B27. The pharmaceutical formulation of any one of B4-B26, wherein the plurality of beads comprises a mixture of one or more immediate release beads, one or more sustained release beads, and one or more delayed release beads.

B28. The pharmaceutical formulation of B27, wherein the ratio of CTN or pharmaceutically acceptable salt thereof is present in the one or more immediate release beads, one or more sustained release beads, and one or more delayed release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-13:3-6:3-6 parts by weight based on the weight of the CTN or salt thereof; and,
optionally a ratio in a range of about 0.7-1:5-15:5-15 parts by weight based on the weight of the CTN or salt thereof.

B29. The pharmaceutical formulation of any one of B4-B28, wherein the plurality of beads comprises a mixture of one or more immediate release beads, one or more sustained release beads, and one or more delayed-sustained release beads.

B30. The pharmaceutical formulation of B29, wherein the ratio of CTN or pharmaceutically acceptable salt thereof is present in the one or more immediate release beads, one or more sustained release beads, and one or more delayed-sustained release beads at a ratio in a range of about 0.1-1:1-20:1-20 parts by weight based on the weight of the CTN or salt thereof;
  optionally a ratio in a range of about 0.5-1:5-20:5-20 parts by weight based on the weight of the CTN or salt thereof;
  optionally a ratio in a range of about 0.7-13:3-6:3-6 parts by weight based on the weight of the CTN or salt thereof; and,
  optionally a ratio in a range of about 0.7-1:5-15:5-15 parts by weight based on the weight of the CTN or salt thereof.

B31. The pharmaceutical formulation of any one of B4-B30, wherein the immediate release bead is free of coatings.

B32. The pharmaceutical formulation of any one of B4-B31, wherein the immediate release beads are present in the formulation in an amount in a range of about 1% to about 75% based on the total weight of the plurality of CTN beads, optionally in a range of about 40% to about 50% based on the total weight of the plurality of CTN beads when the drug loading in the immediate release beads is about 5 wt. % to about wt. %;
  optionally in a range of about 1% to about 50% based on the total weight of the plurality of CTN beads;
  optionally in a range of about 1% to about 25% based on the total weight of the plurality of CTN beads;
  optionally in a range of about 1% to about 10% based on the total weight of the plurality of CTN beads;
  optionally in a range of about 9% to about 19% based on the total weight of the plurality of CTN beads when the drug loading in the immediate release beads is about 40 wt. % to about wt. %, or about 40 wt. % to about 55 wt. %; and
  optionally in a range of about 18% to about 28% based on the total weight of the plurality of CTN beads.

B33. The pharmaceutical formulation of any one of B4-B32 comprising sustained release beads, wherein the sustained release beads are present in the formulation in an amount in a range of about 5% to 80% based on the total weight of the plurality of CTN beads;
  optionally in a range of about 23% to about 33% based on the total weight of the plurality of CTN beads;
  optionally in a range of about 5% to about 65% based on the total weight of the plurality of CTN beads;
  optionally in a range of about 40% to about 50% based on the total weight of the plurality of CTN beads;
  optionally in a range of about 35% to about 55% based on the total weight of the plurality of CTN beads.

B34. The pharmaceutical formulation of any one of B4-B33 comprising delayed release beads, wherein the delayed release beads are present in the formulation in an amount in a range of about 5% to 80% based on the total weight of the plurality of CTN beads;
  optionally in a range of about 21% to about 31% based on the total weight of the plurality of CTN beads;
  optionally in a range of about 5% to about 65% based on the total weight of the plurality of CTN beads;
  optionally in a range of about 36% to about 46% based on the total weight of the plurality of CTN beads;
  optionally in a range of about 30% to about 55% based on the total weight of the plurality of CTN beads.

B35. The pharmaceutical formulation of any one of B4-B34 comprising sustained release beads, wherein at least 90% of the CTN or salt thereof is released from the sustained release beads at a time in a range of 2 to 6 hours according to USP <711> using Apparatus I (basket) in 1000 ml deionized water at 37° C.+/−0.5° C. at 100 rpm.

B36. The pharmaceutical formulation of any one of B4-B35 comprising delayed release beads, wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B37. The pharmaceutical formulation of any one of B4-B36 comprising delayed-sustained release beads, wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B38. The pharmaceutical formulation of any one of B4-B37 comprising immediate release beads, wherein at least 90% of the CTN or salt thereof is released from the immediate release beads at a time in a range of 0 to 2 hours according to USP <711> using Apparatus I (basket) in 1000 ml deionized water at 37° C.+/−0.5° C. at 100 rpm.

B39. The pharmaceutical formulation of any one of B4-B38 comprising a mixture of immediate release beads, sustained release beads, and delayed release beads, wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B40. The pharmaceutical formulation of any one of B1-B39 comprising a mixture of immediate release beads, sustained release beads, and delayed release beads, wherein according to USP <711> using Apparatus I (basket) in 1000 mL 0.1N hydrochloric acid at 37° C.+/−0.5° C. at 100 rpm for 2 hours, followed by Apparatus I (basket) in 1000 mL pH 7.4 phosphate buffer solution at 37° C.+/−0.5° C.) at 100 rpm for 12 the release profile characterized by:

(a) release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points; and/or (b) release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points and still further optionally, the release profile can be characterized by a release of 49% to 73% at the 4-hour mark.

B41. The pharmaceutical formulation of any one of B4-B40 comprising an immediate release bead, wherein the CTN or salt thereof is present in an amount in a range of 5 wt. % to 80 wt. % in the immediate release bead based on the total weight of the immediate release bead;
optionally in a range of 5 wt. % to 60 wt. % based on the total weight of the immediate release bead;
optionally in a range of 5 wt. % to 15 wt. % based on the total weight of the immediate release bead;
optionally in a range of 40 wt. % to 60 wt. % based on the total weight of the immediate release bead; and
optionally a first immediate release bead wherein the CTN or salt thereof is present in an amount in a range of 5 wt. % to 15 wt. % based on the total weight of the immediate release bead and a second immediate release bead wherein the CTN or salt thereof is present in an amount in a range of 40 wt. % to 60 wt. % based on the total weight of the immediate release bead.

B42. The pharmaceutical formulation of any one of B4-B41 comprising a sustained release bead, wherein the CTN or salt thereof is present in an amount in a range of 10 wt. % to 95 wt. % in the sustained release bead based on the total weight of the sustained release bead;
optionally in a range of 40 wt. % to 90 wt. % based on the total weight of the sustained release bead;
optionally in a range of 50 wt. % to 70 wt. % based on the total weight of the sustained release bead.

B43. The pharmaceutical formulation of any one of B4-B42 comprising a delayed release bead, wherein the CTN or salt thereof is present in an amount in a range of 10 wt. % to 95 wt. % in the delayed release bead based on the total weight of the delayed release bead;
optionally in a range of 40 wt. % to 90 wt. % based on the total weight of the delayed release bead;
optionally in a range of 50 wt. % to 70 wt. % based on the total weight of the delayed release bead.

B44. The pharmaceutical formulation of any one of B4-B43, characterized by providing an in vivo absorption profile that is multimodal, optionally bimodal.

B45. The pharmaceutical formulation of any one of B4-B44, wherein the in vivo absorption profile has a first $C_{max}$ at a time in a range of 0 to 4.5 hours, or about 0.5 hours to about 2 hours, or about 3.5 hours to about 4.5 hours.

B46. The pharmaceutical formulation of any one of B4-B45, wherein the in vivo absorption profile has a second $C_{max}$ at a time in a range of about 6 hours to 10 hours, or about 7 hours to 9 hours, or about 7.5 to about 8.5 hours.

B47. The pharmaceutical formulation of any one of B45 or B46, wherein the first $C_{max}$ provided by the formulation in adult humans has an average plasma level in a range of about 250 ng/mL to about 420 ng/mL, or about 320 ng/mL to about 420 ng/mL, or about 325 ng/mL to about 390 ng/mL.

B48. The pharmaceutical formulation of any one of B45-B47, wherein the second $C_{max}$ provided by the formulation in adult humans has an average plasma level in a range of about 450 ng/mL to about 550 ng/mL, or about 470 ng/mL to about 530 ng/mL.

B49. The pharmaceutical formulation of any one of B4-B48, wherein the in vivo absorption profile has a first $C_{max}$ and a second $C_{max}$, wherein the first $C_{max}$ and second $C_{max}$ are separated by a time in a range of 1.5 to 8.5 hours, or about 2 hours to about 6 hours, or about 3 hours to about 5 hours.

B50. The pharmaceutical formulation of any one of B4-B49, wherein one or more of the plurality of CTN beads has a release mechanism comprising one or more of dissolution, diffusion, erosion, osmosis, partitioning, swelling, and targeting.

B51. The pharmaceutical formulation of any one of B4-B50, wherein one or more of the plurality of CTN beads has a diffusion release mechanism.

B52. The pharmaceutical formulation of any one of B4-B51, wherein one or more of the plurality of CTN beads has a pH-triggered dissolution release mechanism.

B53. The pharmaceutical formulation of any one of B4-B52, wherein one or more of the plurality of CTN beads has a combination of pH-triggered dissolution release mechanism and diffusion release mechanism.

B54. The pharmaceutical formulation of any one of B4-B53, wherein one or more of the plurality of CTN beads comprises a porous matrix comprising the CTN.

B55. The pharmaceutical formulation of any one of B4-B54, wherein the plurality of CTN beads are enclosed in one or more containers selected from a capsule, sachet, and stick-pack;
optionally a capsule.

B56. The pharmaceutical formulation of any one of B4-B55, wherein the CTN is present as a salt; optionally as a hydrochloride salt.

B57. The pharmaceutical formulation of any one of B4-B56, wherein the excipient comprises one or more materials selected from a filler and a binder, a glidant, a surfactant, a polymer coating, and a plasticizer;
optionally a combination of a filler and a binder;
optionally a combination of a binder and a polymer coating;
optionally a combination of a filler, a binder, and a polymer coating;
optionally a combination of a filler, a binder, a polymer coating, and a plasticizer.

B58. The pharmaceutical formulation of any one of B4-B56, wherein the excipient comprises one or more materials selected from lactose, mannitol, corn starch, microcrystalline cellulose, hydroxypropyl cellulose, hypromellose, polyvinyl pyrrolidone, talc, polysorbate 80, glycerol monostearate, triethyl citrate, polyvinyl alcohol-polyethylene glycol graft copolymer, and silica.

B59. The pharmaceutical formulation of any one of B4-B57, wherein the formulation is free of disintegrants.

Aspect C

C1. A pharmaceutical formulation comprising centanafadine (CTN) or a pharmaceutically acceptable salt thereof, and an excipient, wherein the pharmaceutical formulation has a multiphasic release profile when tested in acid media for 2 hours followed by pH 7.4 buffered medium, optionally an at least biphasic release profile,
optionally an at least triphasic release profile, and
(a) optionally be characterized by release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points; or
(b) optionally be characterized by release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points; still further optionally, this release profile can be characterized by a release of 49% to 73% at the 4-hour mark.

C2. The pharmaceutical formulation of C1, wherein the formulation is a solid oral formulation and/or a semisolid oral formulation.

C3. The pharmaceutical formulation of C1 or C2, wherein the formulation is a solid oral formulation suitable for pediatric use.

C4. The pharmaceutical formulation of any one of C1-C3, wherein the solid oral formulation comprises one or more forms selected from powder, beads, orodispersible tablet, orodispersible film, mini-tablet, chewable tablet, and soft-chew; optionally selected from powder and beads; optionally beads.

C5. The pharmaceutical formulation of any one of C1-C4, wherein the formulation is a solid oral formulation suitable for adult use.

C6. The pharmaceutical formulation of C5, wherein the solid oral formulation comprises one or more forms selected from a tablet, capsule, sachet, powder, beads, and lozenge; optionally selected from tablet, capsule, beads, and powder; optionally selected from capsule and beads.

C7. The pharmaceutical formulation of any one of C1-C6, wherein the solid oral formulation comprises a plurality of centanafadine (CTN) beads, the plurality of CTN beads each comprising a core particle comprising CTN or a pharmaceutically acceptable salt thereof and an excipient.

Aspects C1-C7 are specifically contemplated to include as further optional features each of aspects B1-B58 below, individually and in combinations thereof.

B1. The pharmaceutical formulation of any one of C1-C7 comprising CTN or a pharmaceutically acceptable salt thereof, wherein the formulation is a solid oral formulation suitable for pediatric use.

B2. The pharmaceutical formulation of B1, wherein the solid oral formulation suitable for pediatric use is selected from one or more types comprising beads, orodispersible tablet, orodispersible film, mini-tablet, chewable tablet, and soft-chew, optionally beads.

B3. The pharmaceutical formulation of any one of B1 or B2, wherein the solid oral formulation suitable for pediatric use is characterized by one or more release profiles, in vivo and/or in vitro, selected from immediate release, sustained release, delayed release, and delayed-sustained release.

B4. The pharmaceutical formulation of any one of B1-B3, wherein the solid oral formulation suitable for pediatric use comprises a plurality of centanafadine (CTN) beads, the plurality of CTN beads each comprising a core particle comprising CTN or a pharmaceutically acceptable salt thereof and an excipient.

B5. The pharmaceutical formulation of B4, wherein at least a portion of the plurality of beads are coated.

B6. The pharmaceutical formulation of any one of B4-B5, wherein at least a portion of the plurality of beads are not coated.

B7. The pharmaceutical formulation of B6, wherein the coating is one or more coatings selected from a delayed release coating, a sustained release coating, and a delayed-sustained release coating.

B8. The pharmaceutical formulation of B7, wherein the coating is a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer;
  optionally one or more materials selected from a copolymer of methacrylic acid, methyl methacrylate, and methyl acrylate, and a methacrylic acid-acrylate copolymer; and optionally a copolymer of methacrylic acid, methyl methacrylate, and methyl acrylate.

B9. The pharmaceutical formulation of any one of B4-B8 comprising a delayed release coating, wherein the median amount of delayed release coating disposed over the core particle is at least 10 wt. % of the total weight of the CTN bead, or in a range of about 12 wt. % to about 50 wt. %, or about 12 wt. % to about 35 wt. %, based on the total weight of the CTN bead.

B10. The pharmaceutical formulation of any one of B4-B9 comprising a sustained release coating, wherein the sustained release coating comprising one or more materials selected from an alkylcellulose, acrylic acid polymer, a methacrylic acid polymer, an acrylic acid copolymer, a methacrylic acid copolymer, and a cellulose ether;
  optionally one or more materials selected from a hydroxyalkylcellulose, a carboxyalkylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, a poly(acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer;
  optionally one or more materials selected from poly[ethyl acrylate, methyl methacrylate, trimethylammonioethyl methacrylate chloride], hydroxypropylmethylcellulose, and poly[ethyl acrylate, methyl methacrylate];
  optionally poly[ethyl acrylate, methyl methacrylate].

B11. The pharmaceutical formulation of any one of B4-B10 comprising a sustained release coating, wherein the median amount of sustained release coating disposed over the core particle is at least 5 wt. % of the total weight of the core particle, or in a range of about 5 wt. % to about 60 wt. %, or about 15 wt. % to about 60 wt. %, or about 20 wt. % to about 50 wt. % of the total weight of the core particle.

B12. The pharmaceutical formulation of any one of B4-B11 comprising a coating, wherein the coating further comprises a pore former.

B13. The pharmaceutical formulation of B12, wherein the pore former comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide,
optionally one or more materials selected from hydroxypropyl methylcellulose, hydroxypropylcellulose, and polyvinylpyrrolidone;
optionally hydroxypropyl methylcellulose.

B14. The pharmaceutical formulation of B12, wherein the pore former is present in the coating in an amount in a range of about 5 wt. % or more, or about 10 wt. % or more, or about 5 wt. % to about 20 wt. %; optionally 15 wt. %.

B15. The pharmaceutical formulation of any one of the B4-B14, wherein the core particles are characterized by having a distribution of particles sizes, and at least a portion of the core particles of the plurality of beads have a core particle size (maximum diameter) of about 0.2 mm to about 2 mm, or about 0.3 mm to about 1.5 mm, 0.4 mm to about 1.5 mm, or about 0.5 mm to about 1 mm, or about 0.5 mm to 0.85 mm, or about 0.5 mm to about 0.71 mm.

B16. The pharmaceutical formulation of B15, wherein the distribution of particles sizes of the core particles is characterized by at least 60% by weight of the core particles having a particle size (maximum diameter) in a range of about 0.4 mm to about 1.5 mm, or about 0.5 mm to about 1 mm, or about 0.5 mm to 0.85 mm, or about 0.5 mm to about 0.71 mm,
optionally at least 80% by weight of the core particles having a particle size in a range of about 0.4 mm to about 1.5 mm, or about 0.5 mm to about 1 mm, or about 0.5 mm to 0.85 mm, or about 0.5 mm to about 0.71 mm,
optionally at least 90% by weight of the core particles having a particle size in a range of about 0.4 mm to about 1.5 mm, or about 0.5 mm to about 1 mm, or about 0.5 mm to 0.85 mm, or about 0.5 mm to about 0.71 mm,
optionally at least 99% by weight of the core particles having a particle size in a range of about 0.4 mm to about 1.5 mm, or about 0.5 mm to about 1 mm, or about 0.5 mm to 0.85 mm, or about 0.5 mm to about 0.71 mm.

B17. The pharmaceutical dosage form of any one of B4-B16, wherein the plurality of CTN beads have a median particle size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm.

B18. The pharmaceutical formulation of any one of B4-B17, wherein the plurality of CTN beads comprises one or more types selected from: an immediate release bead, a sustained release bead, a delayed release bead, and a delayed-sustained release bead.

B19. The pharmaceutical formulation of any one of B4-B18, wherein the plurality of beads comprises a mixture of one or more immediate release beads and one or more sustained release beads.

B20. The pharmaceutical formulation of B19, wherein the ratio of CTN or pharmaceutically acceptable salt thereof is present in the one or more immediate release beads and one or more sustained release beads at a ratio in a range of about 1:100 to about 1:1 parts by weight based on the weight of CTN.

B21. The pharmaceutical formulation of any one of B4-B20, wherein the plurality of beads comprises a mixture of one or more immediate release beads and one or more delayed release beads.

B22. The pharmaceutical formulation of B21, wherein the ratio of CTN or pharmaceutically acceptable salt thereof is present in the one or more immediate release beads and one or more delayed release beads at a ratio in a range of about 1:100 to about 1:1 parts by weight based on the weight of CTN.

B23. The pharmaceutical formulation of any one of B4-B22, wherein the plurality of beads comprises a mixture of one or more delayed release beads and one or more sustained release beads.

B24. The pharmaceutical formulation of B23, wherein the ratio of CTN or pharmaceutically acceptable salt thereof is present in the one or more sustained release beads and one or more delayed release beads at a ratio in a range of about 5:10 to about 1:5 parts by weight based on the weight of CTN.

B25. The pharmaceutical formulation of any one of B4-B24, wherein the plurality of beads comprises a mixture of one or more immediate release beads and one or more delayed-sustained release beads.

B26. The pharmaceutical formulation of B25, wherein the ratio of CTN or pharmaceutically acceptable salt thereof is present in the one or more immediate release beads and one or more delayed-sustained release beads at a ratio in a range of about 1:100 to about 1:1 parts by weight based on the weight of CTN.

B27. The pharmaceutical formulation of any one of B4-B26, wherein the plurality of beads comprises a mixture of one or more immediate release beads, one or more sustained release beads, and one or more delayed release beads.

B28. The pharmaceutical formulation of B27, wherein the ratio of CTN or pharmaceutically acceptable salt thereof is present in the one or more immediate release beads, one or more sustained release beads, and one or more delayed release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-1:3-6:3-6 parts by weight based on the weight of the CTN or salt thereof; and,
optionally a ratio in a range of about 0.7-1:5-15:5-15 parts by weight based on the weight of the CTN or salt thereof.

B29. The pharmaceutical formulation of any one of B4-B28, wherein the plurality of beads comprises a mixture of one or more immediate release beads, one or more sustained release beads, and one or more delayed-sustained release beads.

B30. The pharmaceutical formulation of B29, wherein the ratio of CTN or pharmaceutically acceptable salt thereof is present in the one or more immediate release beads, one or more sustained release beads, and one or more delayed-sustained release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-1:3-6:3-6 parts by weight based on the weight of the CTN or salt thereof; and,
optionally a ratio in a range of about 0.7-1:5-15:5-15 parts by weight based on the weight of the CTN or salt thereof.

B31. The pharmaceutical formulation of any one of B4-B30, wherein the immediate release bead is free of coatings.

B32. The pharmaceutical formulation of any one of B4-B31, wherein the immediate release beads are present in the formulation in an amount in a range of about 1% to about 75% based on the total weight of the plurality of CTN beads,
optionally in a range of about 40% to about 50% based on the total weight of the plurality of CTN beads when the drug loading in the immediate release beads is about 5 wt. % to about wt. %;
optionally in a range of about 1% to about 50% based on the total weight of the plurality of CTN beads;
optionally in a range of about 1% to about 25% based on the total weight of the plurality of CTN beads;
optionally in a range of about 1% to about 10% based on the total weight of the plurality of CTN beads;
optionally in a range of about 9% to about 19% based on the total weight of the plurality of CTN beads when the drug loading in the immediate release beads is about 40 wt. % to about 55 wt. %; and
optionally in a range of about 18% to about 28% based on the total weight of the plurality of CTN beads.

B33. The pharmaceutical formulation of any one of B4-B32 comprising sustained release beads, wherein the sustained release beads are present in the formulation in an amount in a range of about 5% to 80% based on the total weight of the plurality of CTN beads;
optionally in a range of about 23% to about 33% based on the total weight of the plurality of CTN beads;
optionally in a range of about 5% to about 65% based on the total weight of the plurality of CTN beads;
optionally in a range of about 40% to about 55% based on the total weight of the plurality of CTN beads;
optionally in a range of about 35% to about 55% based on the total weight of the plurality of CTN beads.

B34. The pharmaceutical formulation of any one of B4-B33 comprising delayed release beads, wherein the delayed release beads are present in the formulation in an amount in a range of about 5% to about 80% based on the total weight of the plurality of CTN beads;
optionally in a range of about 21% to about 31% based on the total weight of the plurality of CTN beads;
optionally in a range of about 5% to about 65% based on the total weight of the plurality of CTN beads;
optionally in a range of about 36% to about 46% based on the total weight of the plurality of CTN beads;
optionally in a range of about 30% to about 55% based on the total weight of the plurality of CTN beads.

B35. The pharmaceutical formulation of any one of B4-B34 comprising sustained release beads, wherein at least 90% of the CTN or salt thereof is released from the sustained release beads at a time in a range of 2 to 6 hours according to USP <711> using Apparatus I (basket) in 1000 ml deionized water at 37° C.+/−0.5° C. at 100 rpm.

B36. The pharmaceutical formulation of any one of B4-B35 comprising delayed release beads, wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B37. The pharmaceutical formulation of any one of B4-B36 comprising delayed-sustained release beads, wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B38. The pharmaceutical formulation of any one of B4-B37 comprising immediate release beads, wherein at least 90% of the CTN or salt thereof is released from the immediate release beads at a time in a range of 0 to 2 hours according to USP <711> using Apparatus I (basket) in 1000 ml deionized water at 37° C.+/−0.5° C. at 100 rpm.

B39. The pharmaceutical formulation of any one of B4-B38 comprising a mixture of immediate release beads, sustained release beads, and delayed release beads, wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B40. The pharmaceutical formulation of any one of B4-B39 comprising an immediate release bead, wherein the CTN or salt thereof is present in an amount in a range of 5 wt. % to 80 wt. % in the immediate release bead based on the total weight of the immediate release bead;
optionally in a range of 5 wt. % to 60 wt. % based on the total weight of the immediate release bead;
optionally in a range of 5 wt. % to 15 wt. % based on the total weight of the immediate release bead;
optionally in a range of 40 wt. % to 60 wt. % based on the total weight of the immediate release bead; and
optionally a first immediate release bead wherein the CTN or salt thereof is present in an amount in a range of 5 wt. % to 15 wt. % based on the total weight of the immediate release bead and a second immediate release bead wherein the CTN or salt thereof is present in an amount in a range of 40 wt. % to 60 wt. % based on the total weight of the immediate release bead.

B41. The pharmaceutical formulation of any one of B4-B40 comprising a sustained release bead, wherein the CTN or salt thereof is present in an amount in a range of 10 wt. % to 95 wt. % in the sustained release bead based on the total weight of the sustained release bead;

optionally in a range of 40 wt. % to 90 wt. % based on the total weight of the sustained release bead;
optionally in a range of 50 wt. % to 70 wt. % based on the total weight of the sustained release bead.

B42. The pharmaceutical formulation of any one of B4-B41 comprising a delayed release bead, wherein the CTN or salt thereof is present in an amount in a range of 10 wt. % to 95 wt. % in the delayed release bead based on the total weight of the delayed release bead;
optionally in a range of 40 wt. % to 90 wt. % based on the total weight of the delayed release bead;
optionally in a range of 50 wt. % to 70 wt. % based on the total weight of the delayed release bead.

B43. The pharmaceutical formulation of any one of B4-B42, characterized by providing an in vivo absorption profile that is multimodal, optionally bimodal.

B44. The pharmaceutical formulation of any one of B4-B43, wherein the in vivo absorption profile has a first $C_{max}$ at a time in a range of 0 to 4.5 hours, or about 0.5 hours to about 2 hours, or about 3.5 hours to about 4.5 hours.

B45. The pharmaceutical formulation of any one of B4-B44, wherein the in vivo absorption profile has a second $C_{max}$ at a time in a range of about 6 hours to 10 hours, or about 7 hours to 9 hours, or about 7.5 to about 8.5 hours.

B46. The pharmaceutical formulation of any one of B44 or B45, wherein the first $C_{max}$ provided by the formulation in adult humans has an average plasma level in a range of about 250 ng/mL to about 420 ng/mL, or about 320 ng/mL to about 420 ng/mL, or about 325 ng/mL to about 390 ng/mL.

B47. The pharmaceutical formulation of any one of B44-B46, wherein the second $C_{max}$ provided by the formulation in adult humans has an average plasma level in a range of about 450 ng/mL to about 550 ng/mL, or about 470 ng/mL to about 530 ng/mL.

B48. The pharmaceutical formulation of any one of B4-B47, wherein the in vivo absorption profile has a first $C_{max}$ and a second $C_{max}$, wherein the first $C_{max}$ and second $C_{max}$ are separated by a time in a range of 1.5 to 8.5 hours, or about 2 hours to about 6 hours, or about 3 hours to about 5 hours.

B49. The pharmaceutical formulation of any one of B4-B48, wherein one or more of the plurality of CTN beads has a release mechanism comprising one or more of dissolution, diffusion, erosion, osmosis, partitioning, swelling, and targeting.

B50. The pharmaceutical formulation of any one of B4-B49, wherein one or more of the plurality of CTN beads has a diffusion release mechanism.

B51. The pharmaceutical formulation of any one of B4-B50, wherein one or more of the plurality of CTN beads has a pH-triggered dissolution release mechanism.

B52. The pharmaceutical formulation of any one of B4-B51, wherein one or more of the plurality of CTN beads has a combination of pH-triggered dissolution release mechanism and diffusion release mechanism.

B53. The pharmaceutical formulation of any one of B4-B52, wherein one or more of the plurality of CTN beads comprises a porous matrix comprising the CTN.

B54. The pharmaceutical formulation of any one of B4-B53, wherein the plurality of CTN beads are enclosed in one or more containers selected from a capsule, sachet, and stick-pack;
optionally a capsule.

B55. The pharmaceutical formulation of any one of B4-B54, wherein the CTN is present as a salt; optionally as a hydrochloride salt.

B56. The pharmaceutical formulation of any one of B4-B55, wherein the excipient comprises one or more materials selected from a filler and a binder, a glidant, a surfactant, a polymer coating, and a plasticizer;
optionally a combination of a filler and a binder;
optionally a combination of a binder and a polymer coating;
optionally a combination of a filler, a binder, and a polymer coating;
optionally a combination of a filler, a binder, a polymer coating, and a plasticizer.

B57. The pharmaceutical formulation of any one of B4-B56, wherein the excipient comprises one or more materials selected from lactose, mannitol, corn starch, microcrystalline cellulose, hydroxypropyl cellulose, hypromellose, polyvinyl pyrrolidone, talc, polysorbate 80, glycerol monostearate, triethyl citrate, polyvinyl alcohol-polyethylene glycol graft copolymer, and silica.

B58. The pharmaceutical formulation of any one of B4-B56, wherein the formulation is free of disintegrants.

Aspect D

D1. A pharmaceutical formulation comprising centanafadine (CTN) or a pharmaceutically acceptable salt thereof, and an excipient, wherein the pharmaceutical formulation has an in vivo absorption profile that is multimodal, optionally bimodal.

D2. The pharmaceutical formulation of D1, wherein the concentration of CTN in the plasma at 16 hours after administration is less than 300 ng/mL, or less 250 ng/mL or less than 230 ng/mL.

Aspects D1-D2 are specifically contemplated to include as further optional features each of aspects B1-B58, and C1-C7, individually and in combinations thereof.

C1. The pharmaceutical formulation of any one of D1 or D2 comprising centanafadine (CTN) or a pharmaceutically acceptable salt thereof, and an excipient, wherein the pharmaceutical formulation has a multiphasic release profile when tested in acid media for 2 hours followed by pH 7.4 buffered medium,
optionally an at least biphasic release profile,
optionally an at least triphasic release profile, and
(a) optionally be characterized by release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points; or
(b) optionally be characterized by release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points; still further optionally, this release profile can be characterized by a release of 49% to 73% at the 4-hour mark.

C2. The pharmaceutical formulation of C1, wherein the formulation is a solid oral formulation and/or a semisolid oral formulation.

C3. The pharmaceutical formulation of C1 or C2, wherein the formulation is a solid oral formulation suitable for pediatric use.

C4. The pharmaceutical formulation of any one of C1-C3, wherein the solid oral formulation comprises one or more forms selected from powder, beads, orodispersible tablet, orodispersible film, mini-tablet, chewable tablet, and soft-chew; optionally selected from powder and beads; optionally beads.

C5. The pharmaceutical formulation of any one of C1-C4, wherein the formulation is a solid oral formulation suitable for adult use.

C6. The pharmaceutical formulation of C5, wherein the solid oral formulation comprises one or more forms selected from a tablet, capsule, sachet, powder, beads, and lozenge; optionally selected from tablet, capsule, beads, and powder; optionally selected from capsule and beads.

C7. The pharmaceutical formulation of any one of C1-C6, wherein the solid oral formulation comprises a plurality of centanafadine (CTN) beads, the plurality of CTN beads each comprising a core particle comprising CTN or a pharmaceutically acceptable salt thereof and an excipient.

B1. The pharmaceutical formulation of any one of C1-C7, or D1 or D2 comprising CTN or a pharmaceutically acceptable salt thereof, wherein the formulation is a solid oral formulation suitable for pediatric use.

B2. The pharmaceutical formulation of B1, wherein the solid oral formulation suitable for pediatric use is selected from one or more types comprising beads, orodispersible tablet, orodispersible film, mini-tablet, chewable tablet, and soft-chew, optionally beads.

B3. The pharmaceutical formulation of any one of B1 or B2, wherein the solid oral formulation suitable for pediatric use is characterized by one or more release profiles, in vivo and/or in vitro, selected from immediate release, sustained release, delayed release, and delayed-sustained release.

B4. The pharmaceutical formulation of any one of B1-B3, wherein the solid oral formulation suitable for pediatric use comprises a plurality of centanafadine (CTN) beads, the plurality of CTN beads each comprising a core particle comprising CTN or a pharmaceutically acceptable salt thereof and an excipient.

B5. The pharmaceutical formulation of B4, wherein at least a portion of the plurality of beads are coated.

B6. The pharmaceutical formulation of any one of B4-B5, wherein at least a portion of the plurality of beads are not coated.

B7. The pharmaceutical formulation of B6, wherein the coating is one or more coatings selected from a delayed release coating, a sustained release coating, and a delayed-sustained release coating.

B8. The pharmaceutical formulation of B7, wherein the coating is a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer;
optionally one or more materials selected from a copolymer of methacrylic acid, methyl methacrylate, and methyl acrylate, and a methacrylic acid-acrylate copolymer; and optionally a copolymer of methacrylic acid, methyl methacrylate, and methyl acrylate.

B9. The pharmaceutical formulation of any one of B4-B8 comprising a delayed release coating, wherein the median amount of delayed release coating disposed over the core particle is at least 10 wt. % of the total weight of the CTN bead, or in a range of about 12 wt. % to about 50 wt. %, or about 12 wt. % to about 35 wt. %, based on the total weight of the CTN bead.

B10. The pharmaceutical formulation of any one of B4-B9 comprising a sustained release coating, wherein the sustained release coating comprising one or more materials selected from an alkylcellulose, acrylic acid polymer, a methacrylic acid polymer, an acrylic acid copolymer, a methacrylic acid copolymer, and a cellulose ether;
optionally one or more materials selected from a hydroxyalkylcellulose, a carboxyalkylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, a poly(acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer;
optionally one or more materials selected from poly[ethyl acrylate, methyl methacrylate, trimethylammonioethyl methacrylate chloride], hydroxypropylmethylcellulose, and poly[ethyl acrylate, methyl methacrylate];
optionally poly[ethyl acrylate, methyl methacrylate].

B11. The pharmaceutical formulation of any one of B4-B10 comprising a sustained release coating, wherein the median amount of sustained release coating disposed over the core particle is at least 5 wt. % of the total weight of the core particle, or in a range of about 5 wt. % to about 60 wt. %, or about 15 wt. % to about 60 wt. %, or about 20 wt. % to about 50 wt. % of the total weight of the core particle.

B12. The pharmaceutical formulation of any one of B4-B11 comprising a coating, wherein the coating further comprises a pore former.

B13. The pharmaceutical formulation of B12, wherein the pore former comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide, optionally one or more materials selected from hydroxypropyl methylcellulose, hydroxypropylcellulose, and polyvinylpyrrolidone;
optionally hydroxypropyl methylcellulose.

B14. The pharmaceutical formulation of B12, wherein the pore former is present in the coating in an amount in a range of about 5 wt. % or more, or about 10 wt. % or more, or about 5 wt. % to about 20 wt. %; optionally 15 wt. %.

B15. The pharmaceutical formulation of any one of the B4-B14, wherein the core particles are characterized by having a distribution of particles sizes, and at least a portion of the core particles of the plurality of beads have a core particle size (maximum diameter) of about 0.2 mm to about 2 mm, or about 0.3 mm to about 1.5 mm, 0.4 mm to about 1.5 mm, or about 0.5 mm to about 1 mm, or about 0.5 mm to 0.85 mm, or about 0.5 mm to about 0.71 mm.

B16. The pharmaceutical formulation of B15, wherein the distribution of particles sizes of the core particles is characterized by at least 60% by weight of the core particles having a particle size (maximum diameter) in a range of about 0.4 mm to about 1.5 mm, or about 0.5 mm to about 1 mm, or about 0.5 mm to 0.85 mm, or about 0.5 mm to about 0.71 mm, optionally at least 80% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 90% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 99% by weight of the core particles having a particle size in a range of about 0.4 mm to about 1.5 mm, or about 0.5 mm to about 1 mm, or about 0.5 mm to 0.85 mm, or about 0.5 mm to about 0.71 mm.

B17. The pharmaceutical dosage form of any one of B4-B16, wherein the plurality of CTN beads have a median particle size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm.

B18. The pharmaceutical formulation of any one of B4-B17, wherein the plurality of CTN beads comprises one or more types selected from: an immediate release bead, a sustained release bead, a delayed release bead, and a delayed-sustained release bead.

B19. The pharmaceutical formulation of any one of B4-B18, wherein the plurality of beads comprises a mixture of one or more immediate release beads and one or more sustained release beads.

B20. The pharmaceutical formulation of B19, wherein the ratio of CTN or pharmaceutically acceptable salt thereof is present in the one or more immediate release beads and one or more sustained release beads at a ratio in a range of about 1:100 to about 1:1 parts by weight based on the weight of CTN.

B21. The pharmaceutical formulation of any one of B4-B20, wherein the plurality of beads comprises a mixture of one or more immediate release beads and one or more delayed release beads.

B22. The pharmaceutical formulation of B21, wherein the ratio of CTN or pharmaceutically acceptable salt thereof is present in the one or more immediate release beads and one or more delayed release beads at a ratio in a range of about 1:100 to about 1:1 parts by weight based on the weight of CTN.

B23. The pharmaceutical formulation of any one of B4-B22, wherein the plurality of beads comprises a mixture of one or more delayed release beads and one or more sustained release beads.

B24. The pharmaceutical formulation of B23, wherein the ratio of CTN or pharmaceutically acceptable salt thereof is present in the one or more sustained release beads and one or more delayed release beads at a ratio in a range of about 5:10 to about 1:5 parts by weight based on the weight of CTN.

B25. The pharmaceutical formulation of any one of B4-B24, wherein the plurality of beads comprises a mixture of one or more immediate release beads and one or more delayed-sustained release beads.

B26. The pharmaceutical formulation of B25, wherein the ratio of CTN or pharmaceutically acceptable salt thereof is present in the one or more immediate release beads and one or more delayed-sustained release beads at a ratio in a range of about 1:100 to about 1:1 parts by weight based on the weight of CTN.

B27. The pharmaceutical formulation of any one of B4-B26, wherein the plurality of beads comprises a mixture of one or more immediate release beads, one or more sustained release beads, and one or more delayed release beads.

B28. The pharmaceutical formulation of B27, wherein the ratio of CTN or pharmaceutically acceptable salt thereof is present in the one or more immediate release beads, one or more sustained release beads, and one or more delayed release beads at a ratio in a range of about 0.1-1:1-20:1-20 parts by weight based on the weight of the CTN or salt thereof;
  optionally a ratio in a range of about 0.5-1:5-20:5-20 parts by weight based on the weight of the CTN or salt thereof;
  optionally a ratio in a range of about 0.7-1:3:3-6:3-6 parts by weight based on the weight of the CTN or salt thereof; and,
  optionally a ratio in a range of about 0.7-1:5-15:5-15 parts by weight based on the weight of the CTN or salt thereof.

B29. The pharmaceutical formulation of any one of B4-B28, wherein the plurality of beads comprises a mixture of one or more immediate release beads, one or more sustained release beads, and one or more delayed-sustained release beads.

B30. The pharmaceutical formulation of B29, wherein the ratio of CTN or pharmaceutically acceptable salt thereof is present in the one or more immediate release beads, one or more sustained release beads, and one or more delayed-sustained release beads at a ratio in a range of about 0.1-1:1-20:1-20 parts by weight based on the weight of the CTN or salt thereof;
  optionally a ratio in a range of about 0.5-1:5-20:5-20 parts by weight based on the weight of the CTN or salt thereof;
  optionally a ratio in a range of about 0.7-1:3:3-6:3-6 parts by weight based on the weight of the CTN or salt thereof; and,
  optionally a ratio in a range of about 0.7-1:5-15:5-15 parts by weight based on the weight of the CTN or salt thereof.

B31. The pharmaceutical formulation of any one of B4-B30, wherein the immediate release bead is free of coatings.

B32. The pharmaceutical formulation of any one of B4-B31, wherein the immediate release beads are present in the formulation in an amount in a range of about 1% to about 75% based on the total weight of the plurality of CTN beads,
  optionally in a range of about 40% to about 55% based on the total weight of the plurality of CTN beads when the drug loading in the immediate release beads is about 5 wt. % to about wt. %;
  optionally in a range of about 1% to about 50% based on the total weight of the plurality of CTN beads;
  optionally in a range of about 1% to about 25% based on the total weight of the plurality of CTN beads;
  optionally in a range of about 1% to about 10% based on the total weight of the plurality of CTN beads;
  optionally in a range of about 9% to about 19% based on the total weight of the plurality of CTN beads when the drug loading in the immediate release beads is about 40 wt. % to about 55 wt. %; and
  optionally in a range of about 18% to about 28% based on the total weight of the plurality of CTN beads.

B33. The pharmaceutical formulation of any one of B4-B32 comprising sustained release beads, wherein the sustained release beads are present in the formulation in an amount in a range of about 5% to 80% based on the total weight of the plurality of CTN beads;
  optionally in a range of about 23% to about 33% based on the total weight of the plurality of CTN beads;

optionally in a range of about 5% to about 65% based on the total weight of the plurality of CTN beads;
optionally in a range of about 40% to about 55% based on the total weight of the plurality of CTN beads;
optionally in a range of about 35% to about 55% based on the total weight of the plurality of CTN beads.

B34. The pharmaceutical formulation of any one of B4-B33 comprising delayed release beads, wherein the delayed release beads are present in the formulation in an amount in a range of about 5% to 80% based on the total weight of the plurality of CTN beads;
optionally in a range of about 21% to about 31% based on the total weight of the plurality of CTN beads;
optionally in a range of about 5% to about 65% based on the total weight of the plurality of CTN beads;
optionally in a range of about 36% to about 46% based on the total weight of the plurality of CTN beads;
optionally in a range of about 30% to about 55% based on the total weight of the plurality of CTN beads.

B35. The pharmaceutical formulation of any one of B4-B34 comprising sustained release beads, wherein at least 90% of the CTN or salt thereof is released from the sustained release beads at a time in a range of 2 to 6 hours according to USP <711> using Apparatus I (basket) in 1000 ml deionized water at 37° C.+/−0.5° C. at 100 rpm.

B36. The pharmaceutical formulation of any one of B4-B35 comprising delayed release beads, wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B37. The pharmaceutical formulation of any one of B4-B36 comprising delayed-sustained release beads, wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B38. The pharmaceutical formulation of any one of B4-B37 comprising immediate release beads, wherein at least 90% of the CTN or salt thereof is released from the immediate release beads at a time in a range of 0 to 2 hours according to USP <711> using Apparatus I (basket) in 1000 ml deionized water at 37° C.+/−0.5° C. at 100 rpm.

B39. The pharmaceutical formulation of any one of B4-B38 comprising a mixture of immediate release beads, sustained release beads, and delayed release beads, wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B40. The pharmaceutical formulation of any one of B4-B39 comprising an immediate release bead, wherein the CTN or salt thereof is present in an amount in a range of 5 wt. % to 80 wt. % in the immediate release bead based on the total weight of the immediate release bead;
optionally in a range of 5 wt. % to 60 wt. % based on the total weight of the immediate release bead;
optionally in a range of 5 wt. % to 15 wt. % based on the total weight of the immediate release bead;
optionally in a range of 40 wt. % to 60 wt. % based on the total weight of the immediate release bead; and
optionally a first immediate release bead wherein the CTN or salt thereof is present in an amount in a range of 5 wt. % to 15 wt. % based on the total weight of the immediate release bead and a second immediate release bead wherein the CTN or salt thereof is present in an amount in a range of 40 wt. % to 60 wt. % based on the total weight of the immediate release bead.

B41. The pharmaceutical formulation of any one of B4-B40 comprising a sustained release bead, wherein the CTN or salt thereof is present in an amount in a range of 10 wt. % to 95 wt. % in the sustained release bead based on the total weight of the sustained release bead;
optionally in a range of 40 wt. % to 90 wt. % based on the total weight of the sustained release bead;
optionally in a range of 50 wt. % to 70 wt. % based on the total weight of the sustained release bead.

B42. The pharmaceutical formulation of any one of B4-B41 comprising a delayed release bead, wherein the CTN or salt thereof is present in an amount in a range of 10 wt. % to 95 wt. % in the delayed release bead based on the total weight of the delayed release bead;
optionally in a range of 40 wt. % to 90 wt. % based on the total weight of the delayed release bead;
optionally in a range of 50 wt. % to 70 wt. % based on the total weight of the delayed release bead.

B43. The pharmaceutical formulation of any one of B4-B42, characterized by providing an in vivo absorption profile that is multimodal, optionally bimodal.

B44. The pharmaceutical formulation of any one of B4-B43, wherein the in vivo absorption profile has a first $C_{max}$ at a time in a range of 0 to 4.5 hours, or about 0.5 hours to about 2 hours, or about 3.5 hours to about 4.5 hours.

B45. The pharmaceutical formulation of any one of B4-B44, wherein the in vivo absorption profile has a second $C_{max}$ at a time in a range of about 6 hours to 10 hours, or about 7 hours to 9 hours, or about 7.5 to about 8.5 hours.

B46. The pharmaceutical formulation of any one of B44 or B45, wherein the first $C_{max}$ provided by the formulation in adult humans has an average plasma level in a range of about 250 ng/mL to about 420 ng/mL, or about 320 ng/mL to about 420 ng/mL, or about 325 ng/mL to about 390 ng/mL.

B47. The pharmaceutical formulation of any one of B44-B46, wherein the second $C_{max}$ provided by the formulation in adult humans has an average plasma level in a range of about 450 ng/mL to about 550 ng/mL, or about 470 ng/mL to about 530 ng/m L.

B48. The pharmaceutical formulation of any one of B4-B47, wherein the in vivo absorption profile has a first $C_{max}$ and a second $C_{max}$, wherein the first $C_{max}$ and second $C_{max}$ are separated by a time in a range of 1.5 to 8.5 hours, or about 2 hours to about 6 hours, or about 3 hours to about 5 hours.

B49. The pharmaceutical formulation of any one of B4-B48, wherein one or more of the plurality of CTN beads has a release mechanism comprising one or more of dissolution, diffusion, erosion, osmosis, partitioning, swelling, and targeting.

B50. The pharmaceutical formulation of any one of B4-B49, wherein one or more of the plurality of CTN beads has a diffusion release mechanism.

B51. The pharmaceutical formulation of any one of B4-B50, wherein one or more of the plurality of CTN beads has a pH-triggered dissolution release mechanism.

B52. The pharmaceutical formulation of any one of B4-B51, wherein one or more of the plurality of CTN beads has a combination of pH-triggered dissolution release mechanism and diffusion release mechanism.

B53. The pharmaceutical formulation of any one of B4-B52, wherein one or more of the plurality of CTN beads comprises a porous matrix comprising the CTN.

B54. The pharmaceutical formulation of any one of B4-B53, wherein the plurality of CTN beads are enclosed in one or more containers selected from a capsule, sachet, and stick-pack;
optionally a capsule.

B55. The pharmaceutical formulation of any one of B4-B54, wherein the CTN is present as a salt; optionally as a hydrochloride salt.

B56. The pharmaceutical formulation of any one of B4-B55, wherein the excipient comprises one or more materials selected from a filler and a binder, a glidant, a surfactant, a polymer coating, and a plasticizer;
optionally a combination of a filler and a binder;
optionally a combination of a binder and a polymer coating;
optionally a combination of a filler, a binder, and a polymer coating;
optionally a combination of a filler, a binder, a polymer coating, and a plasticizer.

B57. The pharmaceutical formulation of any one of B4-B55, wherein the excipient comprises one or more materials selected from lactose, mannitol, corn starch, microcrystalline cellulose, hydroxypropyl cellulose, hypromellose, polyvinyl pyrrolidone, talc, polysorbate 80, glycerol monostearate, triethyl citrate, polyvinyl alcohol-polyethylene glycol graft copolymer, and silica.

B58. The pharmaceutical formulation of any one of B4-B56, wherein the formulation is free of disintegrants.

Aspect E

E1. A pharmaceutical formulation comprising centanafadine (CTN) or a pharmaceutically acceptable salt thereof and an excipient, wherein the formulation exhibits in vivo delayed-sustained release profile.

E2. The pharmaceutical formulation of E1, wherein the formulation is a solid oral formulation and/or a semisolid oral formulation.

E3. The pharmaceutical formulation of E1 or E2, wherein the formulation comprises a core and a coating disposed over the core.

E4. The pharmaceutical formulation of E3, wherein the coating disposed over the core has a pH-dependent dissolution trigger.

E5. The pharmaceutical formulation of E4, wherein the coating disposed over the core begins to dissolve at a pH of at least 7, optionally in a range of about 7 to about 8, optionally in a range of about 7.2 to about 7.6.

E6. The pharmaceutical formulation of any one of E3-E5, wherein the coating comprises a methacrylic acid polymer.

E7. The pharmaceutical formulation of E6, wherein the coating comprises one or more polymers selected from co-polymerized methacrylic acid/methacrylic acid methyl esters, co-polymerized methacrylic acid/methyl methacrylate, co-polymerized methylacrylate/methyl methacrylate/methacrylic acid;
optionally one or more polymers selected from a copolymer of methacrylic acid, methyl methacrylate, and methyl acrylate, and a methacrylic acid-acrylate copolymer; optionally a copolymer of methacrylic acid, methyl methacrylate, and methyl acrylate.

Aspects E1-E7 are specifically contemplated to include as further optional features each of aspects B1-B58, C1-C7, and D1-D2, individually and in combinations thereof.

D1. The pharmaceutical formulation of any one of E1-E7 comprising centanafadine (CTN) or a pharmaceutically acceptable salt thereof, and an excipient, wherein the pharmaceutical formulation has an in vivo absorption profile that is multimodal, optionally bimodal.

D2. The pharmaceutical formulation of D1, wherein the concentration of CTN in the plasma at 16 hours after administration is less than 300 ng/mL, or less 250 ng/mL or less than 230 ng/mL.

C1. The pharmaceutical formulation of any one of E1-E7, or D1 or D2 comprising centanafadine (CTN) or a pharmaceutically acceptable salt thereof, and an excipient, wherein the pharmaceutical formulation has a multiphasic release profile when tested in acid media for 2 hours followed by pH 7.4 buffered medium,
optionally an at least biphasic release profile,
optionally an at least triphasic release profile, and
(a) optionally be characterized by release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points; or
(b) optionally be characterized by release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points; still further optionally, this release profile can be characterized by a release of 49% to 73% at the 4-hour mark.

C2. The pharmaceutical formulation of C1, wherein the formulation is a solid oral formulation and/or a semisolid oral formulation.

C3. The pharmaceutical formulation of C1 or C2, wherein the formulation is a solid oral formulation suitable for pediatric use.

C4. The pharmaceutical formulation of any one of C1-C3, wherein the solid oral formulation comprises one or more forms selected from powder, beads, orodispersible tablet, orodispersible film, mini-tablet, chewable tablet, and soft-chew; optionally selected from powder and beads; optionally beads.

C5. The pharmaceutical formulation of any one of C1-C4, wherein the formulation is a solid oral formulation suitable for adult use.

C6. The pharmaceutical formulation of C5, wherein the solid oral formulation comprises one or more forms selected from a tablet, capsule, sachet, powder, beads, and lozenge; optionally selected from tablet, capsule, beads, and powder; optionally selected from capsule and beads.

C7. The pharmaceutical formulation of any one of C1-C6, wherein the solid oral formulation comprises a plurality of centanafadine (CTN) beads, the plurality of CTN beads each comprising a core particle comprising CTN or a pharmaceutically acceptable salt thereof and an excipient.

B1. The pharmaceutical formulation of any one of C1-C7, or D1 or D2, or E1-E7 comprising CTN or a pharmaceutically acceptable salt thereof, wherein the formulation is a solid oral formulation suitable for pediatric use.

B2. The pharmaceutical formulation of B1, wherein the solid oral formulation suitable for pediatric use is selected from one or more types comprising beads, orodispersible tablet, orodispersible film, mini-tablet, chewable tablet, and soft-chew, optionally beads.

B3. The pharmaceutical formulation of any one of B1 or B2, wherein the solid oral formulation suitable for pediatric use is characterized by one or more release profiles, in vivo and/or in vitro, selected from immediate release, sustained release, delayed release, and delayed-sustained release.

B4. The pharmaceutical formulation of any one of B1-B3, wherein the solid oral formulation suitable for pediatric use comprises a plurality of centanafadine (CTN) beads, the plurality of CTN beads each comprising a core particle comprising CTN or a pharmaceutically acceptable salt thereof and an excipient.

B5. The pharmaceutical formulation of B4, wherein at least a portion of the plurality of beads are coated.

B6. The pharmaceutical formulation of any one of B4-B5, wherein at least a portion of the plurality of beads are not coated.

B7. The pharmaceutical formulation of B6, wherein the coating is one or more coatings selected from a delayed release coating, a sustained release coating, and a delayed-sustained release coating.

B8. The pharmaceutical formulation of B7, wherein the coating is a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer;
optionally one or more materials selected from a copolymer of methacrylic acid, methyl methacrylate, and methyl acrylate, and a methacrylic acid-acrylate copolymer; and optionally a copolymer of methacrylic acid, methyl methacrylate, and methyl acrylate.

B9. The pharmaceutical formulation of any one of B4-B8 comprising a delayed release coating, wherein the median amount of delayed release coating disposed over the core particle is at least 10 wt. % of the total weight of the CTN bead, or in a range of about 12 wt. % to about 50 wt. %, or about 12 wt. % to about 35 wt. %, based on the total weight of the CTN bead.

B10. The pharmaceutical formulation of any one of B4-B9 comprising a sustained release coating, wherein the sustained release coating comprising one or more materials selected from an alkylcellulose, acrylic acid polymer, a methacrylic acid polymer, an acrylic acid copolymer, a methacrylic acid copolymer, and a cellulose ether;
optionally one or more materials selected from a hydroxyalkylcellulose, a carboxyalkylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, a poly (acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer;
optionally one or more materials selected from poly[ethyl acrylate, methyl methacrylate, trimethylammonioethyl methacrylate chloride], hydroxypropylmethylcellulose, and poly[ethyl acrylate, methyl methacrylate];
optionally poly[ethyl acrylate, methyl methacrylate].

B11. The pharmaceutical formulation of any one of B4-B10 comprising a sustained release coating, wherein the median amount of sustained release coating disposed over the core particle is at least 5 wt. % of the total weight of the core particle, or in a range of about 5 wt. % to about 60 wt. %, or about 15 wt. % to about 60 wt. %, or about 20 wt. % to about 50 wt. % of the total weight of the core particle.

B12. The pharmaceutical formulation of any one of B4-B11 comprising a coating, wherein the coating further comprises a pore former.

B13. The pharmaceutical formulation of B12, wherein the pore former comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide,
optionally one or more materials selected from hydroxypropyl methylcellulose, hydroxypropylcellulose, and polyvinylpyrrolidone;
optionally hydroxypropyl methylcellulose.

B14. The pharmaceutical formulation of B12, wherein the pore former is present in the coating in an amount in a range of about 5 wt. % or more, or about 10 wt. % or more, or about 5 wt. % to about 20 wt. %; optionally 15 wt. %.

B15. The pharmaceutical formulation of any one of the B4-B14, wherein the core particles are characterized by having a distribution of particles sizes, and at least a portion of the core particles of the plurality of beads have a core particle size (maximum diameter) of about 0.2 mm to about 2 mm, or about 0.3 mm to about 1.5 mm, 0.4 mm to about 1.5 mm, or about 0.5 mm to about 1 mm, or about 0.5 mm to 0.85 mm, or about 0.5 mm to about 0.71 mm.

B16. The pharmaceutical formulation of B15, wherein the distribution of particles sizes of the core particles is characterized by at least 60% by weight of the core particles having a particle size (maximum diameter) in a range of about 0.4 mm to about 1.5 mm, or about 0.5 mm to about 1 mm, or about 0.5 mm to 0.85 mm, or about 0.5 mm to about 0.71 mm,
optionally at least 80% by weight of the core particles having a particle size in a range of about 0.4 mm to about 1.5 mm, or about 0.5 mm to about 1 mm, or about 0.5 mm to 0.85 mm, or about 0.5 mm to about 0.71 mm,
optionally at least 90% by weight of the core particles having a particle size in a range of about 0.4 mm to about 1.5 mm, or about 0.5 mm to about 1 mm, or about 0.5 mm to 0.85 mm, or about 0.5 mm to about 0.71 mm, optionally at least 99% by weight of the core particles having a particle size in a range of about 0.4 mm to about 1.5 mm, or about 0.5 mm to about 1 mm, or about 0.5 mm to 0.85 mm, or about 0.5 mm to about 0.71 mm.

B17. The pharmaceutical dosage form of any one of B4-B16, wherein the plurality of CTN beads have a median particle size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm.

B18. The pharmaceutical formulation of any one of B4-B17, wherein the plurality of CTN beads comprises one or more types selected from: an immediate release bead, a sustained release bead, a delayed release bead, and a delayed-sustained release bead.

B19. The pharmaceutical formulation of any one of B4-B18, wherein the plurality of beads comprises a mixture of one or more immediate release beads and one or more sustained release beads.

B20. The pharmaceutical formulation of B19, wherein the ratio of CTN or pharmaceutically acceptable salt thereof is present in the one or more immediate release beads and one or more sustained release beads at a ratio in a range of about 1:100 to about 1:1 parts by weight based on the weight of CTN.

B21. The pharmaceutical formulation of any one of B4-B20, wherein the plurality of beads comprises a mixture of one or more immediate release beads and one or more delayed release beads.

B22. The pharmaceutical formulation of B21, wherein the ratio of CTN or pharmaceutically acceptable salt thereof is present in the one or more immediate release beads and one or more delayed release beads at a ratio in a range of about 1:100 to about 1:1 parts by weight based on the weight of CTN.

B23. The pharmaceutical formulation of any one of B4-B22, wherein the plurality of beads comprises a mixture of one or more delayed release beads and one or more sustained release beads.

B24. The pharmaceutical formulation of B23, wherein the ratio of CTN or pharmaceutically acceptable salt thereof is present in the one or more sustained release beads and one or more delayed release beads at a ratio in a range of about 5:10 to about 1:5 parts by weight based on the weight of CTN.

B25. The pharmaceutical formulation of any one of B4-B24, wherein the plurality of beads comprises a mixture of one or more immediate release beads and one or more delayed-sustained release beads.

B26. The pharmaceutical formulation of B25, wherein the ratio of CTN or pharmaceutically acceptable salt thereof is present in the one or more immediate release beads and one or more delayed-sustained release beads at a ratio in a range of about 1:100 to about 1:1 parts by weight based on the weight of CTN.

B27. The pharmaceutical formulation of any one of B4-B26, wherein the plurality of beads comprises a mixture of one or more immediate release beads, one or more sustained release beads, and one or more delayed release beads.

B28. The pharmaceutical formulation of B27, wherein the ratio of CTN or pharmaceutically acceptable salt thereof is present in the one or more immediate release beads, one or more sustained release beads, and one or more delayed release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-13:3-6:3-6 parts by weight based on the weight of the CTN or salt thereof; and,
optionally a ratio in a range of about 0.7-1:5-15:5-15 parts by weight based on the weight of the CTN or salt thereof.

B29. The pharmaceutical formulation of any one of B4-B28, wherein the plurality of beads comprises a mixture of one or more immediate release beads, one or more sustained release beads, and one or more delayed-sustained release beads.

B30. The pharmaceutical formulation of B29, wherein the ratio of CTN or pharmaceutically acceptable salt thereof is present in the one or more immediate release beads, one or more sustained release beads, and one or more delayed-sustained release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-13:3-6:3-6 parts by weight based on the weight of the CTN or salt thereof; and,
optionally a ratio in a range of about 0.7-1:5-15:5-15 parts by weight based on the weight of the CTN or salt thereof.

B31. The pharmaceutical formulation of any one of B4-B30, wherein the immediate release bead is free of coatings.

B32. The pharmaceutical formulation of any one of B4-B31, wherein the immediate release beads are present in the formulation in an amount in a range of about 1% to about 75% based on the total weight of the plurality of CTN beads,
optionally in a range of about 40% to about 55% based on the total weight of the plurality of CTN beads when the drug loading in the immediate release beads is about 5 wt. % to about wt. %;
optionally in a range of about 1% to about 50% based on the total weight of the plurality of CTN beads;
optionally in a range of about 1% to about 25% based on the total weight of the plurality of CTN beads;
optionally in a range of about 1% to about 10% based on the total weight of the plurality of CTN beads;
optionally in a range of about 9% to about 19% based on the total weight of the plurality of CTN beads when the drug loading in the immediate release beads is about 40 wt. % to about 55 wt. %; and
optionally in a range of about 18% to about 28% based on the total weight of the plurality of CTN beads.

B33. The pharmaceutical formulation of any one of B4-B32 comprising sustained release beads, wherein the sustained release beads are present in the formulation in an amount in a range of about 5% to 80% based on the total weight of the plurality of CTN beads;
optionally in a range of about 23% to about 33% based on the total weight of the plurality of CTN beads;
optionally in a range of about 5% to about 65% based on the total weight of the plurality of CTN beads;

optionally in a range of about 40% to about 55% based on the total weight of the plurality of CTN beads;

optionally in a range of about 35% to about 55% based on the total weight of the plurality of CTN beads.

B34. The pharmaceutical formulation of any one of B4-B33 comprising delayed release beads, wherein the delayed release beads are present in the formulation in an amount in a range of about 5% to 80% based on the total weight of the plurality of CTN beads;

optionally in a range of about 21% to about 31% based on the total weight of the plurality of CTN beads;

optionally in a range of about 5% to about 65% based on the total weight of the plurality of CTN beads;

optionally in a range of about 36% to about 46% based on the total weight of the plurality of CTN beads;

optionally in a range of about 30% to about 55% based on the total weight of the plurality of CTN beads.

B35. The pharmaceutical formulation of any one of B4-B34 comprising sustained release beads, wherein at least 90% of the CTN or salt thereof is released from the sustained release beads at a time in a range of 2 to 6 hours according to USP <711> using Apparatus I (basket) in 1000 ml deionized water at 37° C.+/−0.5° C. at 100 rpm.

B36. The pharmaceutical formulation of any one of B4-B35 comprising delayed release beads, wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B37. The pharmaceutical formulation of any one of B4-B36 comprising delayed-sustained release beads, wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B38. The pharmaceutical formulation of any one of B4-B37 comprising immediate release beads, wherein at least 90% of the CTN or salt thereof is released from the immediate release beads at a time in a range of 0 to 2 hours according to USP <711> using Apparatus I (basket) in 1000 ml deionized water at 37° C.+/−0.5° C. at 100 rpm.

B39. The pharmaceutical formulation of any one of B4-B38 comprising a mixture of immediate release beads, sustained release beads, and delayed release beads, wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B40. The pharmaceutical formulation of any one of B4-B39 comprising an immediate release bead, wherein the CTN or salt thereof is present in an amount in a range of 5 wt. % to 80 wt. % in the immediate release bead based on the total weight of the immediate release bead;

optionally in a range of 5 wt. % to 60 wt. % based on the total weight of the immediate release bead;

optionally in a range of 5 wt. % to 15 wt. % based on the total weight of the immediate release bead;

optionally in a range of 40 wt. % to 60 wt. % based on the total weight of the immediate release bead; and optionally a first immediate release bead wherein the CTN or salt thereof is present in an amount in a range of 5 wt. % to 15 wt. % based on the total weight of the immediate release bead and a second immediate release bead wherein the CTN or salt thereof is present in an amount in a range of 40 wt. % to 60 wt. % based on the total weight of the immediate release bead.

B41. The pharmaceutical formulation of any one of B4-B40 comprising a sustained release bead, wherein the CTN or salt thereof is present in an amount in a range of 10 wt. % to 95 wt. % in the sustained release bead based on the total weight of the sustained release bead;

optionally in a range of 40 wt. % to 90 wt. % based on the total weight of the sustained release bead;

optionally in a range of 50 wt. % to 70 wt. % based on the total weight of the sustained release bead.

B42. The pharmaceutical formulation of any one of B4-B41 comprising a delayed release bead, wherein the CTN or salt thereof is present in an amount in a range of 10 wt. % to 95 wt. % in the delayed release bead based on the total weight of the delayed release bead;

optionally in a range of 40 wt. % to 90 wt. % based on the total weight of the delayed release bead;

optionally in a range of 50 wt. % to 70 wt. % based on the total weight of the delayed release bead.

B43. The pharmaceutical formulation of any one of B4-B42, characterized by providing an in vivo absorption profile that is multimodal, optionally bimodal.

B44. The pharmaceutical formulation of any one of B4-B43, wherein the in vivo absorption profile has a first $C_{max}$ at a time in a range of 0 to 4.5 hours, or about 0.5 hours to about 2 hours, or about 3.5 hours to about 4.5 hours.

B45. The pharmaceutical formulation of any one of B4-B44, wherein the in vivo absorption profile has a second $C_{max}$ at a time in a range of about 6 hours to 10 hours, or about 7 hours to 9 hours, or about 7.5 to about 8.5 hours.

B46. The pharmaceutical formulation of any one of B44 or B45, wherein the first $C_{max}$ provided by the formulation in adult humans has an average plasma level in a range of about 250 ng/mL to about 420 ng/mL, or about 320 ng/mL to about 420 ng/mL, or about 325 ng/mL to about 390 ng/mL.

B47. The pharmaceutical formulation of any one of B44-B46, wherein the second $C_{max}$ provided by the formulation in adult humans has an average plasma level in a range of about 450 ng/mL to about 550 ng/mL, or about 470 ng/mL to about 530 ng/mL.

B48. The pharmaceutical formulation of any one of B4-B47, wherein the in vivo absorption profile has a first $C_{max}$ and a second $C_{max}$, wherein the first $C_{max}$ and second $C_{max}$ are separated by a time in a range of 1.5 to 8.5 hours, or about 2 hours to about 6 hours, or about 3 hours to about 5 hours.

B49. The pharmaceutical formulation of any one of B4-B48, wherein one or more of the plurality of CTN beads has a release mechanism comprising one or more of dissolution, diffusion, erosion, osmosis, partitioning, swelling, and targeting.

B50. The pharmaceutical formulation of any one of B4-B49, wherein one or more of the plurality of CTN beads has a diffusion release mechanism.

B51. The pharmaceutical formulation of any one of B4-B50, wherein one or more of the plurality of CTN beads has a pH-triggered dissolution release mechanism.

B52. The pharmaceutical formulation of any one of B4-B51, wherein one or more of the plurality of CTN beads has a combination of pH-triggered dissolution release mechanism and diffusion release mechanism.

B53. The pharmaceutical formulation of any one of B4-B52, wherein one or more of the plurality of CTN beads comprises a porous matrix comprising the CTN.

B54. The pharmaceutical formulation of any one of B4-B53, wherein the plurality of CTN beads are enclosed in one or more containers selected from a capsule, sachet, and stick-pack;
optionally a capsule.

B55. The pharmaceutical formulation of any one of B4-B54, wherein the CTN is present as a salt; optionally as a hydrochloride salt.

B56. The pharmaceutical formulation of any one of B4-B55, wherein the excipient comprises one or more materials selected from a filler and a binder, a glidant, a surfactant, a polymer coating, and a plasticizer;
optionally a combination of a filler and a binder;
optionally a combination of a binder and a polymer coating;
optionally a combination of a filler, a binder, and a polymer coating;
optionally a combination of a filler, a binder, a polymer coating, and a plasticizer.

B57. The pharmaceutical formulation of any one of B4-B55, wherein the excipient comprises one or more materials selected from lactose, mannitol, corn starch, microcrystalline cellulose, hydroxypropyl cellulose, hypromellose, polyvinyl pyrrolidone, talc, polysorbate 80, glycerol monostearate, triethyl citrate, polyvinyl alcohol-polyethylene glycol graft copolymer, and silica.

B58. The pharmaceutical formulation of any one of B4-B56, wherein the formulation is free of disintegrants.

Aspect F

F1. A pharmaceutical formulation comprising a plurality of centanafadine (CTN) beads, the plurality of CTN beads each comprising a core particle comprising CTN or a pharmaceutically acceptable salt thereof and an excipient, wherein at least a portion of the core particles comprise CTN or a pharmaceutically acceptable salt thereof in an amount in a range of about 70 wt. % to about 90 wt. %.

Aspect F1 is specifically contemplated to include as further optional features each of aspects B1-B58, C1-C7, D1-D2, and E1-E7, individually and in combinations thereof.

E1. The pharmaceutical formulation of F1 comprising centanafadine (CTN) or a pharmaceutically acceptable salt thereof and an excipient, wherein the formulation exhibits in vivo delayed-sustained release profile.

E2. The pharmaceutical formulation of E1, wherein the formulation is a solid oral formulation and/or a semisolid oral formulation.

E3. The pharmaceutical formulation of E1 or E2, wherein the formulation comprises a core and a coating disposed over the core.

E4. The pharmaceutical formulation of E3, wherein the coating disposed over the core has a pH-dependent dissolution trigger.

E5. The pharmaceutical formulation of E4, wherein the coating disposed over the core begins to dissolve at a pH of at least 7, optionally in a range of about 7 to about 8, optionally in a range of about 7.2 to about 7.6.

E6. The pharmaceutical formulation of any one of E3-E5, wherein the coating comprises a methacrylic acid polymer.

E7. The pharmaceutical formulation of E6, wherein the coating comprises one or more polymers selected from co-polymerized methacrylic acid/methacrylic acid methyl esters, co-polymerized methacrylic acid/methyl methacrylate, co-polymerized methylacrylate/methyl methacrylate/methacrylic acid;
optionally one or more polymers selected from a copolymer of methacrylic acid, methyl methacrylate, and methyl acrylate, and a methacrylic acid-acrylate copolymer; optionally a copolymer of methacrylic acid, methyl methacrylate, and methyl acrylate.

D1. The pharmaceutical formulation of any one of E1-E7 or F1 comprising centanafadine (CTN) or a pharmaceutically acceptable salt thereof, and an excipient, wherein the pharmaceutical formulation has an in vivo absorption profile that is multimodal, optionally bimodal.

D2. The pharmaceutical formulation of D1, wherein the concentration of CTN in the plasma at 16 hours after administration is less than 300 ng/mL, or less 250 ng/mL or less than 230 ng/mL.

C1. The pharmaceutical formulation of any one of E1-E7, or D1 or D2 or F1 comprising centanafadine (CTN) or a pharmaceutically acceptable salt thereof, and an excipient, wherein the pharmaceutical formulation has a multiphasic release profile when tested in acid media for 2 hours followed by pH 7.4 buffered medium,
optionally an at least biphasic release profile,
optionally an at least triphasic release profile, and
(a) optionally be characterized by release of about 22% to about 45% CTN at the 3-hour mark, further optionally by release of about 40% to about 65% of CTN at the 8-hour mark, and further optionally by release of about 65% to about 95% of CTN at the 12-hour mark, and further optionally by such rates of release at all three time points; or
(b) optionally be characterized by release of about 24% to 48% CTN at the 3-hour mark, further optionally by release of at least 66% CTN at the 6-hour mark, further optionally by release of at least 86% of CTN at the 10-hour mark, and further optionally by such rates of release at all three time points; still further optionally, this release profile can be characterized by a release of 49% to 73% at the 4-hour mark.

C2. The pharmaceutical formulation of C1, wherein the formulation is a solid oral formulation and/or a semisolid oral formulation.

C3. The pharmaceutical formulation of C1 or C2, wherein the formulation is a solid oral formulation suitable for pediatric use.

C4. The pharmaceutical formulation of any one of C1-C3, wherein the solid oral formulation comprises one or more forms selected from powder, beads, orodispersible tablet, orodispersible film, mini-tablet, chewable tablet, and soft-chew; optionally selected from powder and beads; optionally beads.

C5. The pharmaceutical formulation of any one of C1-C4, wherein the formulation is a solid oral formulation suitable for adult use.

C6. The pharmaceutical formulation of C5, wherein the solid oral formulation comprises one or more forms selected from a tablet, capsule, sachet, powder, beads, and lozenge; optionally selected from tablet, capsule, beads, and powder; optionally selected from capsule and beads.

C7. The pharmaceutical formulation of any one of C1-C6, wherein the solid oral formulation comprises a plurality of centanafadine (CTN) beads, the plurality of CTN beads each comprising a core particle comprising CTN or a pharmaceutically acceptable salt thereof and an excipient.

B1. The pharmaceutical formulation of any one of C1-C7, or D1 or D2, or E1-E7, or F1 comprising CTN or a pharmaceutically acceptable salt thereof, wherein the formulation is a solid oral formulation suitable for pediatric use.

B2. The pharmaceutical formulation of B1, wherein the solid oral formulation suitable for pediatric use is selected from one or more types comprising beads, orodispersible tablet, orodispersible film, mini-tablet, chewable tablet, and soft-chew, optionally beads.

B3. The pharmaceutical formulation of any one of B1 or B2, wherein the solid oral formulation suitable for pediatric use is characterized by one or more release profiles, in vivo and/or in vitro, selected from immediate release, sustained release, delayed release, and delayed-sustained release.

B4. The pharmaceutical formulation of any one of B1-B3, wherein the solid oral formulation suitable for pediatric use comprises a plurality of centanafadine (CTN) beads, the plurality of CTN beads each comprising a core particle comprising CTN or a pharmaceutically acceptable salt thereof and an excipient.

B5. The pharmaceutical formulation of B4, wherein at least a portion of the plurality of beads are coated.

B6. The pharmaceutical formulation of any one of B4-B5, wherein at least a portion of the plurality of beads are not coated.

B7. The pharmaceutical formulation of B6, wherein the coating is one or more coatings selected from a delayed release coating, a sustained release coating, and a delayed-sustained release coating.

B8. The pharmaceutical formulation of B7, wherein the coating is a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer;
  optionally one or more materials selected from a copolymer of methacrylic acid, methyl methacrylate, and methyl acrylate, and a methacrylic acid-acrylate copolymer; and optionally a copolymer of methacrylic acid, methyl methacrylate, and methyl acrylate.

B9. The pharmaceutical formulation of any one of B4-B8 comprising a delayed release coating, wherein the median amount of delayed release coating disposed over the core particle is at least 10 wt. % of the total weight of the CTN bead, or in a range of about 12 wt. % to about 50 wt. %, or about 12 wt. % to about 35 wt. %, based on the total weight of the CTN bead.

B10. The pharmaceutical formulation of any one of B4-B9 comprising a sustained release coating, wherein the sustained release coating comprising one or more materials selected from an alkylcellulose, acrylic acid polymer, a methacrylic acid polymer, an acrylic acid copolymer, a methacrylic acid copolymer, and a cellulose ether;
  optionally one or more materials selected from a hydroxyalkylcellulose, a carboxyalkylcellulose, a methyl methacrylate, a methyl methacrylate copolymer, an ethoxyethyl methacrylate, an ethyl acrylate, a trimethyl ammonioethyl methacrylate, a cyanoethyl methacrylate, an aminoalkyl methacrylate copolymer, a poly(acrylic acid), a poly(methacrylic acid), a methacrylic acid alkylamine copolymer, a poly(methyl methacrylate), a poly(methacrylic acid)(anhydride), a polymethacrylate, polyacrylamide, a poly(methacrylic acid anhydride), and a glycidyl methacrylate copolymer;
  optionally one or more materials selected from poly[ethyl acrylate, methyl methacrylate, trimethylammonioethyl methacrylate chloride], hydroxypropylmethylcellulose, and poly[ethyl acrylate, methyl methacrylate];
  optionally poly[ethyl acrylate, methyl methacrylate].

B11. The pharmaceutical formulation of any one of B4-B10 comprising a sustained release coating, wherein the median amount of sustained release coating disposed over the core particle is at least 5 wt. % of the total weight of the core particle, or in a range of about 5 wt. % to about 60 wt. %, or about 15 wt. % to about 60 wt. %, or about 20 wt. % to about 50 wt. % of the total weight of the core particle.

B12. The pharmaceutical formulation of any one of B4-B11 comprising a coating, wherein the coating further comprises a pore former.

B13. The pharmaceutical formulation of B12, wherein the pore former comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide, optionally one or more materials selected from hydroxypropyl methylcellulose, hydroxypropylcellulose, and polyvinylpyrrolidone;
  optionally hydroxypropyl methylcellulose.

B14. The pharmaceutical formulation of B12, wherein the pore former is present in the coating in an amount in a range of about 5 wt. % or more, or about 10 wt. % or more, or about 5 wt. % to about 20 wt. %; optionally 15 wt. %.

B15. The pharmaceutical formulation of any one of the B4-B14, wherein the core particles are characterized by having a distribution of particles sizes, and at least a portion of the core particles of the plurality of beads have a core particle size (maximum diameter) of about 0.2 mm to about 2 mm, or about 0.3 mm to about 1.5 mm, 0.4 mm to about 1.5 mm, or about 0.5 mm to about 1 mm, or about 0.5 mm to 0.85 mm, or about 0.5 mm to about 0.71 mm.

B16. The pharmaceutical formulation of B15, wherein the distribution of particles sizes of the core particles is characterized by at least 60% by weight of the core particles having a particle size (maximum diameter) in a range of about 0.4 mm to about 1.5 mm, or about 0.5 mm to about 1 mm, or about 0.5 mm to 0.85 mm, or about 0.5 mm to about 0.71 mm, optionally at least 80% by weight of the core particles having a particle size in a range of about 0.4 mm to about 1.5 mm, or about 0.5 mm to about 1 mm, or about 0.5 mm to 0.85 mm, or about 0.5 mm to about 0.71 mm,
optionally at least 90% by weight of the core particles having a particle size in a range of about 0.4 mm to about 1.5 mm, or about 0.5 mm to about 1 mm, or about 0.5 mm to 0.85 mm, or about 0.5 mm to about 0.71 mm,
optionally at least 99% by weight of the core particles having a particle size in a range of about 0.4 mm to about 1.5 mm, or about 0.5 mm to about 1 mm, or about 0.5 mm to 0.85 mm, or about 0.5 mm to about 0.71 mm.

B17. The pharmaceutical dosage form of any one of B4-B16, wherein the plurality of CTN beads have a median particle size (diameter) in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm, or about 0.5 mm to about 0.71 mm.

B18. The pharmaceutical formulation of any one of B4-B17, wherein the plurality of CTN beads comprises one or more types selected from: an immediate release bead, a sustained release bead, a delayed release bead, and a delayed-sustained release bead.

B19. The pharmaceutical formulation of any one of B4-B18, wherein the plurality of beads comprises a mixture of one or more immediate release beads and one or more sustained release beads.

B20. The pharmaceutical formulation of B19, wherein the ratio of CTN or pharmaceutically acceptable salt thereof is present in the one or more immediate release beads and one or more sustained release beads at a ratio in a range of about 1:100 to about 1:1 parts by weight based on the weight of CTN.

B21. The pharmaceutical formulation of any one of B4-B20, wherein the plurality of beads comprises a mixture of one or more immediate release beads and one or more delayed release beads.

B22. The pharmaceutical formulation of B21, wherein the ratio of CTN or pharmaceutically acceptable salt thereof is present in the one or more immediate release beads and one or more delayed release beads at a ratio in a range of about 1:100 to about 1:1 parts by weight based on the weight of CTN.

B23. The pharmaceutical formulation of any one of B4-B22, wherein the plurality of beads comprises a mixture of one or more delayed release beads and one or more sustained release beads.

B24. The pharmaceutical formulation of B23, wherein the ratio of CTN or pharmaceutically acceptable salt thereof is present in the one or more sustained release beads and one or more delayed release beads at a ratio in a range of about 5:10 to about 1:5 parts by weight based on the weight of CTN.

B25. The pharmaceutical formulation of any one of B4-B24, wherein the plurality of beads comprises a mixture of one or more immediate release beads and one or more delayed-sustained release beads.

B26. The pharmaceutical formulation of B25, wherein the ratio of CTN or pharmaceutically acceptable salt thereof is present in the one or more immediate release beads and one or more delayed-sustained release beads at a ratio in a range of about 1:100 to about 1:1 parts by weight based on the weight of CTN.

B27. The pharmaceutical formulation of any one of B4-B26, wherein the plurality of beads comprises a mixture of one or more immediate release beads, one or more sustained release beads, and one or more delayed release beads.

B28. The pharmaceutical formulation of B27, wherein the ratio of CTN or pharmaceutically acceptable salt thereof is present in the one or more immediate release beads, one or more sustained release beads, and one or more delayed release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-1:3:3-6:3-6 parts by weight based on the weight of the CTN or salt thereof; and,
optionally a ratio in a range of about 0.7-1:5-15:5-15 parts by weight based on the weight of the CTN or salt thereof.

B29. The pharmaceutical formulation of any one of B4-B28, wherein the plurality of beads comprises a mixture of one or more immediate release beads, one or more sustained release beads, and one or more delayed-sustained release beads.

B30. The pharmaceutical formulation of B29, wherein the ratio of CTN or pharmaceutically acceptable salt thereof is present in the one or more immediate release beads, one or more sustained release beads, and one or more delayed-sustained release beads at a ratio in a range of about 0.1-1:1-20:1-20 parts by weight based on the weight of the CTN or salt thereof;
optionally a ratio in a range of about 0.5-1:5-20:5-20 parts by weight based on the weight of the CTN or salt thereof;
optionally a ratio in a range of about 0.7-1:3:3-6:3-6 parts by weight based on the weight of the CTN or salt thereof; and,
optionally a ratio in a range of about 0.7-1:5-15:5-15 parts by weight based on the weight of the CTN or salt thereof.

B31. The pharmaceutical formulation of any one of B4-B30, wherein the immediate release bead is free of coatings.

B32. The pharmaceutical formulation of any one of B4-B31, wherein the immediate release beads are present in the formulation in an amount in a range of about 1% to about 75% based on the total weight of the plurality of CTN beads, optionally in a range of about 40% to about 55% based on the total weight of the plurality of CTN beads when the drug loading in the immediate release beads is about 5 wt. % to about wt. %;
optionally in a range of about 1% to about 50% based on the total weight of the plurality of CTN beads;
optionally in a range of about 1% to about 25% based on the total weight of the plurality of CTN beads;
optionally in a range of about 1% to about 10% based on the total weight of the plurality of CTN beads;
optionally in a range of about 9% to about 19% based on the total weight of the plurality of CTN beads when the drug loading in the immediate release beads is about 40 wt. % to about 55 wt. %; and
optionally in a range of about 18% to about 28% based on the total weight of the plurality of CTN beads.

B33. The pharmaceutical formulation of any one of B4-B32 comprising sustained release beads, wherein the sustained release beads are present in the formulation in an amount in a range of about 5% to 80% based on the total weight of the plurality of CTN beads;
  optionally in a range of about 23% to about 33% based on the total weight of the plurality of CTN beads;
  optionally in a range of about 5% to about 65% based on the total weight of the plurality of CTN beads;
  optionally in a range of about 40% to about 55% based on the total weight of the plurality of CTN beads;
  optionally in a range of about 35% to about 55% based on the total weight of the plurality of CTN beads.

B34. The pharmaceutical formulation of any one of B4-B33 comprising delayed release beads, wherein the delayed release beads are present in the formulation in an amount in a range of about 5% to 80% based on the total weight of the plurality of CTN beads;
  optionally in a range of about 21% to about 31% based on the total weight of the plurality of CTN beads;
  optionally in a range of about 5% to about 65% based on the total weight of the plurality of CTN beads;
  optionally in a range of about 36% to about 46% based on the total weight of the plurality of CTN beads;
  optionally in a range of about 30% to about 55% based on the total weight of the plurality of CTN beads.

B35. The pharmaceutical formulation of any one of B4-B34 comprising sustained release beads, wherein at least 90% of the CTN or salt thereof is released from the sustained release beads at a time in a range of 2 to 6 hours according to USP <711> using Apparatus I (basket) in 1000 ml deionized water at 37° C.+/−0.5° C. at 100 rpm.

B36. The pharmaceutical formulation of any one of B4-B35 comprising delayed release beads, wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; or wherein at least 90% of the CTN or salt thereof is released from the delayed release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B37. The pharmaceutical formulation of any one of B4-B36 comprising delayed-sustained release beads, wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; wherein at least 90% of the CTN or salt thereof is released from the delayed-sustained release beads at a time in a range of 4 to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B38. The pharmaceutical formulation of any one of B4-B37 comprising immediate release beads, wherein at least 90% of the CTN or salt thereof is released from the immediate release beads at a time in a range of 0 to 2 hours according to USP <711> using Apparatus I (basket) in 1000 ml deionized water at 37° C.+/−0.5° C. at 100 rpm.

B39. The pharmaceutical formulation of any one of B4-B38 comprising a mixture of immediate release beads, sustained release beads, and delayed release beads, wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml unbuffered deionized water for the remainder of the time; wherein at least 40% of the CTN or salt thereof is released from the mixture of beads at a time in a range of 3 hours to 5 hours, and at least 90% of the CTN or salt thereof is released from the mixture of beads at a time in a range of 12 hours to 14 hours according to USP <711> with Apparatus 1 (basket) at 37° C.+/−0.5° C. at 100 rpm, first in 1000 ml of a 0.1N HCl solution for 2 hours, then 1000 ml pH 7.4 phosphate buffered water for the remainder of the time.

B40. The pharmaceutical formulation of any one of B4-B39 comprising an immediate release bead, wherein the CTN or salt thereof is present in an amount in a range of 5 wt. % to 80 wt. % in the immediate release bead based on the total weight of the immediate release bead;
  optionally in a range of 5 wt. % to 60 wt. % based on the total weight of the immediate release bead;
  optionally in a range of 5 wt. % to 15 wt. % based on the total weight of the immediate release bead;
  optionally in a range of 40 wt. % to 60 wt. % based on the total weight of the immediate release bead; and
  optionally a first immediate release bead wherein the CTN or salt thereof is present in an amount in a range of 5 wt. % to 15 wt. % based on the total weight of the immediate release bead and a second immediate release bead wherein the CTN or salt thereof is present in an amount in a range of 40 wt. % to 60 wt. % based on the total weight of the immediate release bead.

B41. The pharmaceutical formulation of any one of B4-B40 comprising a sustained release bead, wherein the CTN or salt thereof is present in an amount in a range of 10 wt. % to 95 wt. % in the sustained release bead based on the total weight of the sustained release bead;
  optionally in a range of 40 wt. % to 90 wt. % based on the total weight of the sustained release bead;
  optionally in a range of 50 wt. % to 70 wt. % based on the total weight of the sustained release bead.

B42. The pharmaceutical formulation of any one of B4-B41 comprising a delayed release bead, wherein the CTN or salt thereof is present in an amount in a range of 10 wt. % to 95 wt. % in the delayed release bead based on the total weight of the delayed release bead;
  optionally in a range of 40 wt. % to 90 wt. % based on the total weight of the delayed release bead;
  optionally in a range of 50 wt. % to 70 wt. % based on the total weight of the delayed release bead.

B43. The pharmaceutical formulation of any one of B4-B42, characterized by providing an in vivo absorption profile that is multimodal, optionally bimodal.

B44. The pharmaceutical formulation of any one of B4-B43, wherein the in vivo absorption profile has a first $C_{max}$ at a time in a range of 0 to 4.5 hours, or about 0.5 hours to about 2 hours, or about 3.5 hours to about 4.5 hours.

B45. The pharmaceutical formulation of any one of B4-B44, wherein the in vivo absorption profile has a second $C_{max}$ at a time in a range of about 6 hours to 10 hours, or about 7 hours to 9 hours, or about 7.5 to about 8.5 hours.

B46. The pharmaceutical formulation of any one of B44 or B45, wherein the first $C_{max}$ provided by the formulation in adult humans has an average plasma level in a range of about 250 ng/mL to about 420 ng/mL, or about 320 ng/mL to about 420 ng/mL, or about 325 ng/mL to about 390 ng/mL.

B47. The pharmaceutical formulation of any one of B44-B46, wherein the second $C_{max}$ provided by the formulation in adult humans has an average plasma level in a range of about 450 ng/mL to about 550 ng/mL, or about 470 ng/mL to about 530 ng/m L.

B48. The pharmaceutical formulation of any one of B4-B47, wherein the in vivo absorption profile has a first $C_{max}$ and a second $C_{max}$, wherein the first $C_{max}$ and second $C_{max}$ are separated by a time in a range of 1.5 to 8.5 hours, or about 2 hours to about 6 hours, or about 3 hours to about 5 hours.

B49. The pharmaceutical formulation of any one of B4-B48, wherein one or more of the plurality of CTN beads has a release mechanism comprising one or more of dissolution, diffusion, erosion, osmosis, partitioning, swelling, and targeting.

B50. The pharmaceutical formulation of any one of B4-B49, wherein one or more of the plurality of CTN beads has a diffusion release mechanism.

B51. The pharmaceutical formulation of any one of B4-B50, wherein one or more of the plurality of CTN beads has a pH-triggered dissolution release mechanism.

B52. The pharmaceutical formulation of any one of B4-B51, wherein one or more of the plurality of CTN beads has a combination of pH-triggered dissolution release mechanism and diffusion release mechanism.

B53. The pharmaceutical formulation of any one of B4-B52, wherein one or more of the plurality of CTN beads comprises a porous matrix comprising the CTN.

B54. The pharmaceutical formulation of any one of B4-B53, wherein the plurality of CTN beads are enclosed in one or more containers selected from a capsule, sachet, and stick-pack;
  optionally a capsule.

B55. The pharmaceutical formulation of any one of B4-B54, wherein the CTN is present as a salt; optionally as a hydrochloride salt.

B56. The pharmaceutical formulation of any one of B4-B55, wherein the excipient comprises one or more materials selected from a filler and a binder, a glidant, a surfactant, a polymer coating, and a plasticizer;
  optionally a combination of a filler and a binder;
  optionally a combination of a binder and a polymer coating;
  optionally a combination of a filler, a binder, and a polymer coating;
  optionally a combination of a filler, a binder, a polymer coating, and a plasticizer.

B57. The pharmaceutical formulation of any one of B4-B55, wherein the excipient comprises one or more materials selected from lactose, mannitol, corn starch, microcrystalline cellulose, hydroxypropyl cellulose, hypromellose, polyvinyl pyrrolidone, talc, polysorbate 80, glycerol monostearate, triethyl citrate, polyvinyl alcohol-polyethylene glycol graft copolymer, and silica.

B58. The pharmaceutical formulation of any one of B4-B57, wherein the formulation is free of disintegrants.

Aspect G

G1. A method of treatment using a formulation according to any one of the foregoing Aspects, or use of a formulation according to any one of the foregoing Aspects, comprising administering a formulation according to any one of the foregoing Aspects to an animal subject in need thereof, optionally a mammalian subject in need thereof, optionally a human in need thereof.

G2. The method of G1, wherein the subject in need thereof is a subject in need of modulation of plasma levels of centanafadine or a pharmaceutically acceptable salt thereof.

G3. The method of G1 or G2, wherein the administration is to treat or prevent one or more symptoms of a disorder alleviated by inhibiting reuptake of one or more of norepinephrine, dopamine reuptake, or serotonin.

G4. The method of any one of G1-G3, wherein the subject in need thereof has attention-deficit/hyperactivity disorder (ADHD).

G5. The method of G4, wherein the ADHD is predominantly inattentive type.

G6. The method of G4, wherein the ADHD is predominantly hyperactive-impulsive type.

G7. The method of G4, wherein the ADHD is combined type.

G8. The method of any one of G1-G7, wherein the subject in need thereof has an autism spectrum disorder and a fragile X-associated disorder.

G9. The method of any one of G1-G8, wherein the subject in need thereof has a fragile X-associated disorder G10. The method of G9, wherein the fragile X-associated disorder is fragile X syndrome (FXS).

G11. The method of G9, wherein the fragile X-associated disorder is fragile X-associated tremor/ataxia syndrome (FXTAS).

G12. The method of G9, wherein the fragile X-associated disorder is fragile X-associated primary ovarian insufficiency (FXPOI).

G13. The method of any one of G1-G12, wherein the subject in need thereof has a binge eating disorder.

G14. The method of G13, wherein the binge eating disorder comprises 1-3 binge episodes weekly; or 4-7 binge episodes weekly, or 8-13 binge episodes weekly, or 14 or more binge episodes weekly.

G15. The method of any one of G1-G14, wherein the administration is on a schedule of twice per day or less.

G16. The method of G19, wherein the administration is on a schedule of once per day.

G17. The method of any one of G1-G16, wherein the formulation or dosage form is administered in an amount in a range of 0.5 mg/kg to 20 mg/kg per day,
  optionally 1 mg/kg to 15 mg/kg per day;
  optionally 1 mg/kg to 10 mg/kg per day;
  optionally 2 mg/kg to 20 mg/kg per day;
  optionally 2 mg/kg to 10 mg/kg per day,
  optionally 3 mg/kg to 15 mg/kg per day.

G18. The method of any one of G1-G17, wherein the formulation is administered in an amount in a range of about 10 mg to about 25 mg;
  optionally about 30 mg to about 50 mg;
  optionally about 25 mg to about 150 mg;
  optionally about 50 mg to about 100 mg;
  optionally about 100 mg to about 250 mg;
  optionally about 250 to about 500 mg, one, two, three, or four times per day.

G19. The method of G18, wherein the formulation is administered in an amount in a range of about 50 mg to 75 mg;
  optionally about 100 mg to 200 mg;
  optionally about 250 mg to 400 mg;
  optionally about 400 mg to 600 mg once or twice daily.

G20. The method of G19, wherein the formulation is administered in an amount in a range of about 100 mg to 300 mg once daily.

G21. The method of any one of G1-G20, wherein the administration comprises combining the formulation with a soft food substance prior to administration; optionally wherein the soft food substance comprises one or more foods selected from applesauce, yogurt, pudding, and jelly.

G22. The method of any one of G1-G21, wherein the administration is via an enteral feeding tube.

G23. The method of any one of G1-G22, wherein the formulation is administered to the subject in a fasted state.

G24. The method of any one of G1-G23, wherein the administration provides an adult subject with a maximum centanafadine plasma concentration in a dose interval ($C_{max}$) of at least 200 ng/mL, or at least 250 ng/mL, or at least 300 ng/mL, or at least 340 ng/mL, or in a range of about 250 ng/mL to about 1500 ng/mL, or about 310 ng/mL to about 1300 ng/mL, or about 325 to about 1250 ng/mL, or about 340 ng/mL to about 1190 ng/mL, or about 400 ng/mL to about 850 ng/mL.

G25. The method of any one of G1-G24, wherein the administration provides a subject with a centanafadine plasma concentration at 1 hour post-dose ($C_{1h}$) of at least 150 ng/mL, or at least 200 ng/mL, or at least 250 ng/mL, or at least 280 ng/mL, or in a range of about 180 ng/mL to about 610 ng/mL, or about 200 ng/mL to about 590 ng/mL, or about 220 ng/mL to about 540 ng/mL, or about 245 ng/mL to about 490 ng/mL.

G26. The method of any one of G1-G25, wherein the administration provides an adult subject with a concentration of centanafadine in the plasma at 12 hours after administration ($C_{12h}$) of at least 95 ng/mL, or at least 160 ng/mL, or at least 230 ng/mL, or at least 360 ng/mL, or in a range of about 95 ng/mL to about 450 ng/mL, or about 100 ng/mL to about 435 ng/mL, or about 110 ng/mL to about 400 ng/mL, or about 30 ng/mL to about 360 ng/mL, or about 150 ng/mL to about 300 ng/mL.

G27. The method of any one of G1-G26, wherein the administration provides an adult subject with a concentration of centanafadine in the plasma at 16 hours after administration ($C_{16h}$) of less than 300 ng/mL, or less 250 ng/mL, or less than 230 ng/mL, or less than 200 ng/mL, or less than 100 ng/mL, or in a range of about 95 ng/mL to about 450 ng/mL, or about 100 ng/mL to about 300 ng/mL, or about 110 ng/mL to about 250 ng/mL, or about 30 ng/mL to about 250 ng/mL, or about 60 ng/mL to about 150 ng/mL.

G28. The method of any one of G1-G27, wherein the administration provides an adult subject with a centanafadine plasma concentration post-dose which remains at least ng/mL, or at least 200 ng/mL, or at least 250 ng/mL, or at least 280 ng/mL, or in a range of about 75 ng/mL to about 1500 ng/mL, or about 200 ng/mL to about 1440 ng/mL, or about 230 ng/mL to about 1320 ng/mL, or about 250 ng/mL to about 1260 ng/mL over the time period 2 to 8 hours post-dose.

G29. The method of any one of G1-G28, wherein the administration provides an adult subject with a cumulative centanafadine plasma exposure in a subject at 1 hour post-dose ($AUC_{0-1h}$) of at least 30 ng·h/mL, or at least 40 ng·h/mL, or at least 100 ng·h/mL, or at least 200 ng·h/mL, or in a range of about 30 ng·h/mL to about 500 ng·h/mL, or about 32 ng·h/mL to about 480 ng·h/mL, or about 36 ng·h/mL to about 440 ng·h/mL, or about 40 ng·h/mL to about 400 ng·h/mL, or about 350 ng·h/mL to about 450 ng·h/mL.

G30. The method of any one of G1-G29, wherein the administration provides an adult subject with a cumulative centanafadine plasma exposure over the time period 0-8 hours post-dose ($AUC_{0-8h}$) of at least 1275 ng·h/mL, or at least 1530 ng·h/mL, or at least 1700 ng·h/mL, or at least 2500 ng·h/mL, or in a range of about 1275 ng·h/mL to about 6250 ng·h/mL, or about 1275 ng·h/mL to about 6250 ng·h/mL, or about 1360 ng·h/mL to about 6000 ng·h/mL, or about 1530 ng·h/mL to about 5500 ng·h/mL, or about 1700 ng·h/mL to about 5000 ng·h/mL, or about 2100 ng·h/mL to about 4100 ng·h/mL.

G31. The method of any one of G1-G30, wherein the administration provides an adult subject with a cumulative centanafadine plasma exposure over the time period 2-8 hours post-dose ($AUC_{2-8h}$) of at least 1050 ng·h/mL, or at least 1120 ng·h/mL, or at least 1330 ng·h/mL, or at least 2000 ng·h/mL, or at least 2500 ng·h/mL, or in a range of about 1050 ng·h/mL to about 5250 ng·h/mL, or about 1120 ng·h/mL to about 5040 ng·h/mL, or about 1260 ng·h/mL to about 4620 ng·h/mL, or about 1330 ng·h/mL to about 4410 ng·h/mL, or about 1400 ng·h/mL to about 4200 ng·h/mL, or about 1700 ng·h/mL to about 3500 ng·h/mL.

G32. The method of any one of G1-G31, wherein the administration provides an adult subject with a cumulative centanafadine plasma exposure in the 24-hour period after administration ($AUC_{0-24h}$) of at least 2400 ng·h/mL, or at least 2880 ng·h/mL, or at least 3200 ng·h/mL, or at least 5000 ng·h/mL, or at least 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL, or about 4000 ng·h/mL to about 6000 ng·h/mL.

G33. The method of any one of G1-G32, wherein the administration provides an adult subject with a cumulative centanafadine plasma exposure in the 48-hour period after administration ($AUC_{0-48h}$) of at least 2400 ng·h/mL, or 2880 ng·h/mL, or 3200 ng·h/mL, 5000 ng·h/mL, or 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL.

G34. The method of any one of G1-G33, wherein the administration provides an adult subject with a cumulative centanafadine plasma exposure in the period after administration ($AUC_{0-inf}$) of at least 2400 ng·h/mL, or 2880 ng·h/mL, or 3200 ng·h/mL, 5000 ng·h/mL, or 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL.

G35. The method of any one of G1-G34, wherein the administration comprises administering a CTN dose of 164.4 mg CTN per day.

G36. The method of any one of G1-G23, wherein the administration provides an adult subject with a subject with a maximum centanafadine plasma concentration in a dose interval ($C_{max}$) of at least about 525 ng/mL, or at least about 560 ng/mL, or at least about 700 ng/mL, or at least about 1000 ng/mL, or at least about 1600 ng/mL, or in a range of about 525 ng/mL to about 4000 ng/mL, or about 560 ng/mL to about 3840 ng/mL, or about 630 ng/mL to about 3520 ng/mL, or about 6650 ng/mL to about 700 ng/mL, or about 3200 ng/mL.

G37. The method of any one of G1-G23 or G36, wherein the administration provides an adult subject with a subject with a centanafadine plasma concentration at 1 hour post-dose ($C_{1h}$) of at least 225 ng/mL, or at least 250 ng/mL, or at least 285 ng/mL, or at least 300 ng/mL, or in a range of about 225 ng/mL to about 1375 ng/mL, or about 240 ng/mL to about 1320 ng/mL, or about 285 ng/mL to about 1155 ng/mL, or about 300 ng/mL to about 1100 ng/mL.

G38. The method of any one of G1-G23 or G36-G37, wherein the administration provides an adult subject with a concentration of centanafadine in the plasma at 12 hours after administration ($C_{12h}$) of at least 190 ng/mL, or at least 225 ng/mL, or at least 250 ng/mL, or at least 400 ng/mL, or in a range of about 190 ng/mL to about 1250 ng/mL, or about 200 ng/mL to about 1200 ng/mL, or about 225 ng/mL to about 1100 ng/mL, or about 250 ng/mL to about 1000 ng/mL.

G39. The method of any one of G1-G23 or G36-G38, wherein the administration provides an adult subject with a concentration of centanafadine in the plasma at 16 hours after administration ($C_{16h}$) of less than 375 ng/mL, or less than 300 ng/mL, or less 250 ng/mL, or less than 230 ng/mL, or less than 200 ng/mL, or less than 100 ng/mL, or in a range of about 60 ng/mL to about 375 ng/mL, or about 64 ng/mL to about 300 ng/mL, or about 76 ng/mL to about 250 ng/mL, or about 80 ng/mL to about 300 ng/mL.

G40. The method of any one of G1-G23 or G36-G39, wherein the administration provides an adult subject with a centanafadine plasma concentration post-dose which remains at least at least 200 ng/mL, or at least 250 ng/mL, or at least 280 ng/mL, or at least 300 ng/mL, or at least 1000 ng/mL, or at least 1500 ng/mL, or in a range of about 150 ng/mL to about 4125 ng/mL, or about 160 ng/mL to about 3960 ng/mL, or about 180 ng/mL to about 3630 ng/mL, or about 200 ng/mL to about 3300 ng/mL over the time period 2 to 8 hours post-dose.

G41. The method of any one of G1-G23 or G36-G40, wherein the administration provides an adult subject with a cumulative centanafadine plasma exposure in a subject at 1 hour post-dose ($AUC_{0-1h}$) of at least 60 ng·h/mL, or at least 80 ng·h/mL, or at least 200 ng·h/mL, or at least 300 ng·h/mL, or in a range of about 60 ng·h/mL to about 750 ng·h/mL, or about 64 ng·h/mL to about 720 ng·h/mL, or about 72 ng·h/mL to about 660 ng·h/mL, or about 80 ng·h/mL to about 600 ng·h/mL.

G42. The method of any one of G1-G23 or G36-G41, wherein the administration provides an adult subject with a cumulative centanafadine plasma exposure over the time period 0-8 hours post-dose ($AUC_{0-8h}$) of at least 2250 ng·h/mL, or at least 3000 ng·h/mL, or at least 5000 ng·h/mL, or at least 6000 ng·h/mL, or in a range of about 2250 ng·h/mL to about 13750 ng·h/mL, or about 2400 ng·h/mL to about 13200 ng·h/mL, or about 72700 ng·h/mL to about 12100 ng·h/mL, or about 3000 ng·h/mL to about 11000 ng·h/mL.

G43. The method of any one of G1-G23 or G36-G42, wherein the administration provides an adult subject with a cumulative centanafadine plasma exposure over the time period 2-8 hours post-dose ($AUC_{2-8h}$) of at least 1875 ng·h/mL, or at least 2500 ng·h/mL, or at least 3000 ng·h/mL, or at least 4000 ng·h/mL, or at least 5000 ng·h/mL, or in a range of about 1875 ng·h/mL to about 11250 ng·h/mL, or about 2000 ng·h/mL to about 10800 ng·h/mL, or about 2250 ng·h/mL to about 9900 ng·h/mL, or about 2375 ng·h/mL to about 9450 ng·h/mL, or about 2500 ng·h/mL to about 9000 ng·h/mL.

G44. The method of any one of G1-G23 or G36-G43, wherein the administration provides an adult subject with a cumulative centanafadine plasma exposure in the 24-hour period after administration ($AUC_{0-24h}$) of at least 10950 ng·h/mL, or at least 11680 ng·h/mL, or at least 14600 ng·h/mL, or at least 16000 ng·h/mL, or at least 19000 ng·h/mL, or in a range of about 10950 ng·h/mL to about 30000 ng·h/mL, or about 11680 ng·h/mL to about 28800 ng·h/mL, or about 13140 ng·h/mL to about 26400 ng·h/mL, or about 13870 ng·h/mL to about 25200 ng·h/mL, or about 14600 ng·h/mL to about 24000 ng·h/mL.

G45. The method of any one of G1-G23 or G36-G44, wherein the administration provides an adult subject with a cumulative centanafadine plasma exposure in the period after administration ($AUC_{0-inf}$) of at least 10950 ng·h/mL, or at least 11680 ng·h/mL, or at least 14600 ng·h/mL, or at least 16000 ng·h/mL, or at least 19000 ng·h/mL, or in a range of about 10950 ng·h/mL to about 30000 ng·h/mL, or about 11680 ng·h/mL to about 28800 ng·h/mL, or about 13140 ng·h/mL to about 26400 ng·h/mL, or about 13870 ng·h/mL to about 25200 ng·h/mL, or about 14600 ng·h/mL to about 25000 ng·h/mL.

G46. The method of any one of G1-G19, G21-G23, or G36-G45, wherein the administration comprises administering a centanafadine dose of 328.8 mg CTN per day.

G47. The method of any one of G1-G47, wherein the administration provides an adult subject with a ratio of centanafadine plasma concentration at 16 hours after administration to the centanafadine plasma concentration at 12 hours after administration ($C_{16h}/C_{12h}$) of less than 1, or 0.75 or less. or 0.5 or less or 0.3 or less, or in a range of about to about 0.25, or about 0.5 to about 0.1.

G48. The method of any one of G1-G47, wherein the administration provides an adult subject with a time until maximum centanafadine plasma concentration ($t_{max}$) in a range of about 1.5 hours to about 11 hours, or about 2.25 hours to about 10 hours, or about 2.7 hours to about 8.8 hours, or about 3 hours to about 8 hours, or about 4 hours to about 6 hours.

Aspect H

H1. A method of making a pharmaceutical formulation comprising centanafadine (CTN) or a pharmaceutically acceptable salt thereof, the method comprising compounding the CTN or pharmaceutically acceptable salt thereof with a binder to make particles comprising CTN or pharmaceutically acceptable salt thereof having a defined particle size range, and disposing a coating over at least a portion of the particles.

H2. The method of H1, wherein the compounding comprises extrusion; optionally wherein the compounding further comprises spheronization after extrusion.

H3. The method of any one of H1-H2, wherein the median size of the particles is in a range of about 0.2 mm to about 2 mm, 0.4 mm to about 1.5 mm, or about 0.5 mm to about 1 mm, or about 0.5 mm to 0.85 mm.

Aspect I

I1. A pharmaceutical formulation of any one of the foregoing aspects A to F, wherein the formulation provides an adult subject with maximum CTN plasma concentration in a dose interval ($C_{max}$) of at least 200 ng/mL, or at least 250 ng/mL, or at least 300 ng/mL, or at least 340 ng/mL, or in a range of about 250 ng/mL to about 1500 ng/mL, or about 310 ng/mL to about 1300 ng/mL, or about 325 to about 1250 ng/mL, or about 340 ng/mL to about 1190 ng/mL.

I2. The pharmaceutical formulation of I1, wherein the formulation provides an adult subject with a CTN plasma concentration at 1 hour post-dose ($C_{1h}$) of at least 150 ng/mL, or at least 200 ng/mL, or at least 250 ng/mL, or at least 280 ng/mL, or in a range of about 180 ng/mL to about 610 ng/mL, or about 200 ng/mL to about 590 ng/mL, or about 220 ng/mL to about 540 ng/mL, or about 245 ng/mL to about 490 ng/mL.

I3. The pharmaceutical formulation of any one of I1-I2, wherein the formulation provides an adult subject with a concentration of CTN in the plasma at 12 hours after administration ($C_{12h}$) of at least 95 ng/mL, or at least 160 ng/mL, or at least 230 ng/mL, or at least 360 ng/mL, or in a range of about 95 ng/mL to about 450 ng/mL, or about 100 ng/mL to about 435 ng/mL, or about 110 ng/mL to about 400 ng/mL, or about 30 ng/mL to about 360 ng/mL.

I4. The pharmaceutical formulation of any one of I1-I3, wherein the formulation provides an adult subject with a concentration of CTN in the plasma at 16 hours after administration ($C_{16h}$) of less than 300 ng/mL, or less 250 ng/mL, or less than 230 ng/mL, or less than 200 ng/mL, or less than 100 ng/mL, or in a range of about 95 ng/mL to about 450 ng/mL, or about 100 ng/mL to about 300 ng/mL, or about 110 ng/mL to about 250 ng/mL, or about 30 ng/mL to about 250 ng/mL.

I5. The pharmaceutical formulation of any one of I1-I4, wherein the formulation provides an adult subject with a CTN plasma concentration post-dose which remains at least ng/mL, or at least 200 ng/mL, or at least 250 ng/mL, or at least 280 ng/mL, or in a range of about 75 ng/mL to about 1500 ng/mL, or about 200 ng/mL to about 1440 ng/mL, or about 230 ng/mL to about 1320 ng/mL, or about 250 ng/mL to about 1260 ng/mL over the time period 2 to 8 hours post-dose.

I6. The pharmaceutical formulation of any one of I1-I5, wherein the formulation provides an adult subject with a cumulative CTN plasma exposure in a subject at 1 hour post-dose ($AUC_{0-1h}$) of at least 30 ng·h/mL, or at least 40 ng·h/mL, or at least 100 ng·h/mL, or at least 200 ng·h/mL, or in a range of about 30 ng·h/mL to about 500 ng·h/mL, or about 32 ng·h/mL to about 480 ng·h/mL, or about 36 ng·h/mL to about 440 ng·h/mL, or about 40 ng·h/mL to about 400 ng·h/mL.

I7. The pharmaceutical formulation of any one of I1-I6, wherein the formulation provides an adult subject with a cumulative CTN plasma exposure over the time period 0-8 hours post-dose ($AUC_{0-8h}$) of at least 1275 ng·h/mL, or at least 1530 ng·h/mL, or at least 1700 ng·h/mL, or at least 2500 ng·h/mL, or in a range of about 1275 ng·h/mL to about 6250 ng·h/mL, or about 1275 ng·h/mL to about 6250 ng·h/mL, or about 1360 ng·h/mL to about 6000 ng·h/mL, or about 1530 ng·h/mL to about 5500 ng·h/mL, or about 1700 ng·h/mL to about 5000 ng·h/mL.

I8. The pharmaceutical formulation of any one of I1-I7, wherein the formulation provides an adult subject with a cumulative plasma exposure over the time period 2-8 hours post-dose ($AUC_{2-8h}$) of at least 1050 ng·h/mL, or at least 1120 ng·h/mL, or at least 1330 ng·h/mL, or at least 2000 ng·h/mL, or at least 2500 ng·h/mL, or in a range of about 1050 ng·h/mL to about 5250 ng·h/mL, or about 1120 ng·h/mL to about 5040 ng·h/mL, or about 1260 ng·h/mL to about 4620 ng·h/mL, or about 1330 ng·h/mL to about 4410 ng·h/mL, or about 1400 ng·h/mL to about 4200 ng·h/mL.

I9. The pharmaceutical formulation of any one of I1-I8, wherein the formulation provides an adult subject with a cumulative CTN plasma exposure in the 24-hour period after administration ($AUC_{0-24h}$) of at least 2400 ng·h/mL, or at least 2880 ng·h/mL, or at least 3200 ng·h/mL, or at least 5000 ng·h/mL, or at least 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL.

I10. The pharmaceutical formulation of any one of I1-I9, wherein the formulation provides an adult subject with a cumulative CTN plasma exposure in the 24-hour period after administration ($AUC_{0-48h}$) of at least 2400 ng·h/mL, or 2880 ng·h/mL, or 3200 ng·h/mL, 5000 ng·h/mL, or 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL.

I11. The pharmaceutical formulation of any one of I1-I10, wherein the formulation provides an adult subject with a cumulative CTN plasma exposure in the 24-hour period after administration ($AUC_{0-inf}$) of at least 2400 ng·h/mL, or 2880 ng·h/mL, or 3200 ng·h/mL, 5000 ng·h/mL, or 7100 ng·h/mL, or in a range of about 2400 ng·h/mL to about 12500 ng·h/mL, or about 2560 ng·h/mL to about 12000 ng·h/mL, or about 2880 ng·h/mL to about 11000 ng·h/mL, or about 3040 ng·h/mL to about 10500 ng·h/mL, or about 3200 ng·h/mL to about 10000 ng·h/mL, or about 7000 ng·h/mL to about 10000 ng·h/mL.

I12. The pharmaceutical formulation of any one of I1-I11, wherein the formulation comprises CTN or a pharmaceutically acceptable salt thereof in an amount in a range of about 145 mg to about 185 mg CTN, or 164.4 mg.

I13. The pharmaceutical formulation of any one of the foregoing aspects A to F, wherein the formulation provides an adult subject with a maximum CTN plasma concentration in a dose interval ($C_{max}$) of at least about 525 ng/mL, or at least about 560 ng/mL, or at least about 700 ng/mL, or at least about 1000 ng/mL, or at least about 1600 ng/mL, or in a range of about 525 ng/mL to about 4000 ng/mL, or about 560 ng/mL to about 3840 ng/mL, or about 630 ng/mL to about 3520 ng/mL, or about 6650 ng/mL to about 700 ng/mL, or about 3200 ng/mL.

I14. The pharmaceutical formulation of I13, wherein the formulation provides an adult subject with a subject with a CTN plasma concentration at 1 hour post-dose ($C_{1h}$) of at least 225 ng/mL, or at least 250 ng/mL, or at least 285 ng/mL, or at least 300 ng/mL, or in a range of about 225 ng/mL to about 1375 ng/mL, or about 240 ng/mL to about 1320 ng/mL, or about 285 ng/mL to about 1155 ng/mL, or about 300 ng/mL to about 1100 ng/mL.

I15. The pharmaceutical formulation of any one of I13-I14, wherein the formulation provides an adult subject with a concentration of CTN in the plasma at 12 hours after administration ($C_{12h}$) of at least 190 ng/mL, or at least 225 ng/mL, or at least 250 ng/mL, or at least 400 ng/mL, or in a range of about 190 ng/mL to about 1250 ng/mL, or about 200 ng/mL to about 1200 ng/mL, or about 225 ng/mL to about 1100 ng/mL, or about 250 ng/mL to about 1000 ng/mL.

I16. The pharmaceutical formulation of any one of I13-I15, wherein the formulation provides an adult subject with a concentration of CTN in the plasma at 16 hours after administration ($C_{16h}$) of less than 375 ng/mL, or less than 300 ng/mL, or less 250 ng/mL, or less than 230 ng/mL, or less than 200 ng/mL, or less than 100 ng/mL, or in a range of about 60 ng/mL to about 375 ng/mL, or about 64 ng/mL to about 300 ng/mL, or about 76 ng/mL to about 250 ng/mL, or about 80 ng/mL to about 300 ng/mL.

I17. The pharmaceutical formulation of any one of I13-I16, wherein the formulation provides an adult subject with a CTN plasma concentration post-dose which remains at least at least 200 ng/mL, or at least 250 ng/mL, or at least 280 ng/mL, or at least 300 ng/mL, or at least 1000 ng/mL, or at least 1500 ng/mL, or in a range of about 150 ng/mL to about 4125 ng/mL, or about 160 ng/mL to about 3960 ng/mL, or about 180 ng/mL to about 3630 ng/mL, or about 200 ng/mL to about 3300 ng/mL over the time period 2 to 8 hours post-dose.

I18. The pharmaceutical formulation of any one of I13-I17, wherein the formulation provides an adult subject with a cumulative CTN plasma exposure in a subject at 1 hour post-dose ($AUC_{0-1h}$) of at least 60 ng·h/mL, or at least 80 ng·h/mL, or at least 200 ng·h/mL, or at least 300 ng·h/mL, or in a range of about 60 ng·h/mL to about 750 ng·h/mL, or about 64 ng·h/mL to about 720 ng·h/mL, or about 72 ng·h/mL to about 660 ng·h/mL, or about 80 ng·h/mL to about 600 ng·h/mL.

I19. The pharmaceutical formulation of any one of I13-I18, wherein the formulation provides an adult subject with a cumulative CTN plasma exposure over the time period 0-8 hours post-dose ($AUC_{0-8h}$) of at least 2250 ng·h/mL, or at least 3000 ng·h/mL, or at least 5000 ng·h/mL, or at least 6000 ng·h/mL, or in a range of about 2250 ng·h/mL to about 13750 ng·h/mL, or about 2400 ng·h/mL to about 13200 ng·h/mL, or about 72700 ng·h/mL to about 12100 ng·h/mL, or about 3000 ng·h/mL to about 11000 ng·h/mL.

I20. The pharmaceutical formulation of any one of I13-I19, wherein the formulation provides an adult subject with a cumulative plasma exposure over the time period 2-8 hours post-dose ($AUC_{2-8h}$) of at least 1875 ng·h/mL, or at least 2500 ng·h/mL, or at least 3000 ng·h/mL, or at least 4000 ng·h/mL, or at least 5000 ng·h/mL, or in a range of about 1875 ng·h/mL to about 11250 ng·h/mL, or about 2000 ng·h/mL to about 10800 ng·h/mL, or about 2250 ng·h/mL to about 9900 ng·h/mL, or about 2375 ng·h/mL to about 9450 ng·h/mL, or about 2500 ng·h/mL to about 9000 ng·h/mL.

I21. The pharmaceutical formulation of any one of I13-I20, wherein the formulation provides an adult subject with a cumulative CTN plasma exposure in the 24-hour period after administration ($AUC_{0-24h}$) of at least 10950 ng·h/mL, or at least 11680 ng·h/mL, or at least 14600 ng·h/mL, or at least 16000 ng·h/mL, or at least 19000 ng·h/mL, or in a range of about 10950 ng·h/mL to about 30000 ng·h/mL, or about 11680 ng·h/mL to about 28800 ng·h/mL, or about 13140 ng·h/mL to about 26400 ng·h/mL, or about 13870 ng·h/mL to about 25200 ng·h/mL, or about 14600 ng·h/mL to about 24000 ng·h/mL.

I22. The pharmaceutical formulation of any one of I1-I21, wherein the formulation comprises CTN or a pharmaceutically acceptable salt thereof in an amount in a range of about 290 mg to about 370 mg CTN, or 328.8 mg.

I23. The pharmaceutical formulation of any one of I1-I22, wherein the formulation provides an adult subject with a ratio of plasma concentration at 16 hours after administration to the plasma concentration at 12 hours after administration ($C_{16h}/C_{12h}$) of less than 1, or 0.75 or less or 0.5 or less or 0.3 or less, or in a range of about 0.66 to about 0.25, or about 0.5 to about 0.1.

I24. The pharmaceutical formulation of any one of I1-I23, wherein the formulation provides an adult subject with a time until maximum CTN plasma concentration (t max) in a range of about 1.5 hours to about 11 hours, or about 2.25 hours to about 10 hours, or about 2.7 hours to about 8.8 hours, or about 3 hours to about 8 hours, or about 4 hours to about 6 hours.

EXAMPLES

The following examples are provided for illustration and are not intended to limit the scope of the invention.

In the examples below, CTN was formulated and administered as centanafadine HCl.

Example 1

A variety of sustained release beads and dosage forms of beads disposed in capsules were manufactured as disclosed in the tables below. The composition of the immediate release centanafadine core beads, 50 nominal wt. % CTN HCl used in these formulations are outlined in Table 1. The core beads were made by weighing out and blending the CTN HCl, microcrystalline cellulose, and mannitol, in a high shear granulator and granulating the blended mixture with purified water, extruding and spheronization to form wet beads, fluid bed drying of the core beads, and sieving the beads to retain a desired size range.

TABLE 1

| Composition of CTN HCl Core Beads | |
|---|---|
| Component | Wt. % |
| Centanafadine Hydrochloride | 49.75 |
| Microcrystalline Cellulose USP/NF, Ph. Eur, JP (Avicel ® PH-101 available from DuPont ®) | 39.8 |
| Mannitol USP/NF, Ph. Eur, JP (Pearlitol ® 50 C available from Roquette) | 9.95 |
| Talc, 194 Pharma M | 0.50 |
| Purified Water * | N/A |

* Purified water is dispensed in the manufacturing process depending on the needs of the batch size and is removed during the manufacturing process.

N/A: not applicable

Example 1A—Ethylcellulose w/ PVP Pore Former 1

The core beads as described in Table 1 above were seal coated with a hypromellose mixture to provide a more uniform substrate surface for subsequent release coating with ethylcellulose. The desired quantity of the coating dispersion/solution was sprayed using a Wurster process at a controlled set of process parameters, and then the coated beads were dried to a desired moisture content.

A coating of ethylcellulose, povidone pore former, and plasticizer was then applied over the seal coat to make sustained release beads. Application of the coating material was carried out using a fluid bed processor. The required quantity of the coating dispersion/solution was sprayed using Wurster process at a controlled set of process parameters. Coated beads were then dried to a desired moisture content and cured, then blended with the desired amount of talc. The composition of the Example 1A beads and capsules are provided in Table 2.

TABLE 2

Composition of Example 1A Capsule

| | Component | Quantity/Capsule (mg) |
|---|---|---|
| | Core Beads | 400 |
| Seal Coating | Hypromellose | 24.0 |
| | Purified Water* | N/A |
| Functional Coating | Ethylcellulose (Aquacoat ® ECD 30 D Coating) | 122 |
| | Triethyl Citrate USP/NF, Ph. Eur, JP | 30.5 |
| | Povidone USP, Ph. Eur, JP (Plasdone ® K-29/32 CAS 9003-39-8 polymer 1-vinyl-2-pyrrolidone available from Stobec) | 8.5 |
| | Purified Water* | N/A |
| Final Dosage Form (Capsules) | | |
| | Coated Beads | 585.0 |
| | Talc USP, Ph. Eur, BP, JP (Emprove ®) | 2.9 |
| | Capsugel ® HG, Size 00 ConiSnap | 1 individual capsules |

*Purified water is dispensed in the manufacturing process depending on the needs of the batch size and is removed during the manufacturing process.
N/A: not applicable Assay by HPLC confirmed that the capsules contained 100% of the intended amount of centanafadine hydrochloride, and that content uniformity met USP <905> standards.

The dissolution release of the Example 1A capsules were tested according to USP <711> using Apparatus II (paddle) in 900 ml Super-Q® water (Type1/ultrapure water, resistivity 18.2 MW·cm at 25° C.) at 37° C.+/−0.5° C. at 50 rpm. The results are shown in Table 3.

TABLE 3

| | Dissolution % | | |
|---|---|---|---|
| Sample | 2 hours | 8 hours | 14 hours |
| 1 | 12 | 65 | 92 |
| 2 | 11 | 60 | 89 |
| 3 | 12 | 62 | 89 |
| 4 | 12 | 61 | 88 |
| 5 | 13 | 64 | 91 |
| 6 | 13 | 61 | 88 |
| Average | 12 | 62 | 89 |

Example 1B—Ethylcellulose w/ PVP Pore Former 2

The core beads as described in Table 1 above were seal-coated with a hypromellose mixture to provide a more uniform substrate surface for subsequent release coating with ethylcellulose. The desired quantity of the coating dispersion/solution was sprayed using a Wurster process at a controlled set of process parameters, and then the coated beads were dried to a desired moisture content.

A coating of ethylcellulose, povidone pore former, and plasticizer was then applied over the seal coat. Application of the coating material was carried out using a fluid bed processor. The required quantity of the coating dispersion/solution was sprayed using Wurster process at a controlled set of process parameters. The coated beads were then dried to a desired moisture content and cured, then blended with the desired amount of talc. The composition of the Example 1B beads and capsules are provided in Table 4.

TABLE 4

Composition of Example 1B Capsule

| | Component | Quantity/Capsule (mg) |
|---|---|---|
| | Core Beads | 400 |
| Seal Coating | Hypromellose | 24.0 |
| | Purified Water* | N/A |
| Functional Coating | Ethylcellullose (Aquacoat ® ECD 30 D) | 93.2 |
| | Triethyl Citrate USP/NF, Ph. Eur, JP | 23.3 |
| | Povidone USP, Ph. Eur, JP (Plasdone ® K-29/32) | 6.5 |
| | Purified Water* | N/A |
| Final Dosage Form (Capsules) | | |
| | Coated Beads | 547 |
| | Talc USP, Ph. Eur, BP, JP (Emprove ®) | 2.7 |
| | Capsugel ® HG, Size 00 ConiSnap | 1 individual capsules |

*Purified water is dispensed in the manufacturing process depending on the needs of the batch size and is removed during the manufacturing process
N/A: not applicable Assay by HPLC confirmed that the capsules contained 103% of the intended amount of centanafadine hydrochloride, and that content uniformity met the United States Pharmacopoeia (USP)<905> standards.

The dissolution release of the Example 1B capsules were tested according to USP <711> using Apparatus II (paddle) in 900 ml Super-Q® water (Type1/ultrapure water, resistivity 18.2 MW·cm at 25° C.) at 37° C.+/−0.5° C. at 50 rpm. The results are shown in Table 5.

TABLE 5

| | Dissolution % | | |
|---|---|---|---|
| Sample | 2 hours | 8 hours | 14 hours |
| 1 | 21 | 74 | 97 |
| 2 | 21 | 75 | 99 |
| 3 | 22 | 75 | 97 |
| 4 | 25 | 80 | 101 |
| 5 | 22 | 75 | 98 |
| 6 | 23 | 78 | 100 |
| Average | 22 | 76 | 99 |

While the formulations of Example 1A and Example 1B provided extended release profiles (exemplified by in vitro dissolution), it was found that the release profiles changed after exposure to high temperatures in excess of room temperature, showing variation in the dissolution release characteristics. For example, after exposure to 60° C. conditions for one week, the dissolution release profile shifted up, releasing relatively more active at each time point compared to product that was not exposed to high temperatures.

Example 1C and Example 1D—Ethylcellulose w/ Kollicoat® Pore Former

The compositions of Example 1C and Example 1D beads and capsules are provided in Table 6.

TABLE 6

| | Formulation of Core Beads | |
|---|---|---|
| | Example 1C | Example 1D |
| Ingredients | Unit (mg) | Unit (mg) |
| CTN HCl (API) | 200 | 200 |
| Microcrystalline cellulose (Avicel® PH-101) | 160 | 160 |
| Mannitol (Pearitol 50 C) | 40 | 40 |
| Coated Beads | 19% weight gain | 25% weight gain |
| Ingredients of the coating | Unit (mg) | Unit (mg) |
| Ethylcellulose (Aquacoat® ECD 30) (as solid) | 57.58 | 74.63 |
| Triethyl citrate | 14.39 | 18.66 |
| Polyvinyl Alcohol/Polyethylene Glycol graft copolymer (Kollicoat® IR) | 4.03 | 6.72 |
| Talc | 2.39 | 2.51 |
| Capsule HPMC, Size 00 | 1 Ea | 1 Ea |

The core beads were made as described in connection with Table 1 above.

Coatings of ethylcellulose, polyvinyl alcohol/polyethylene glycol graft copolymer (pore former), and plasticizer were applied to the core beads in the amounts shown in Table 6. Application of the coating material was carried out using a fluid bed processor. The required quantity of the coating dispersion/solution was sprayed using Wurster process at a controlled set of process parameters. The coated beads were then dried to a desired moisture content and cured, then blended with the desired amount of talc as described in Table 6.

Assay by HPLC confirmed that the Example 1C capsules contained 100% of the intended amount of centanafadine hydrochloride and the Example 1D capsules contained 99.8% of the intended amount of centanafadine hydrochloride.

The dissolution release of the Example 1C and Example 1D capsules were tested according to USP <711> using Apparatus II (paddle) in 900 ml Super-Q® water (Type1/ultrapure water, resistivity 18.2 MW·cm at 25° C.) at 37° C.+/−0.5° C. at 50 rpm and the results are shown in Table 7 and Table 8, respectively.

TABLE 7

| | Dissolution % | | | | |
|---|---|---|---|---|---|
| Sample | 2 hours | 4 hours | 8 hours | 14 hours | 24 hours |
| 1 | 18 | 37 | 63 | 87 | 99 |
| 2 | 17 | 35 | 61 | 86 | 97 |
| 3 | 18 | 36 | 63 | 88 | 98 |
| 4 | 18 | 36 | 62 | 87 | 97 |
| 5 | 17 | 35 | 61 | 86 | 97 |
| 6 | 19 | 37 | 63 | 87 | 97 |
| % Average | 18 | 36 | 62 | 87 | 98 |
| % RSD | 4.2 | 2.5 | 1.6 | 0.9 | 0.9 |

TABLE 8

| | Dissolution % | | | | |
|---|---|---|---|---|---|
| Sample | 2 hours | 4 hours | 8 hours | 14 hours | 24 hours |
| 1 | 20 | 42 | 74 | 96 | 98 |
| 2 | 20 | 41 | 74 | 96 | 98 |
| 3 | 20 | 41 | 73 | 95 | 98 |
| 4 | 19 | 41 | 73 | 96 | 99 |
| 5 | 19 | 40 | 72 | 95 | 98 |
| 6 | 20 | 42 | 74 | 96 | 99 |
| % Average | 20 | 41 | 73 | 96 | 98 |
| % RSD | 2.6 | 1.8 | 1.1 | 0.5 | 0.5 |

Example 2—In Vivo Absorption of Example 1A and Example 1B Formulations

All doses were administered after a 10-hour overnight fast. Twelve healthy, adult subjects consumed a light snack within a 15-minute period at 2.5 and 7.5 hours postdose. The results of the in vivo absorption (plasma concentrations of centanafadine over time) of the Example 1A and Example 1B formulations are shown in FIG. 1, wherein a single dose of the Example 1A formulation (200 mg of CTN HCl), shown with square markers, and a single dose of the Example 1B formulation (200 mg of CTN HCl), shown with circle markers, were administered.

As shown in FIG. 1, the in vivo absorption profiles for the formulations of both Example 1A and Example 1B showed bimodal profiles.

Example 3—In Vivo Absorption of Example 1C and Example 1D Formulations

Figure 2:
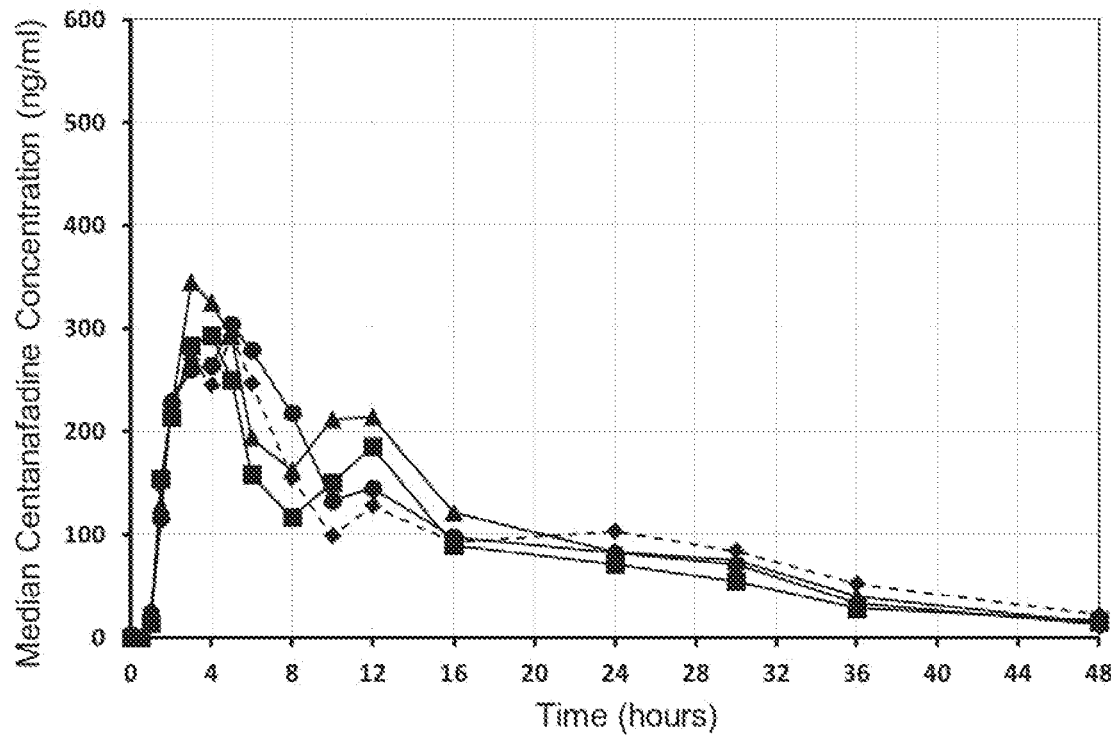
FIG. 2 is a graph of the in vivo absorption profiles of pharmaceutical formulations including centanafadine hydrochloride administered to subjects according to Example 3.

All doses were administered after a 10-hour overnight fast. 24 healthy, adult subjects were in each arm of the study. In one variation, subjects consumed a light snack within a 15-minute period at 2.5 and 7.5 hours postdose. In another variation, subjects consumed lunch ~4 hours postdose. The results of the in vivo absorption (plasma concentrations of centanafadine over time) of a single dose of the Example 1C formulation (200 mg of CTN HCl) and a single dose of the Example 1D formulation (200 mg of CTN HCl) under the various conditions are shown in FIG. 2, wherein square markers correspond to the formulation of Example 1C administered with snack, diamond markers correspond to the formulation of Example 1C administered with lunch, triangle markers correspond to the formulation of Example 1D administered with snack, and circle markers correspond to the formulation of Example 1D administered with lunch.

Figure 3:
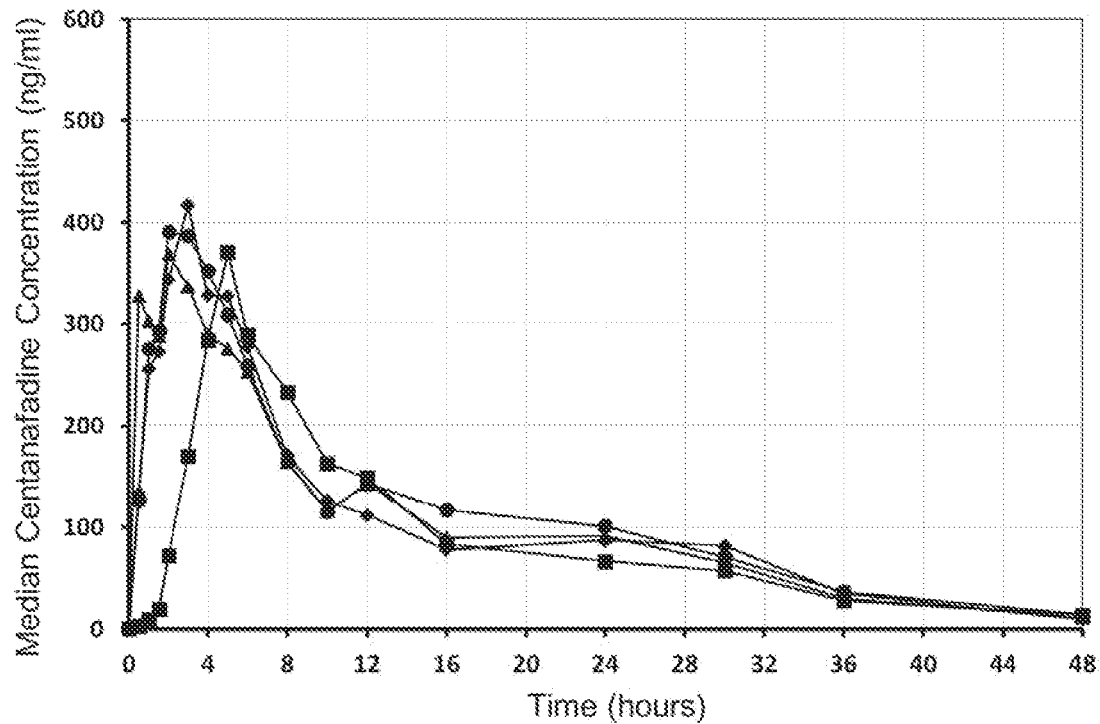
FIG. 3 and FIG. 4 are graphs of the in vivo absorption profiles of pharmaceutical formulations including centanafadine hydrochloride administered to subjects according to Example 4.

Example 4—In Vivo Absorption of Immediate Release Beads Together with Example 1D Formulation Single doses of the combination of the Example 1D formulation (200 mg of CTN HCl) with immediate release (IR) beads (extruded, spheronized beads comprising microcrystalline cellulose, mannitol, talc, and 20 mg of CTN HCl), for a total amount of 220 mg CTN HCl, were administered four different ways with respect to food. All doses were administered after a 10-hour overnight fast and subjects consumed lunch ~4 hours postdose, with no snacks offered. Twenty healthy, adult subjects were in each arm of the study. In one period, the dose was administered as intact capsules in the fasted state, without food. In another period, the dose was administered as intact capsules immediately following a high fat meal (HFM). In another period, the dose was administered as intact capsules 10 minutes prior to a light breakfast. In another period, the dose was administered as the beads sprinkled on a tablespoon of applesauce. The in vivo absorption profiles (plasma concentrations of centanafadine over time) are shown in FIG. 3, wherein: circle markers correspond to fasted; square markers correspond to HFM; diamond markers correspond to 10 minutes prior to light breakfast; and triangle markers correspond to administered as sprinkled on applesauce.

Figure 4:
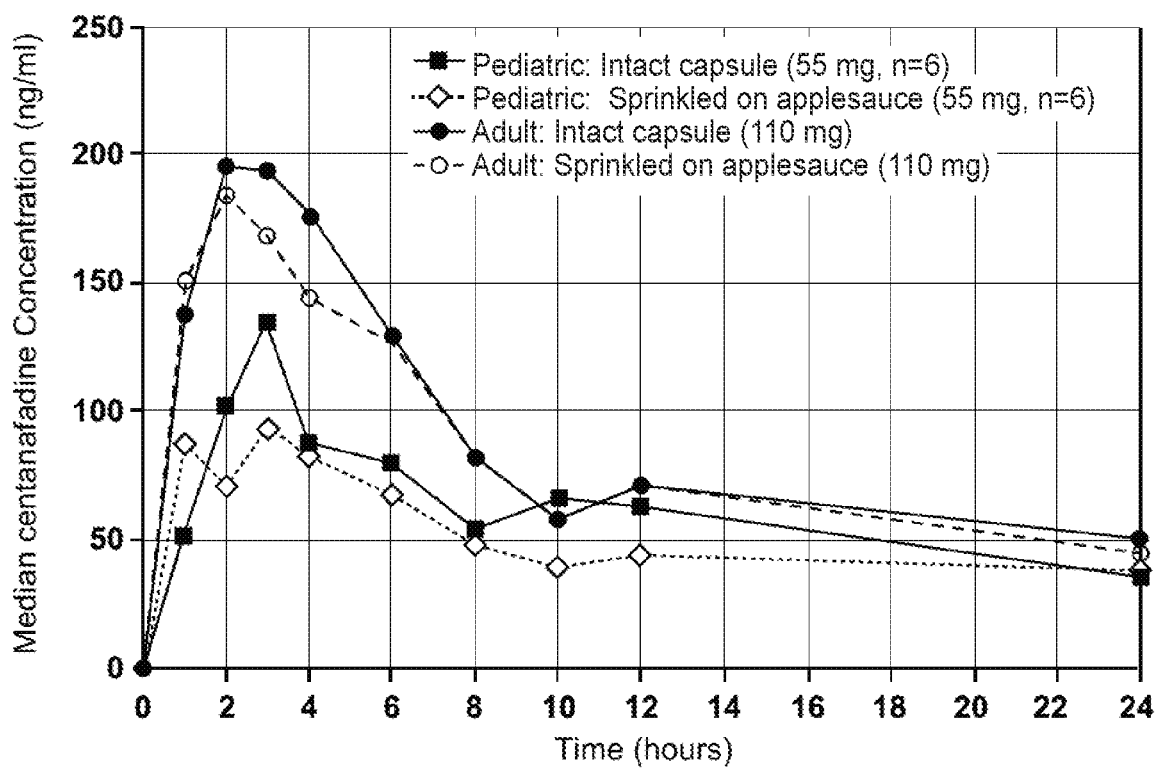

A study was also conducted in pediatric subjects, wherein single doses of the combination of the Example 1D type formulation (50 mg of CTN HCl) with immediate release (IR) beads (extruded, spheronized beads comprising microcrystalline cellulose, mannitol, talc, and 5 mg of CTN HCl), for a total amount of 55 mg CTN HCl, were administered either as intact capsules (n=6) or as beads sprinkled on applesauce (n=6) to healthy pediatric subjects. All doses were administered after a 10-hour overnight fast, and subjects consumed lunch ~4 hour postdose, no snacks offered. The in vivo absorption profiles (plasma concentrations of centanafadine over time) are shown in FIG. 4, with a comparison with simulated PK responses for a 110 mg CTN HCl dose (based on halving the data shown in FIG. 3 to simulate PK responses for single doses of 110 mg CTN HCl, as intact capsules or as beads sprinkled on applesauce to healthy adult subjects).

Example 5—In Vivo Absorption of Two and Three Bead Combinations and Dissolution Release Profiles Example 5-1 Immediate Release Beads (IR) 10% DL, 50% DL The composition of Centanafadine Immediate Release Beads (10% drug load and 50% drug load) is provided in Table 9. Centanafadine Immediate Release Beads were manufactured by weighing out and dry blending the CTN HCl, microcrystalline cellulose, and mannitol, in a high shear granulator and granulating the blended mixture with purified water, extruding and spheronization to form wet beads, fluid bed drying of the core beads, and sieving the beads to retain a desired size range.

TABLE 9

Composition of Centanafadine Immediate Release Beads 10 wt. % and 50 wt. %

| Component | Compendial Standard | Quantity (wt. % based on total weight of beads) | |
| --- | --- | --- | --- |
| | | 10% DL | 50% DL |
| Centanafadine Hydrochloride | In-house | 10.0 | 50.0 |
| Microcrystalline Cellulose (Avicel ® PH-301 available from DuPont ®) | USP/NF, EP, JP | 40.0 | — |
| Microcrystalline Cellulose (Avicel ® PH-101) | USP/NF, EP, JP | — | 40.0 |

TABLE 9-continued

Composition of Centanafadine Immediate Release Beads 10 wt. % and 50 wt. %

| Component | Compendial Standard | Quantity (wt. % based on total weight of beads) | |
| --- | --- | --- | --- |
| | | 10% DL | 50% DL |
| Mannitol (Pearlitol ® 50 C) | USP/NF, EP, JP | 50.0 | 10.0 |
| Purified Water* | USP | N/A | N/A |

*Purified water is dispensed in the manufacturing process depending on the needs of the batch size and is removed during the manufacturing process
N/A: not applicable Example 5-2—Core Beads for Sustained Release Beads (SR) and Delayed Release Beads DR The composition of Centanafadine Core Beads (80 wt. % drug load) is provided in Table 10. Centanafadine Core Beads were manufactured by weighing out and dry blending the CTN HCl and microcrystalline cellulose in a high shear granulator and granulating the blended mixture with purified water, extruding and spheronization to form wet beads, fluid bed drying of the core beads, and sieving the beads to retain a desired size range.

TABLE 10

Composition of Centanafadine Core Beads, 80 wt. %

| Component | Compendial Standard | Quantity (wt. % based on total weight of beads) |
| --- | --- | --- |
| Centanafadine Hydrochloride | In-house | 80.0 |
| Microcrystalline Cellulose (Avicel ® PH-301) | USP/NF, EP, JP | 20.0 |
| Purified Water* | USP | N/A |

*Purified water is dispensed in the manufacturing process depending on the needs of the batch size and is removed during the manufacturing process
N/A: not applicable Example 5-3—Seal Coated Beads for Sustained Release Beads (SR) and Delayed Release Beads (DR)

The composition of Centanafadine Seal Coated Beads (80 wt. % drug load) is provided in Table 11. The Centanafadine Core Beads, 80 wt. % active were made as described in Example 5-2. For seal coating, the desired quantity of the hypromellose solution in water was sprayed using a Wurster process at a controlled set of process parameters, and then the coated beads were dried to a desired moisture content.

TABLE 11

Composition of Centanafadine Seal Coated Beads, 80 wt. % active

| Component | Compendial Standard | Quantity % w/w |
| --- | --- | --- |
| Centanafadine Core Beads, 80 wt. % active | In-house | 97.1 |
| Hypromellose (Methocel ™E-5) | USP/NF, EP | 2.9 |
| Purified Water | USP | N/A |

N/A: not applicable

Example 5-4—Sustained Release Beads (SR)

The composition of Centanafadine Sustained Release Beads (10% weight gain, 15% weight gain, and 40% weight gain) is provided in Table 12. The seal coated beads from Example 5-3 were coated with a dispersion containing the ethyl acrylate and methyl methacrylate copolymer dispersion, hypromellose, talc, and polysorbate 80 using a fluid bed processor. The required quantity of the coating dispersion/solution was sprayed using Wurster process at a controlled set of process parameters. The coated beads were then dried to a desired moisture content and cured. An additional 1 wt. % of talc was dry blended with the coated beads, based on the coated beads weight.

TABLE 12

Composition of SR Coated Beads

| Component | Compendial Standard | Quantity % w/w | | |
|---|---|---|---|---|
| | | 10% WG | 15% WG | 40% WG |
| Centanafadine Seal Coated Beads, 80 wt. % active | In-house | 81.6 | 74.8 | 52.6 |
| Ethyl Acrylate and Methyl Methacrylate Copolymer Disp. (Eudragit ® NM 30 D) | NF, EP | 8.2 | 11.2 | 21.1 |
| Hypromellose (Methocel ™ E-5) | USP/NF, EP | 1.2 | 1.7 | 3.2 |
| Talc, 194 Pharma M | USP, EP, JP | 8.2 | 11.2 | 21.1 |
| Polysorbate 80 (Tween 80HP-LQ-MH) | NF, EP, JP | 0.8 | 1.1 | 2.1 |
| Purified Water* | USP | N/A | N/A | N/A |

Figure 5:
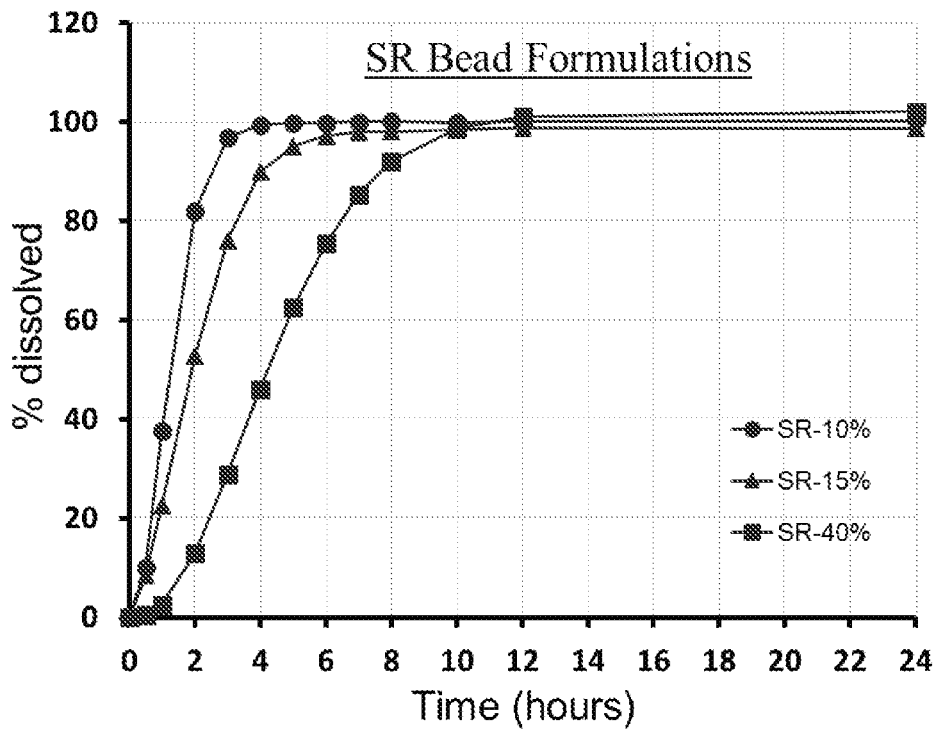
FIG. 5 is a graph of the in vitro dissolution profile.

*Purified water is dispensed in the manufacturing process depending on the needs of the batch size and is removed during the manufacturing process
N/A: not applicable Dissolution of 100 mg capsules containing the sustained release beads of Table 12 was tested according to USP <711> using Apparatus I (basket) in 1000 ml deionized water at 37° C.+/−0.5° C. at 100 rpm. Dissolution release profiles are shown in FIG. 5.

Single doses of the Table 12 SR formulations were administered in intact capsules to healthy adult subjects. The subjects were provided with a light snack and then fasted from all food and drink (except water) for a minimum of 8 h on the day prior to dosing until approximately 4 h postdose at which time lunch was provided. An evening meal was provided at approximately 10 h postdose and an evening snack at approximately 14 h postdose.

Figure 6:
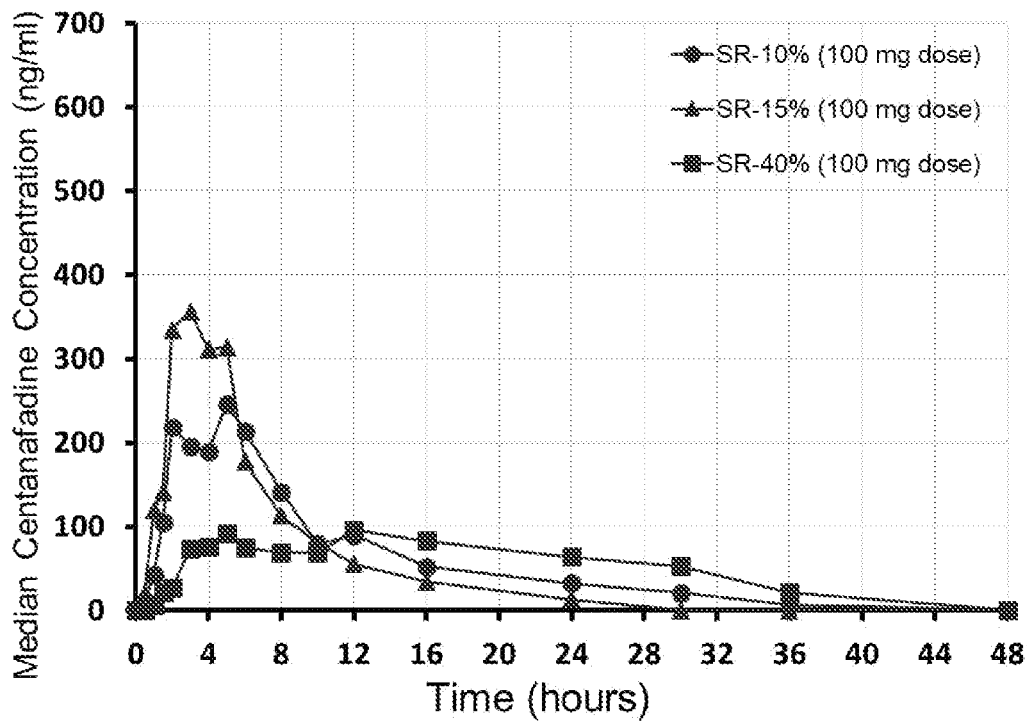
FIG. 6 is a graph of the in vivo absorption profile, of pharmaceutical formulations including centanafadine hydrochloride according to Example 5-4.

In vivo absorption profiles (plasma concentrations of centanafadine over time) for 100 mg of the sustained release beads of Table 12 with a coating amount of 10% by weight gain (n=8), 15% by weight gain (n=7) and 40% by weight gain (n=7) are shown in FIG. 6. The bioanalytical assay calculation resulting in FIG. 6 did not take into account the salt factor; as a consequence, the results in the figure overstate the plasma centanafadine concentrations by about 15%.

Example 5-5—Delayed Release Beads (DR)

The composition of Centanafadine Delayed Release Beads (10% weight gain, 15% weight gain, 20% weight gain, 30% weight gain, and 40% weight gain) is provided in Table 13. The seal coated beads from Example 5-3 were coated with a dispersion containing the poly(methyl acrylate-co-methyl methacrylate-co-methacrylic acid) and PlasACRYL® T20 using a fluid bed processor. The required quantity of the coating dispersion/solution was sprayed using Wurster process at a controlled set of process parameters. The coated beads were then dried to a desired moisture content. An additional 1 wt. % of talc and 1 wt. % of colloidal silicon dioxide were dry blended with the coated beads, based on the coated beads weight.

TABLE 13

Composition of DR Coated Beads

| Component | Compendial Standard | Quantity % w/w | | | | |
|---|---|---|---|---|---|---|
| | | 10% WG | 15% WG | 20% WG | 30% WG | 40% WG |
| Centanafadine Seal Coated Beads, 80 wt. % active | In-house | 90.1 | 85.8 | 82.0 | 75.2 | 69.4 |
| Poly(Methyl Acrylate-CO-Methyl Methacrylate-CO-Methacrylic Acid) (Eudragit ® FS 30 D, Aq. Dispersion) | In-house | 9.0 | 12.9 | 16.4 | 22.6 | 27.8 |
| PlasACRYL ® T20 (emulsion of glyceryl monostearate, triethyl citrate, polysorbate 80 and water with a solid content of about 20%) | In-house | 0.9 | 1.3 | 1.6 | 2.3 | 2.8 |
| Purified Water | USP | N/A | N/A | N/A | N/A | N/A |

N/A: not applicable

Dissolution release was tested for capsules containing 100 mg active of the formulations of Table 13 at various levels of coating (10, 15, 20, 30, and 40% weight gain) according to USP <711> using Apparatus I (basket) in 1000 mL 0.1N hydrochloric acid at 37° C.+/−0.5° C. at 100 rpm for 2 hours, followed by Apparatus I (basket) in 1000 mL pH 7.4 phosphate buffer solution at 37° C.+/−0.5° C.) at 100 rpm. Dissolution release profiles are shown in FIG. 7. FIG. 7 shows that the delayed release coating also has a sustained release function. Without intending to be bound by any particular theory, it is possible that since the poly(methyl acrylate-co-methyl methacrylate-co-methacrylic acid) polymer is anionic, having negatively charged carboxylate moieties (ratio of carboxylate groups to ester groups approx. 1:10), and centanafadine is a positively-charged secondary amine, the polymer could be influencing the rate of release of centanafadine from the beads due to ionic interaction.

Single doses of the Table 13 DR formulations were administered in intact capsules to healthy adult subjects. The subjects were provided with a light snack and then fasted from all food and drink (except water) for a minimum of 8 h on the day prior to dosing until approximately 4 h postdose at which time lunch was provided. An evening meal was provided at approximately 10 h postdose and an evening snack at approximately 14 h postdose.

Figure 8:
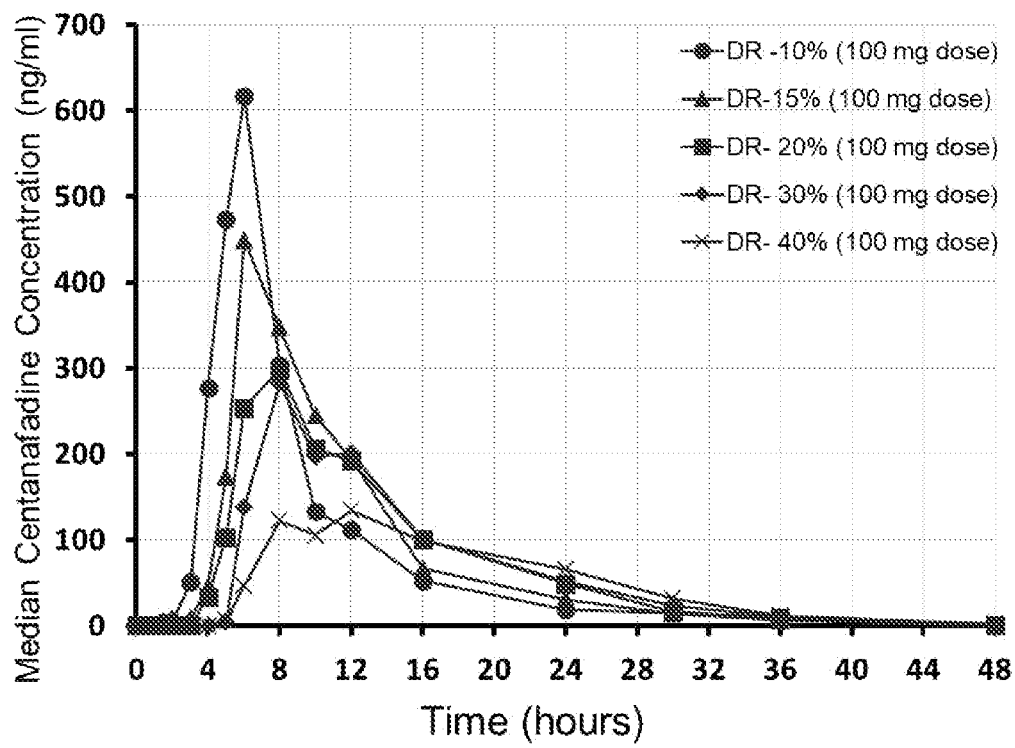
FIG. 8 is a graph of the in vivo absorption profile of pharmaceutical formulations including centanafadine hydrochloride according to Example 5-5.

In vivo absorption profiles (plasma concentrations of centanafadine over time) for 100 mg of the delayed release beads of Table 13 with a coating amount of 10% by weight gain (n=6), 15% by weight gain (n=7), 20% by weight gain (n=8), 30% by weight gain (n=8), and 40% by weight gain (n=8) are shown in FIG. 8. The bioanalytical assay calculation resulting in the figure did not take into account the salt factor; as a consequence, the results in the figure overstate the plasma centanafadine concentrations by about 15%.

Example 5-6—Combination of IR Beads, SR Beads, and DR Beads

Figure 9:
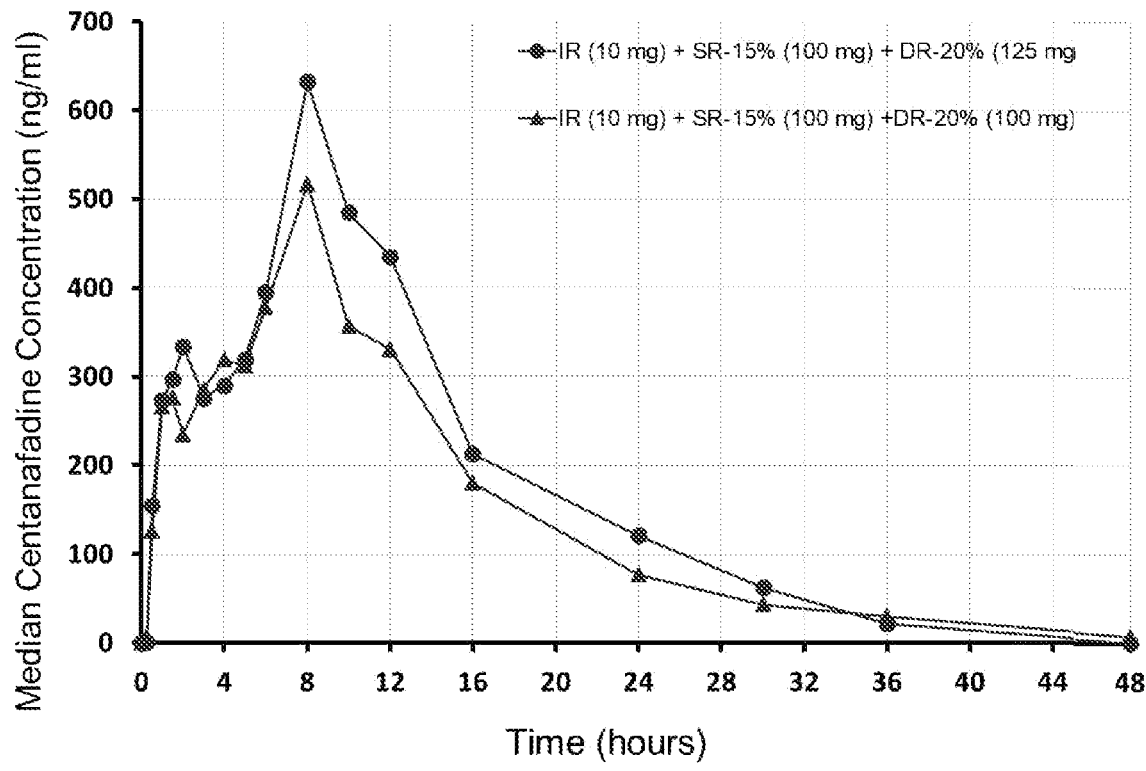
FIG. 9 and FIG. 10 are graphs of the in vivo absorption profile of pharmaceutical formulations disclosed herein including immediate release beads, sustained release beads, and delayed release beads including centanafadine hydrochloride according to Example 5-6.

In vivo absorption profiles (plasma concentrations of centanafadine over time) for two versions of capsules containing combinations of IR, SR, and DR beads are shown in FIG. 9. The first dose included 10 mg CTN HCl strength IR beads (50% active level) according to Example 5-1, 100 mg strength of SR beads according to Example 5-4 (15% weight gain coating), and 100 mg strength of DR beads according to Example 5-5 (20% weight gain coating), for a total dose of 210 mg CTN HCl. The different bead types were individually encapsulated in HPMC capsule shells. The second dose type was similar to the first dose type but with 125 mg strength of centanafadine in DR beads instead of 100 mg for a total dose of 235 mg CTN HCl. The 210 mg doses were administered in intact capsules to 17 healthy adult subjects. The 235 mg doses were administered in intact capsules to 18 healthy adult subjects. Subjects were provided with a light snack and then fasted from all food and drink (except water) for a minimum of 8 h on the day prior to dosing until approximately 4 h postdose at which time lunch was provided. An evening meal was provided at approximately 10 h postdose and an evening snack at approximately 14 h postdose. Results are as shown in FIG. 9.

Figure 10:
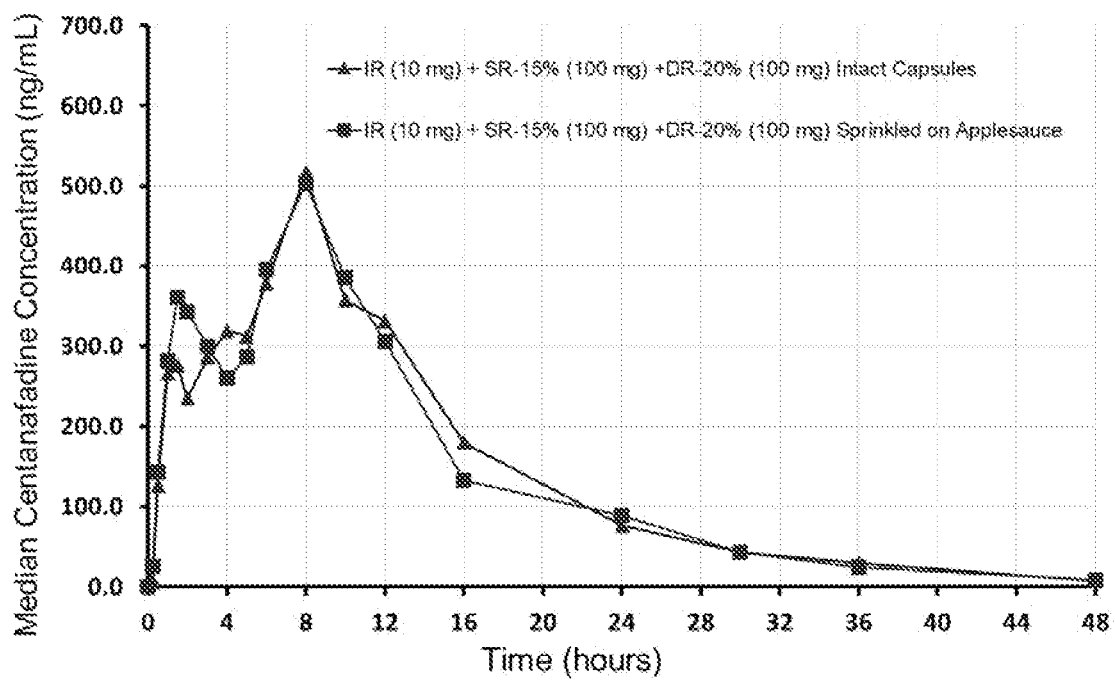

The first dose type (210 mg CTN HCl) was administered to healthy adult subjects (n=18) sprinkled on applesauce under the same conditions as described above for the intact capsules. FIG. 10 shows a comparison between the resulting in vivo absorption profiles (plasma concentrations of centanafadine over time) for the first combination capsule from FIG. 9, administered as intact capsules, and the same formulation administered sprinkled on a tablespoon of applesauce.

The bioanalytical assay calculation resulting in the figures did not take into account the salt factor; as a consequence, the results in the figures overstate the plasma centanafadine concentrations by about 15%.

Example 6

Figure 11:
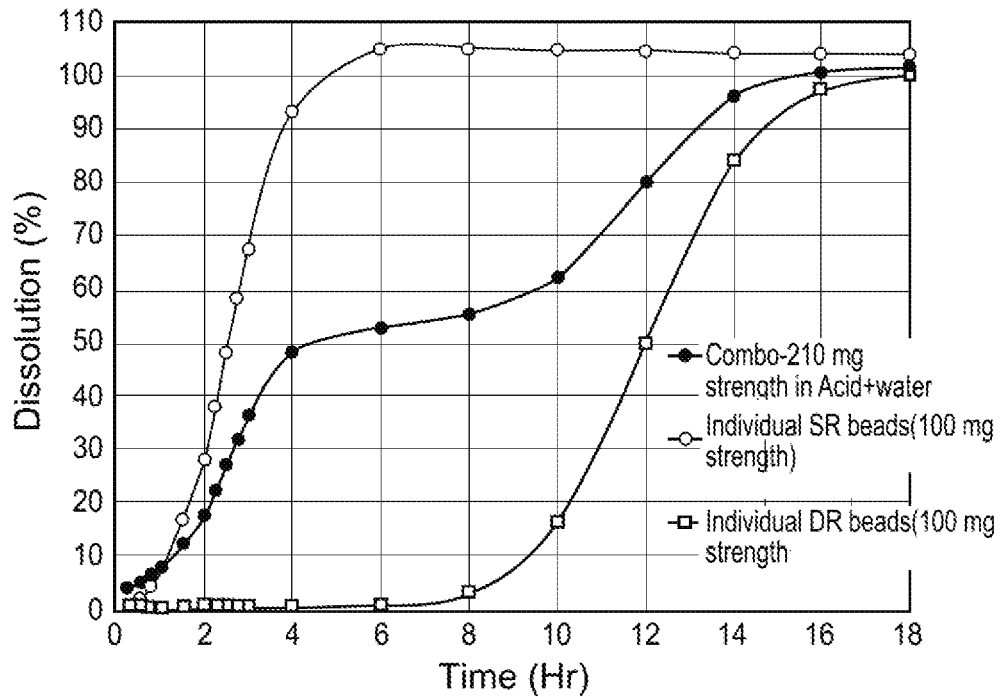
FIG. 11, FIG. 12 and FIG. 13 are graphs of dissolution release profiles of centanafadine hydrochloride pharmaceutical formulations in various media according to Example 6.

FIG. 11 shows the dissolution release profile of a formulation including a mixture of IR beads (10 mg of CTN HCl according to Example 5-1), 15% weight gain coated sustained release beads (100 mg of CTN HCl according to Example 5-4), and 20% weight gain coated delayed release beads (100 mg CTN HCl according to Example 5-5) compared to a formulation including only the 15% weight gain coated sustained release beads (100 mg of CTN HCl according to Example 5-4), and a formulation including only the 20% coating weight coated delayed release beads (100 mg CTN HCl according to Example 5-5). The formulations were tested for their dissolution release profiles in acid+water media according to USP <711> with Apparatus 1 (basket) at 37° C.+/−0.5° C. at 100 rpm, first in 1000 ml of a HCl solution for 2 hours, then 1000 ml unbuffered deionized water for the remainder of the time.

Figure 12:
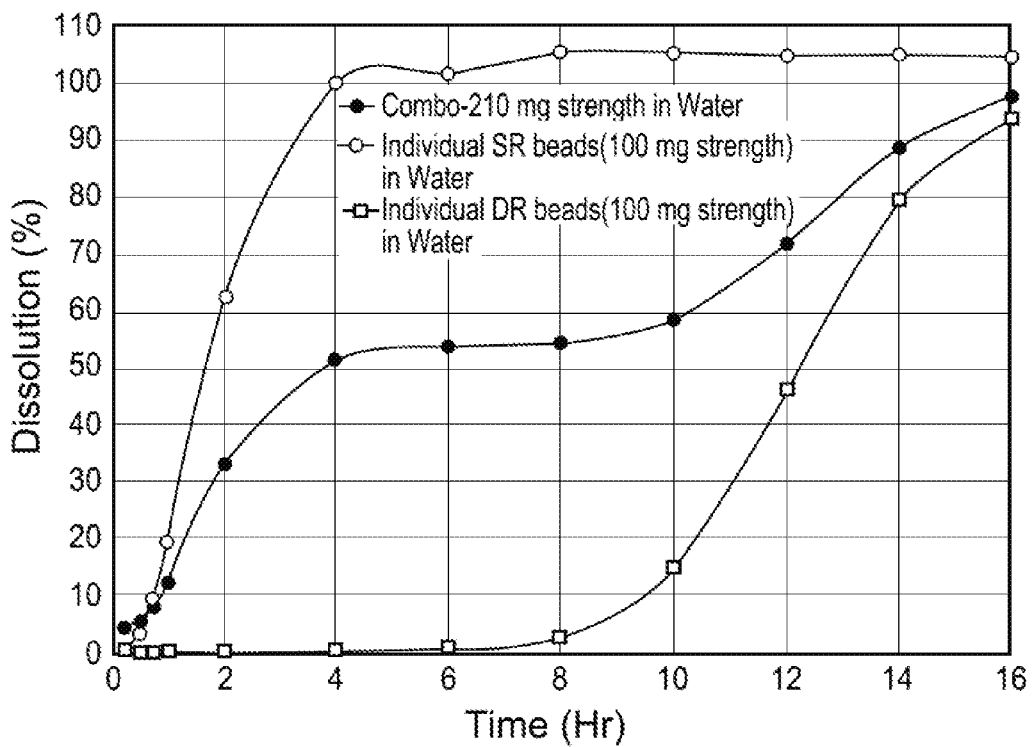

FIG. 12 shows the dissolution release profile of a capsule including a mixture of IR beads (10 mg of CTN HCl according to Example 5-1), 15% weight gain coated sustained release beads (100 mg of CTN HCl according to Example 5-4), and 20% weight gain coated delayed release beads (100 mg CTN HCl according to Example 5-5) compared to a capsule including only the 15% weight gain coated sustained release beads (100 mg of CTN HCl according to Example 5-4), and a capsule including only the 20% coating weight coated delayed release beads (100 mg CTN HCl according to Example 5-5). The capsules were tested for their dissolution release profiles in 1000 ml unbuffered deionized water medium according to USP <711> with Apparatus 1 (basket) at 37° C.+/−0.5° C. at 100 rpm.

Figure 13:
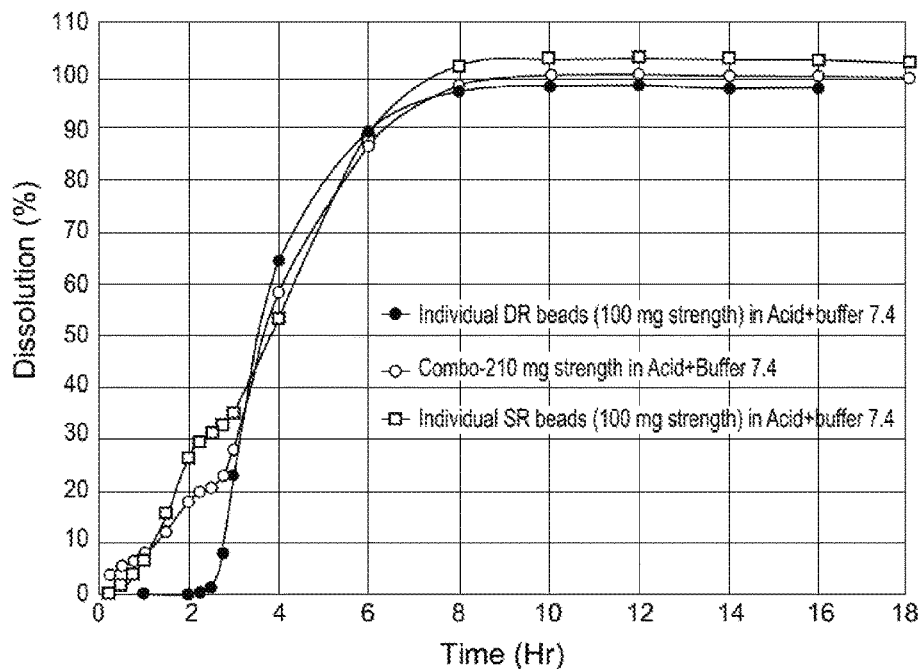

FIG. 13 shows the dissolution release profile of a capsule including a mixture of IR beads (10 mg of CTN HCl according to Example 5-1), 15% weight gain coated sustained release beads (100 mg of CTN HCl according to Example 5-4), and 20% weight gain coated delayed release beads (100 mg CTN HCl according to Example 5-5) compared to a capsule including only the 15% weight gain coated sustained release beads (100 mg of CTN HCl according to Example 5-4), and a capsule including only the 20% coating weight coated delayed release beads (100 mg CTN HCl according to Example 5-5). The formulations were tested for their dissolution release profiles in acid+buffered (pH 7.4) media according to USP <711> with Apparatus 1 (basket) at 37° C.+/−0.5° C. at 100 rpm, first in 1000 ml of HCl solution for 2 hours, then in pH 7.4 phosphate buffer for the remainder of the time.

The dissolution release profiles for the formulation including a mixture of IR beads (10 mg of CTN HCl), 10% drug loaded sustained release beads (100 mg of CTN HCl), and 20% drug loaded delayed release beads (100 mg CTN HCl) showed a desirable multiphasic release profile that was a combination of all three formulation types, when tested in acid media followed by pH 7.4 buffered medium, simulating gastric conditions. The immediate release beads were approximately 5% of the formulation in the combination capsules, but the formulation released about 18-20% of active in the first 2 hours in acid medium, confirming that the sustained release coating contributes to release of active in acidic media.

Example 7

Figure 14:
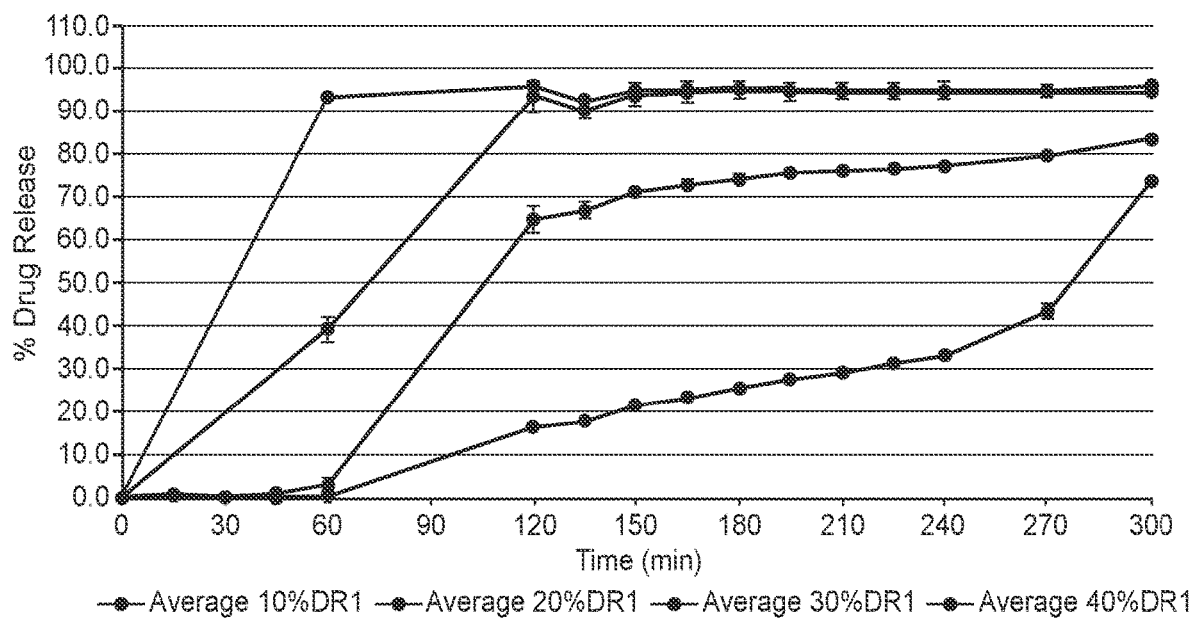
FIG. 14 is a graph of the dissolution release profile of centanafadine hydrochloride formulations disclosed herein, coated with a copolymer derived from methacrylic acid and ethyl acrylate (1:1).

Centanafadine HCl bead cores (80% DL) according to Table 10 were coated with a copolymer derived from methacrylic acid and ethyl acrylate (1:1) available from Evonik under the trade name Eudragit® L 30 D-55, plasticized with a small amount of PlasACRYL® HTP20 (a mixture of glyceryl monostearate glidant and triethyl citrate plasticizer). Dissolution release profiles according to USP <711> with Apparatus 2 (paddle) at 50 rpm, first in 750 ml of a 0.1N HCl solution for 2 hours, then in 974 ml of pH 6.5 phosphate buffered water for the remainder of the time, are shown in FIG. 14. The polymer coating was applied to the beads at coating amounts of 10%, 20%, 30%, and 40% by weight gain, wherein the left trace corresponds to the bead with 10% weight gain, the left-middle trace corresponds to the bead with 20% weight gain, the right-middle trace corresponds to the bead with 30% weight gain, and the right trace corresponds to the bead with 40% weight gain. The polymer showed no protection in the acid stage, even up to 40% weight gain coating, as drug released within 120 minutes. Without intending to be bound by any particular theory, it is believed that the highly soluble and permeable nature of CTN HCl contributed to the results.

Example 8

Figure 15:
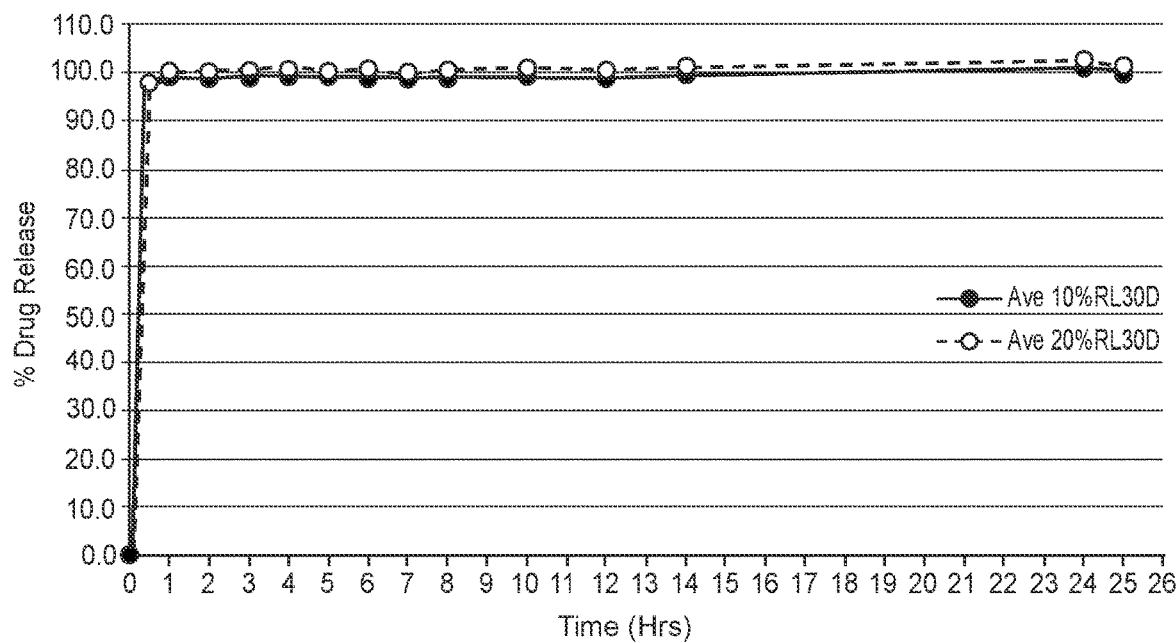
FIG. 15 and FIG. 16 are graphs of the dissolution release profiles of centanafadine hydrochloride formulations disclosed herein coated with various ammonio methacrylate copolymer dispersions.
Figure 16:
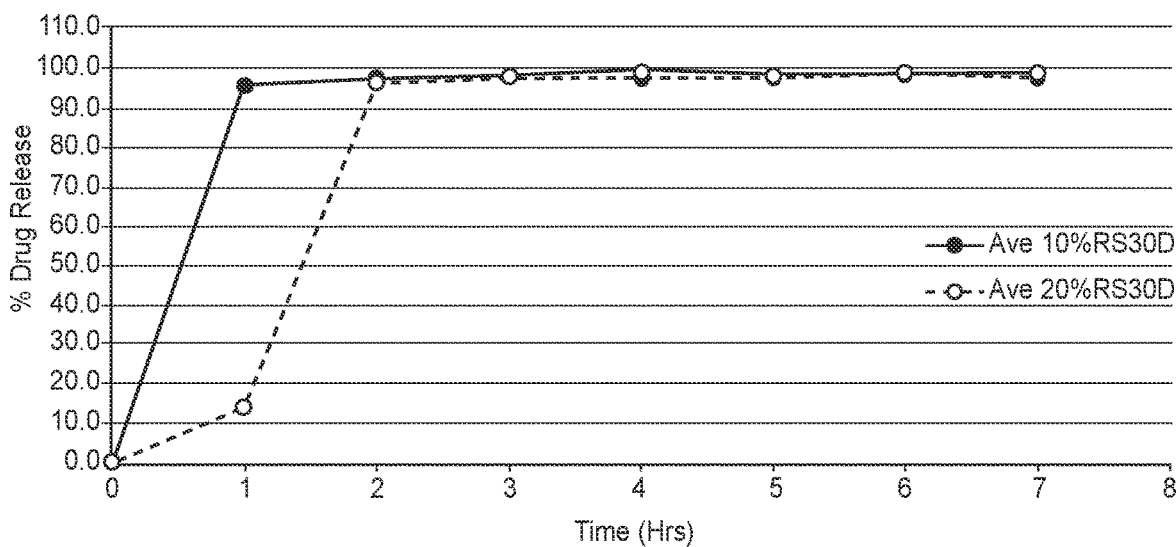

Centanafadine HCl bead cores (80% DL) according to Table 10 were coated with various ammonio methacrylate copolymer dispersions (Eudragit® RL 30 D and Eudragit® RS 30 D) at various levels of coating (10% and 20% weight gain), each of which was plasticized with a small amount of a mixture containing talc and triethyl citrate. Dissolution release profiles are shown in FIG. 15 (RL 30D) and FIG. 16 (RS 30 D), wherein the left trace corresponds to the bead with 10% weight gain and the right trace corresponds to the bead with 20% weight gain. Dissolution was tested in 1000 mL deionized water at 50 RPM according to USP <711> at 50 RPM with Apparatus 2 (paddle). The polymers did not provide sustained release, but could be used as seal coating polymers. Without intending to be bound by any particular theory, it is believed that the highly soluble and permeable nature of CTN HCl contributed to the results.

Example 9

The composition of various centanafadine sustained release capsules is provided in Table 14.

TABLE 14

| Component | 52.5 mg Sustained Release Capsules Quantity/Capsule(mg) | 78.8 mg Sustained Release Capsules Quantity/Capsule(mg) | 210 mg Sustained Release Capsules Quantity/Capsule(mg) | 241.5 mg Sustained Release Capsules Quantity/Capsule(mg) |
|---|---|---|---|---|
| Centanafadine hydrochloride | 52.5 | 78.8 | 210 | 241.5 |
| Mannitol (PEARLITOL ® 50 C) | 12.5 | 19 | 2 | 2.3 |
| Microcrystalline Cellulose (Avicel ®PH-301) | 22.6 | 33.9 | 50 | 57.5 |
| Microcrystalline Cellulose (Avicel ® PH-101) | — | — | 8 | 9.2 |
| Hypromellose (Methocel ™ E-5) | 2.6 | 3.9 | 10.5 | 12 |
| Ethyl Acrylate and Methyl Methacrylate Copolymer Disp. (Eudragit ® NM 30 D) | 4.8 | 7.2 | 19.3 | 22.2 |
| Polysorbate 80 (Tween 80HP-LQ-MH) | 0.5 | 0.7 | 1.9 | 2.2 |
| Eudragit ® FS 30 D, Aq. Dispersion, [Poly(Methyl Acrylate-CO-Methyl Methacrylate-CO-Methacrylic Acid)] | 6.4 | 9.7 | 25.8 | 29.6 |
| PlasACRYL ® T20 | 0.6 | 1 | 2.6 | 3 |
| Talc, 194 Pharma M | 5.6 | 8.5 | 22.6 | 26 |
| Colloidal Silicon Dioxide (Aerosil 200 Pharma) | 0.4 | 0.6 | 1.6 | 1.8 |
| Vacant HPMC Capsule shell | 1 unit (size3) | 1 unit (size2) | 1 unit (size0) | 1 unit (size0) |
| Total | 108.5 | 163.3 | 354.3 | 407.3 |

Example 10

Additional centanafadine capsules were made with different mixtures IR beads according to Table 1 above, 15% weight gain coated sustained release beads according to Table 15 below, and 20% weight gain coated delayed release beads according to Table 16. The overall composition of various centanafadine capsule strengths is provided in Table 17, and the compositions of the capsules by bead type are provided in Table 18.

TABLE 15

Composition of SR Coated Beads, 15% weight gain coating

| Component | Compendial Standard | Quantity % w/w |
|---|---|---|
| Centanafadine Seal Coated Beads, 80 wt. % active (according to Table 11 above) | In-house | 74.0 |
| Ethyl Acrylate and Methyl Methacrylate Copolymer Disp. (Eudragit ® NM 30 D) | NF, EP | 11.1 (net dry solid) |
| Hypromellose (Methocel ™ E-5) | USP/NF, EP | 1.7 |
| Talc, 194 Pharma M | USP, EP, JP | 12.1 |
| Polysorbate 80 (Tween 80HP-LQ-MH) | NF, EP, JP | 1.1 |
| Purified Water* | USP | N/A |

*Purified water is dispensed in the manufacturing process and is removed during the manufacturing process
N/A: not applicable

TABLE 16

Composition of DR Coated Beads, 20% weight gain coating

| Component | Compendial Standard | Quantity % w/w |
|---|---|---|
| Centanafadine Seal Coated Beads, 80 wt. % active (according to Table 11 above) | In-house | 80.3 |

TABLE 16-continued

Composition of DR Coated Beads, 20% weight gain coating

| Component | Compendial Standard | Quantity % w/w |
|---|---|---|
| Poly(Methyl Acrylate-CO-Methyl Methacrylate-CO-Methacrylic Acid) (Eudragit ® FS 30 D, Aq. Dispersion) | In-house | 16.1 (net dry solid) |
| PlasACRYL ® T20 (emulsion of glyceryl monostearate, triethyl citrate, polysorbate 80 and water with a solid content of about 20%) | In-house | 1.6 (net dry solid) |
| Talc, 194 Pharma M | USP, EP, JP | 1.0 |
| Colloidal Silicon Dioxide (Aerosil ® 200 Pharma) | USP/NF, EP, JP | 1.0 |
| Purified Water* | USP | N/A |

*Purified water is dispensed in the manufacturing process and is removed during the manufacturing process
N/A: not applicable

TABLE 17

| Component | 41.1 mg Capsules Quantity/Capsule(mg) | 82.2 mg Capsules Quantity/Capsule(mg) | 123.3 mg Capsules Quantity/Capsule(mg) |
|---|---|---|---|
| Centanafadine hydrochloride | 41.1 | 82.2 | 123.3 |
| Mannitol (PEARLITOL ® 50 C) | 24.9 | 2 | 3 |
| Microcrystalline Cellulose (Avicel ®PH-301) | 28.9 | 18 | 27 |
| Microcrystalline Cellulose (Avicel ® PH-101) | 0 | 8 | 11.9 |
| Hypromellose (Methocel ™ E-5) | 1.9 | 3.8 | 5.6 |
| Ethyl Acrylate and Methyl Methacrylate Copolymer Disp. (Eudragit ® NM 30 D)* | 3.5 | 7 | 10.5 |
| Polysorbate 80 (Tween 80HP-LQ-MH) | 0.3 | 0.7 | 1 |
| Eudragit ® FS 30 D, Aq. Dispersion, [Poly(Methyl Acrylate-CO-Methyl Methacrylate-CO-Methacrylic Acid)]* | 4.7 | 9.3 | 14 |
| PlasACRYL ® T20* | 0.5 | 0.9 | 1.4 |
| Talc, 194 Pharma M | 4.3 | 8.3 | 12.4 |
| Colloidal Silicon Dioxide (Aerosil ® 200 Pharma) | 0.3 | 0.6 | 0.9 |
| Vacant HPMC Capsule shell | 1 unit (size 4) | 1 unit (size 3) | 1 unit (size 1) |
| Total | 110 | 141 | 211 |

| Component | 164.4 mg Capsules Quantity/Capsule(mg) | 246.6 mg Capsules Quantity/Capsule(mg) | 328.8 mg Capsules Quantity/Capsule(mg) |
|---|---|---|---|
| Centanafadine hydrochloride | 164.4 | 246.6 | 328.8 |
| Mannitol (PEARLITOL ® 50 C) | 4 | 6 | 8 |
| Microcrystalline Cellulose (Avicel ®PH-301) | 36.2 | 54.2 | 72.2 |
| Microcrystalline Cellulose (Avicel ® PH-101) | 15.9 | 23.9 | 31.8 |
| Hypromellose (Methocel ™ E-5) | 7.5 | 11.3 | 15 |
| Ethyl Acrylate and Methyl Methacrylate Copolymer Disp. (Eudragit ® NM 30 D)* | 13.9 | 20.9 | 27.9 |
| Polysorbate 80 (Tween 80HP-LQ-MH) | 1.4 | 2.1 | 2.8 |
| Eudragit ® FS 30 D, Aq. Dispersion, [Poly(Methyl Acrylate-CO-Methyl Methacrylate-CO-Methacrylic Acid)]* | 18.6 | 27.9 | 37.2 |
| PlasACRYL ® T20* | 1.9 | 2.8 | 3.7 |
| Talc, 194 Pharma M | 16.2 | 24.8 | 33.1 |
| Colloidal Silicon Dioxide (Aerosil ® 200 Pharma) | 1.1 | 1.7 | 2.3 |
| Vacant HPMC Capsule shell | 1 unit (size 1) | 1 unit (size 0EL) | 1 unit (size 00) |
| Total | 282 | 422 | 563 |

*net solid content

TABLE 18

| | All weights below in Salt Form | | | | | | |
|---|---|---|---|---|---|---|---|
| | IR Beads | | SR Beads (15% WG) | | DR Beads (20% WG) | | Total |
| Total Strength (Salt) | Strength | Fill weight | Strength | Fill weight | Strength | Fill weight | Fill Weight |
| 41.1 mg | 5 mg | 50 mg (10% DL) | 18.05 mg | 31 mg | 18.05 mg | 29 mg | 110 mg |
| 82.2 mg | 10 mg | 20 mg (50% DL) | 36.1 mg | 63 mg | 36.1 mg | 58.0 mg | 141 mg |
| 123.3 mg | 15 mg | 30 mg (50% DL) | 54.15 mg | 94 mg | 54.15 mg | 87 mg | 211 mg |
| 164.4 mg | 20 mg | 40 mg (50% DL) | 72.2 mg | 126 mg | 72.2 mg | 116 mg | 282 mg |
| 246.6 mg | 30 mg | 60 mg (50% DL) | 108.3 mg | 188 mg | 108.3 mg | 174 mg | 422 mg |
| 328.8 mg | 40 mg | 80 mg (50% DL) | 144.4 mg | 251 mg | 144.4 mg | 232 mg | 563 mg |

Example 11

Figure 17:
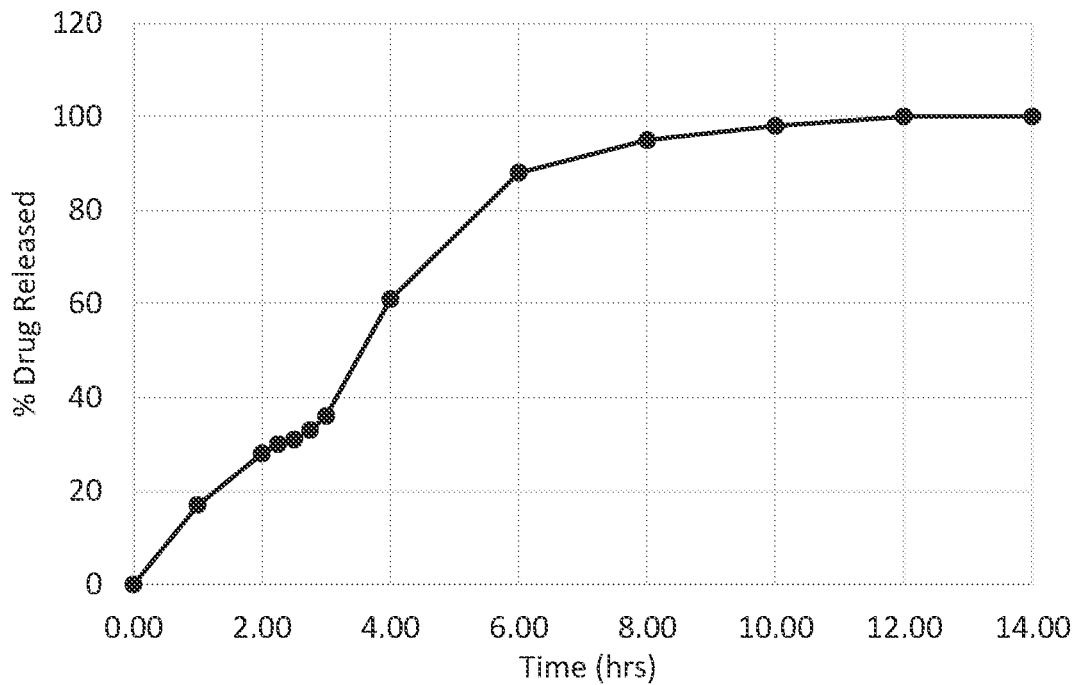
FIG. 17 is a graph of the dissolution release profile of a centanafadine hydrochloride formulation of Example 10, as described in Example 11.

The dissolution release characteristics of the 164.4 mg dosage form of Example 10 were measured by testing in acid followed by pH 7.4 medium. Specifically, the release profile was determined according to USP <711> using Apparatus I (basket) in 1000 mL 0.1N hydrochloric acid at 37° C.+/−0.5° C. at 100 rpm for 2 hours, followed by Apparatus I (basket) in 1000 mL pH 7.4 phosphate buffer solution at 37° C.+/− 0.5° C.) at 100 rpm for 12 hours. The percentage of drug released was measured at various time points. The results are presented in FIG. 17.

Example 12

Figure 18:
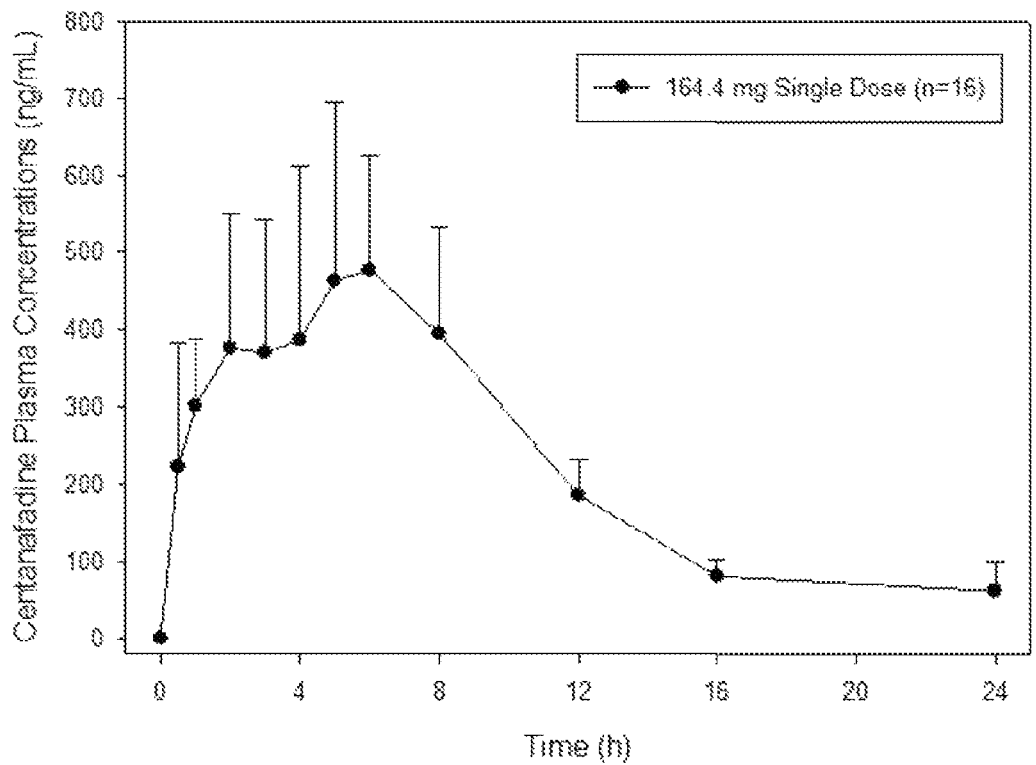
FIG. 18 shows mean centanafadine plasma concentrations resulting from dosing the formulation of Table 17 in a first pharmacokinetics (PK) study as described in Example 12.

Plasma pharmacokinetics were evaluated the for the CTN HCl formulation of Table 17 above. A single oral dose of a 164.4 mg strength capsule of Table 17 was administered to fasted healthy adult subjects (n=16) and plasma concentrations of centanafadine were measured over time. The results shown in FIG. 18 are of mean plasma concentrations at the measured time points. The results shown in Table 19 below for Cmax and AUC are population means, and for population t max are the population median, across all time points.

TABLE 19

| Parameter[a] | Centanafadine HCl 164.4 mg |
|---|---|
| $C_{max}$ (ng/ml) | 618 (215) |
| $C_{1hr}$ (ng/ml) | 302 (85.7) |
| $C_{12hr}$ (ng/ml) | 186 (46.5) |
| $C_{16hr}$ (ng/ml) | 80.9 (21.7) |
| $t_{max}$ (h) | 4.50 (2.00-8.00) |
| $AUC_{0-1\ h}$ (ng · h/mL) | 215 (104) |
| $AUC_{0-24\ h}$ (ng · h/mL) | 5290 (1140) |
| $AUC_{0-t}$ (ng · h/mL) | 5820 (1280) |
| $AUC_{0-inf}$ (ng · h/mL) (n = 11) | 6240 (1380) |

[a]Values are mean (SD) except for $t_{max}$ which is median (minimum-maximum).

Figure 19:
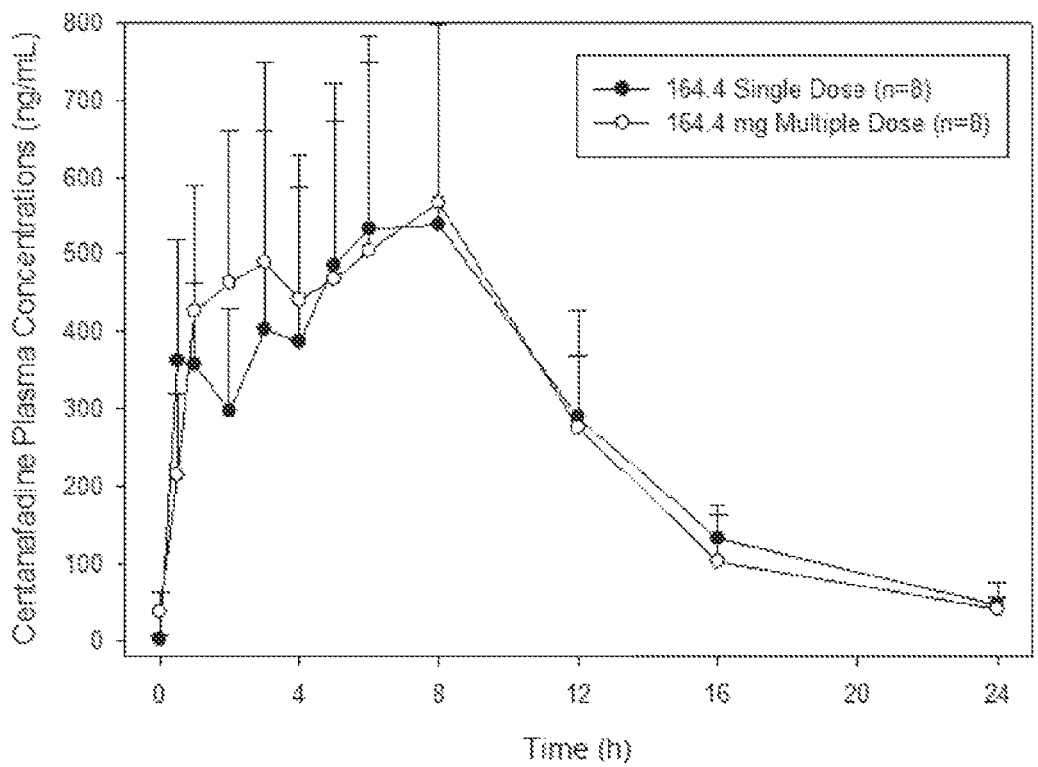
FIG. 19 shows mean centanafadine plasma concentrations resulting from dosing the formulation of Table 17 in a second PK study as described in Example 12.

In another PK study, capsule formulations according to Table 17 above (as 164.4 capsules, one administered for 164.4 mg dose strength, and two administered for 328.8 mg dose strength), were administered to groups of eight healthy adult subjects for 5 days, and serum concentrations were measured on the first and fifth days after dosing in the fasted state. The results shown in FIG. 19 are of mean centanafadine plasma concentrations at the measured time points, for the 164.4 mg strength dose. The results shown in Table 20 below for Cmax and AUC are population means, and for population t max are the population medians, across all time points.

TABLE 20

| | Centanafadine HCl 164.4 mg (n = 8) | | Centanafadine HCl 328.8 mg (n = 6) | |
|---|---|---|---|---|
| Parameter[a] | First Day | Fifth Day | First Day | Fifth Day |
| $C_{max}$ (ng/ml) | 651 (252) | 709 (300) | 1940 (781) | 2230 (577) |
| $C_{1\ hr}$ (ng/ml) | 358 (104) | 427 (161) | 640 (369) | 718 (240) |
| $C_{12\ hr}$ (ng/ml) | 289 (79.5) | 276 (153) | 750 (325) | 646 (241) |
| $C_{16\ hr}$ (ng/ml) | 133 (43.2) | 103 (61.5) | 306 (182) | 211 (64.2) |
| $t_{max}$ (h) | 7.00 (0.5-12.00) | 5.50 (1.00-8.00) | 4.00 (1.00-8.00) | 5.00 (3.00-8.00) |
| $AUC_{0-24\ h}$ (ng · h/mL) | 6570 (1960) | 6650 (2780) | 16000 (4710) | 18400 (4310) |
| $AUC_{0-inf}$ (ng · h/mL) | 7110 (2000) | | 16700 (4650) | |
| $C_{max}$ ratio[b] | — | 1.13 (0.352) | — | 1.25 (0.334) |
| AUC ratio[b] | — | 0.98 (0.170) | — | 1.19 (0.223) |

[a]Values are mean (SD) except for $t_{max}$ which shows median (minimum-maximum).
[b]Parameter ratios, Fifth Day/First Day Table 21 below shows a grouped analysis of PK parameters from the foregoing two single oral dose studies using 164.4 mg doses (n=24).

TABLE 21

| Parameter[a] | Centanafadine HCl 164.4 mg |
|---|---|
| $C_{max}$ (ng/ml) | 629 (223) |
| $C_{1\ hr}$ (ng/ml) | 321 (93.8) |
| $C_{12\ hr}$ (ng/ml) | 220 (76.0) |
| $C_{16\ hr}$ (ng/ml) | 98.4 (38.9) |
| $t_{max}$ (h) | 5.00 (0.50-12.00) |
| $AUC_{0-1\ h}$ (ng · h/mL) | 395 (36.3) |
| $AUC_{0-24\ h}$ (ng · h/mL) | 5716 (1549) |
| $AUC_{0-8\ h}$ (ng · h/mL) | 3150 (994) |
| $AUC_{2-8\ h}$ (ng · h/mL) | 2599 (883) |

[a]Values are mean (SD) except for $t_{max}$ which is median (minimum-maximum).

Example 13

[i] Core beads were made as described in connection with Table 10 above.

[ii] Seal coated beads were made as described in connection with Table 11 above.

[iii] The compositions of Centanafadine HCl Sustained Release beads (7.5% weight gain, 10% weight gain, and, 20% weight gain) are provided in Table 22. The seal coated beads from Example 5-3 were coated with a dispersion containing the ethylcellulose aqueous dispersion, methyl cellulose and triethyl citrate using a fluid bed processor. The required quantity of the coating dispersion was sprayed using Wurster process at a controlled set of process parameters, and cured.

TABLE 22

| | Quantity % w/w | | |
|---|---|---|---|
| Component | 7.5% WG | 10% WG | 20% WG |
| Centanafadine HCl seal coated beads | 90.5 | 87.7 | 78.1 |
| Ethylcellulose (Aquacoat ® ECD-30) | 6.8 | 8.8 | 15.6 |

TABLE 22-continued

| | Quantity % w/w | | |
|---|---|---|---|
| Component | 7.5% WG | 10% WG | 20% WG |
| Triethyl Citrate | 1.7 | 2.2 | 3.9 |
| Methylcellulose (Metolose ® SM-4 available from Shin-Etsu Chemical Co., Ltd. Tokyo, Japan) | 1.0 | 1.3 | 2.3 |

Figure 20:
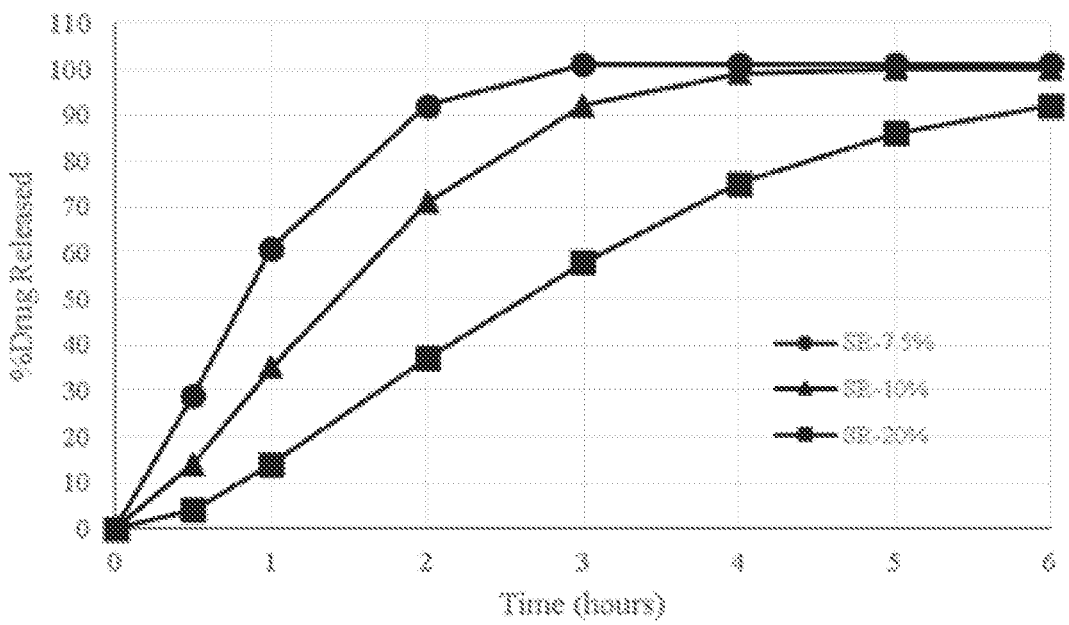
FIG. 20 shows dissolution release profiles for coated beads according to Example 13.

[iv] Dissolution of the beads containing 100 mg of centanafadine HCl of Table 22 was tested according to USP<711> using Apparatus I (basket) in 900 mL deionized water at 37° C.+/−0.5° C. at 100 rpm, detected with UV absorption at 276 nm. Dissolution release profiles are shown in FIG. 20. FIG. 20 shows that these formulations exhibit sustained release characteristics and are suitable for use in a sustained release dosage form.

Example 14

[i] 50% DL core beads were made as described in connection with Table 9 above.

[ii] The compositions of Centanafadine HCl Sustained Release beads (7.5% weight gain, 12.5% weight gain, and, 17.5% weight gain) are provided in Table 23. The 50% DL core beads from Example 5-1 were coated with a dispersion containing the ethyl acrylate and methyl methacrylate copolymer, methyl cellulose and talc using a fluid bed processor. The required quantity of the coating dispersion was sprayed using Wurster process at a controlled set of process parameters, and then cured.

TABLE 23

| | Quantity % w/w | | |
|---|---|---|---|
| Component | 7.5% WG | 12.5% WG | 17.5% WG |
| Centanafadine HCl core beads | 87.0 | 80.0 | 74.1 |
| Ethyl acrylate and methyl methacrylate copolymer (Eudragit ® NE 30D) | 6.5 | 10.0 | 13.0 |
| Methylcellulose (Metolose ® SM-4) | 0.3 | 0.5 | 0.6 |
| Talc (Luzenac pharma M) | 6.2 | 9.5 | 12.3 |

Figure 21:
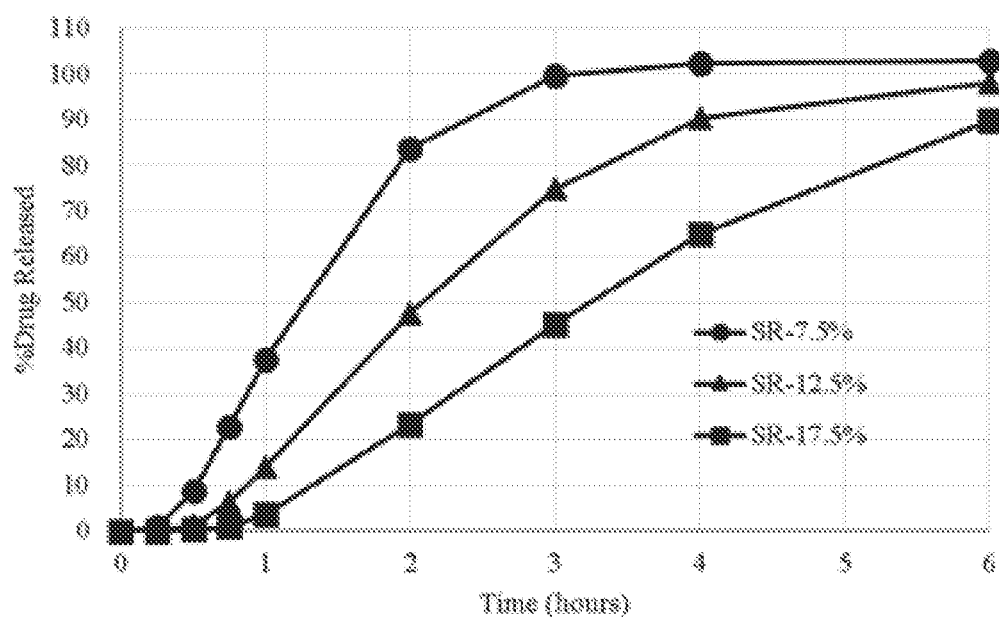
FIG. 21 shows dissolution release profiles for coated beads according to Example 14.

[iii] Dissolution of the beads containing 100 mg of centanafadine HCl of Table 23 was tested according to USP<711> using Apparatus I (basket) in 900 mL deionized water at 37° C.+/−0.5° C. at 100 rpm, detected with UV absorption at 276 nm. Dissolution release profiles are shown in FIG. 21. FIG. 21 shows that these formulations exhibit sustained release characteristics and are suitable for a sustained release dosage form.

In the foregoing description "DL" indicates drug loading concentration in the immediate release beads, as further described hereinabove; and "WG" refers to the weight gain of release coating, as further described hereinabove.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A pharmaceutical formulation dosage form comprising a plurality of centanafadine beads,
   wherein the plurality of centanafadine beads comprise centanafadine or a pharmaceutically acceptable salt thereof and an excipient;
   wherein the plurality of centanafadine beads comprises a mixture of a collection of one or more immediate release beads and a collection of one or more sustained release beads,
   wherein the centanafadine or a pharmaceutically acceptable salt thereof is present in a greater amount, by weight of the centanafadine or pharmaceutically acceptable salt thereof, in the collection of one or more sustained release beads than in the collection of one or more immediate release beads, and up to a ratio of 1:100 parts by weight of centanafadine or salt thereof, in the collection of one or more immediate release beads to the collection of one or more sustained release beads; and
   wherein the dosage form consists of centanafadine or a pharmaceutically acceptable salt thereof as a pharmaceutical active agent.

2. The pharmaceutical dosage form according to claim 1, wherein the centanafadine or a pharmaceutically acceptable salt thereof is present up to a ratio of about 1:50 parts by weight of centanafadine or salt thereof, in the collection of one or more immediate release beads to the collection of one or more sustained release beads.

3. The pharmaceutical dosage form according to claim 1, wherein the centanafadine or a pharmaceutically acceptable salt thereof is present up to a ratio of about 1:20 parts by weight of centanafadine or salt thereof, in the collection of one or more immediate release beads to the collection of one or more sustained release beads.

4. The pharmaceutical dosage form of claim 1, wherein the pharmaceutically acceptable salt is a hydrochloride salt.

5. The pharmaceutical dosage form of claim 1, wherein the one or more sustained release beads comprise a sustained release coating comprising one or more materials selected from an alkylcellulose, acrylic acid polymer, a methacrylic acid polymer, an acrylic acid copolymer, a methacrylic acid copolymer, and a cellulose ether.

6. The pharmaceutical dosage form of claim 5, wherein the sustained release coating comprises an ethyl acrylate and methyl methacrylate copolymer.

7. The pharmaceutical dosage form of claim 5, wherein the sustained release coating comprises an ethyl acrylate, a methyl methacrylate copolymer and a cellulose ether.

8. The pharmaceutical dosage form of claim 5, wherein the sustained release coating further comprises a pore former.

9. The pharmaceutical dosage form of claim 8, wherein the pore former of the sustained release coating comprises one or more materials selected from hydroxypropylcellulose, hydroxypropyl methylcellulose, polyethylene glycol, poloxamer 188, polyvinylpyrrolidone, d-mannitol, methyl cellulose, polyvinyl alcohol-polyethylene glycol graft copolymer, and saccharide.

10. The pharmaceutical dosage form of claim 1, wherein the excipient comprises one or more materials selected from a filler, a binder, a glidant, a surfactant, a polymer coating, a lubricant, a disintegrant, and a plasticizer.

11. The pharmaceutical dosage form of claim 1, wherein the plurality of centanafadine beads further comprises one or more delayed release centanafadine beads.

12. A pharmaceutical dosage form comprising a plurality of centanafadine beads,
wherein the plurality of centanafadine beads comprises centanafadine or a pharmaceutically acceptable salt thereof and an excipient;
wherein the plurality of centanafadine beads comprises a mixture of a collection of one or more immediate release beads and a collection of one or more delayed release beads,
wherein the centanafadine or a pharmaceutically acceptable salt thereof is present in a greater amount, by weight of the centanafadine or pharmaceutically acceptable salt thereof, in the collection of one or more delayed release beads than in the collection of immediate release beads, and up to a ratio of about 1:100 parts by weight of centanafadine or salt thereof, in the collection of one or more immediate release beads to the collection of one or more delayed release beads; and
wherein the dosage form consists of centanafadine or a pharmaceutically acceptable salt thereof as a pharmaceutical active agent.

13. The pharmaceutical dosage form according to claim 12, wherein the centanafadine or a pharmaceutically acceptable salt thereof is present up to a ratio of about 1:50 parts by weight of centanafadine or salt thereof in the collection of one or more immediate release beads to the collection of one or more delayed release beads.

14. The pharmaceutical dosage form according to claim 12, wherein the centanafadine or a pharmaceutically acceptable salt thereof is present up to a ratio of about 1:20 parts by weight of centanafadine or salt thereof in the collection of one or more immediate release beads to the collection of one or more delayed release beads.

15. The pharmaceutical dosage form of claim 12, wherein the pharmaceutically acceptable salt is a hydrochloride salt.

16. The pharmaceutical dosage form of claim 12, wherein the one or more delayed release beads comprise a delayed release coating comprising one or more materials selected from amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, emulsion of glyceryl monostearate, triethyl citrate, polysorbate 80, and styrene vinylpyridine copolymer.

17. The pharmaceutical dosage form of claim 16, wherein the delayed release coating comprises poly(methyl acrylate-co-methyl methacrylate-co-methacrylic acid).

18. The pharmaceutical dosage form of claim 16, wherein the delayed release coating comprises a copolymer of methyl acrylate, methyl methacrylate and methacrylic acid in a molar ratio of about 7:3:1.

19. The pharmaceutical dosage form of claim 12, wherein the plurality of centanafadine beads further comprises one or more sustained release centanafadine beads.

20. The pharmaceutical dosage form of claim 1, wherein at least 40% of the centanafadine or salt thereof is released from formulation at a time in a range of 3 hours to 5 hours, and at least 90% of the centanafadine or salt thereof is released from the formulation at a time in a range of 12 hours to 14 hours, according to the United States Pharmacopeia <711> with Apparatus 1 (basket) at 37° C.+/−0.5° C. at 100 rpm, first in 1000 ml of a 0.1N HCl solution for 2 hours, then 1000 ml pH 7.4 buffered water at 37° C.+/−0.5° C. at 100 rpm for the remainder of the time.

21. The pharmaceutical dosage form of claim 1, wherein the formulation comprises centanafadine hydrochloride and provides an adult subject with a centanafadine plasma concentration at 1 hour post-dose ($C_{1hr}$) of at least 150 ng/mL, a centanafadine plasma concentration post-dose which remains at least 250 ng/mL over the time period 2 to 8 hours post-dose, and a concentration of centanafadine in the plasma at 16 hours after administration ($C_{16h}$) of less than 300 ng/mL.

22. The pharmaceutical dosage form of claim 1, wherein according to the United States Pharmacopeia <711> using Apparatus 1 (basket) in 1000 mL 0.1N hydrochloric acid at 37° C.+/−0.5° C. at 100 rpm for 2 hours, followed by Apparatus 1 (basket) in 1000 mL pH 7.4 phosphate buffer solution at 37° C.+/−0.5° C.) at 100 rpm for 12 hours, the release profile is characterized by a release of about 24% to about 48% centanafadine at the 3-hour mark.

23. The pharmaceutical dosage form of claim 1, wherein the dosage form provides an adult subject with a centanafadine plasma concentration at 1 hour post-dose ($C_{1hr}$) of at least 150 ng/mL, or in a range of about 150 ng/mL to about 610 ng/mL.

24. The pharmaceutical dosage form of claim 1, wherein the dosage form provides an adult subject with a concentration of centanafadine in the plasma at 12 hours after administration ($C_{12h}$) of at least 95 ng/mL or in a range of about ng/mL to about 450 ng/mL.

25. The pharmaceutical dosage form of claim 1, wherein the dosage form provides an adult subject with a concentration of centanafadine in the plasma at 16 hours after administration ($C_{16h}$) of less than 300 ng/mL or in a range of about 95 ng/mL to about 300 ng/mL.

26. The pharmaceutical dosage form of claim 1, wherein the dosage form provides an adult subject with a centanafadine plasma concentration post-dose which remains at least 75 ng/mL, or in a range of about 75 ng/mL to about 1500 ng/mL over the time period 2 to 8 hours post-dose.

27. The pharmaceutical dosage form of claim 1, wherein the dosage form provides an adult subject with a cumulative centanafadine plasma exposure in the 24-hour period after administration ($AUC_{0-24h}$) of at least 2400 ng·h/mL, or in a range of 2400 ng·h/mL to 12500 ng·h/mL.

28. The pharmaceutical dosage form of claim 1, wherein the dosage form provides an adult subject with a cumulative centanafadine plasma exposure after administration ($AUC_{0-inf}$) of at least 2400 ng·h/mL or in a range of 2400 ng·h/mL to 12500 ng·h/mL.

29. The pharmaceutical dosage form of claim 1, wherein the dosage form provides an adult subject with a centanafadine plasma concentration at 1 hour post-dose ($C_{1hr}$) in a range of about 150 ng/mL to about 610 ng/mL;

at 12 hours post-dose ($C_{12h}$) in a range of about 95 ng/mL to about 450 ng/mL;

at 16 hours post-dose ($C_{16h}$) in a range of about 95 ng/mL to about 300 ng/mL; and wherein the ratio $C_{16h}/C_{12h}$ is less than 1.

* * * * *